(12) United States Patent
Roingeard et al.

(10) Patent No.: US 8,765,143 B2
(45) Date of Patent: Jul. 1, 2014

(54) FUSION PROTEINS AND USE THEREOF FOR PREPARING HEPATITIS C VACCINES

(75) Inventors: Philippe Roingeard, Savonnieres (FR); Christophe Hourioux, Druye (FR); Romuald Patient, Joue-Les-Tours (FR)

(73) Assignee: Universite Francois Rabelais de Tours, Tours (FR)

( * ) Notice: Subject to any disclaimer, the term of this patent is extended or adjusted under 35 U.S.C. 154(b) by 549 days.

(21) Appl. No.: 12/999,448

(22) PCT Filed: Jun. 16, 2009

(86) PCT No.: PCT/FR2009/051142
§ 371 (c)(1),
(2), (4) Date: Mar. 3, 2011

(87) PCT Pub. No.: WO2009/153518
PCT Pub. Date: Dec. 23, 2009

(65) Prior Publication Data
US 2011/0150921 A1     Jun. 23, 2011

(30) Foreign Application Priority Data

Jun. 17, 2008 (FR) ..................................... 08 03377

(51) Int. Cl.
*A61K 39/29* (2006.01)
*C12N 15/62* (2006.01)

(52) U.S. Cl.
CPC ................ *A61K 39/29* (2013.01); *C12N 15/62* (2013.01); *C12N 2770/24222* (2013.01); *C12N 2770/24223* (2013.01); *C12N 2770/24134* (2013.01); *C12N 2730/10123* (2013.01); *C12N 2730/10134* (2013.01)
USPC .................. 424/228.1; 424/189.1; 424/227.1; 424/192.1

(58) Field of Classification Search
None
See application file for complete search history.

(56) References Cited

U.S. PATENT DOCUMENTS

2004/0146529 A1     7/2004 Selby et al.

FOREIGN PATENT DOCUMENTS

WO     2008/025067 A1     3/2008

OTHER PUBLICATIONS

Eble et al., 1987. Multiple topogenic sequences determine the transmembrane orientation of Hepatitis B surface antigen. Molecular and Cellular Biology, vol. 7 (10): 3591-3601.*

Flint et al. 2000. Functional characterization of intracellular and secreted forms of a truncated HCV E2 glycoprotein. J.Virol, 74(2): 702-709.*
Misumi et al., 2003. Effects of immunization with CCR5-based cycloimmunogen on Simian/HIVSF162P3 Challenge. The Journal of Immunology. vol. 176 (1): 463-471.*
Genbank AAM96927.1-HBV-S protein sequence (submitted 2003).*
Genbank AAM94419.1-HCV type 1a E1 & E2 polyprotein sequence (submitted 2002).*
Genbank AAC 40376.1-HCV type 1a E1 protein sequence (submitted 2006).*
Abaza et al., 1992. Effects of amino acid substitution outside an antigenic site on protein binding to monoclonal antibodies of predetermined specificity obtained by peptide immunization: Demonstration with region 94-100 (Antigenic site 3) of myoglobin. Journal of Protein Chemistry. vol. 11, No. 5, p. 433-444.*
Pranje et al., 1992. Deletions in the HBV small envelope protein: effect on assembly and secretion of surface antigen particles. J. Virol, 66 (10): 5832-5841.*
Michael A. Purdy. 2007. HBV S gene escape mutants. Asian J Transfus Sci. 1(2): 62-70.*
Rifkin et al., 1995. A single amino acid change between the antigenically different extracellular serine proteases V2 and B2 from *Dichelobacter nodosus*. Gene. 167 (1995). 279-283.*
Netter H J et al: "Antigenicity and immunogenicity of novel chimeric hepatitis B surface antigen particles with exposed hepatitis C virus epitopes", Journal of Virology, Mar. 1, 2001, pp. 2130-2141, vol. 75, No. 5, The American Society for Microbiology, US, XP002977998.
Patient R et al: "Chimeric hepatitis B and C viruses envelope proteins can form subviral particles: implications for the design of new vaccine strategies", New Biotechnology, Apr. 1, 2009, pp. 226-234, vol. 25, No. 4, XP026059214.
International Search Report, Dated Dec. 9, 2009, in PCT/FR2009/051142.

* cited by examiner

*Primary Examiner* — Nick Zou
(74) *Attorney, Agent, or Firm* — Young & Thompson

(57) ABSTRACT

An immunogenic fusion protein includes at least, on the C-terminal side, a first peptide composed of the S protein deleted of the transmembrane domain thereof located at the N-terminal end thereof, of a hepatitis B virus (HBV) isolate, and on the N-terminal side, a second peptide composed of the transmembrane domain and of the ectodomain of at least one envelope protein of a hepatitis C virus (HCV) isolate. A hybrid nucleic acid molecule encoding the fusion protein, and a vector including the hybrid nucleic acid molecule, a subviral particle including the fusion protein, an immunogenic composition including at least the fusion protein, or at least the hybrid nucleic acid molecule, or at least the subviral particle, and a cell line for the production of the fusion protein, or of the hybrid nucleic acid molecule, or of the subviral particle are described.

21 Claims, 13 Drawing Sheets

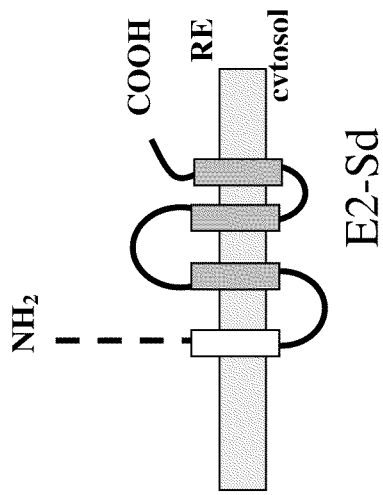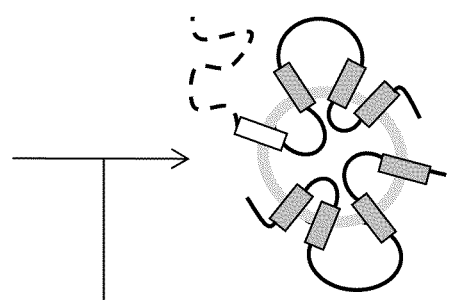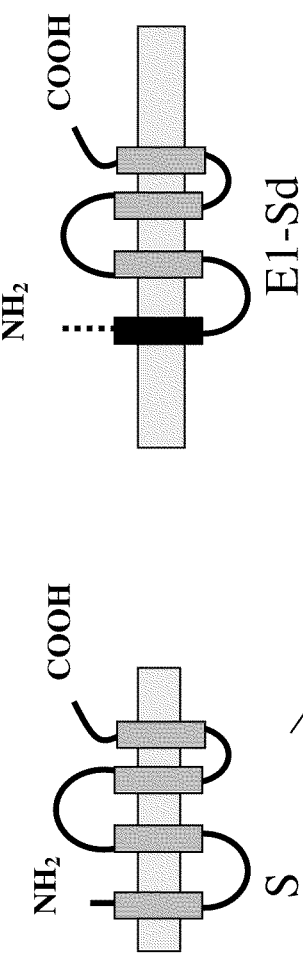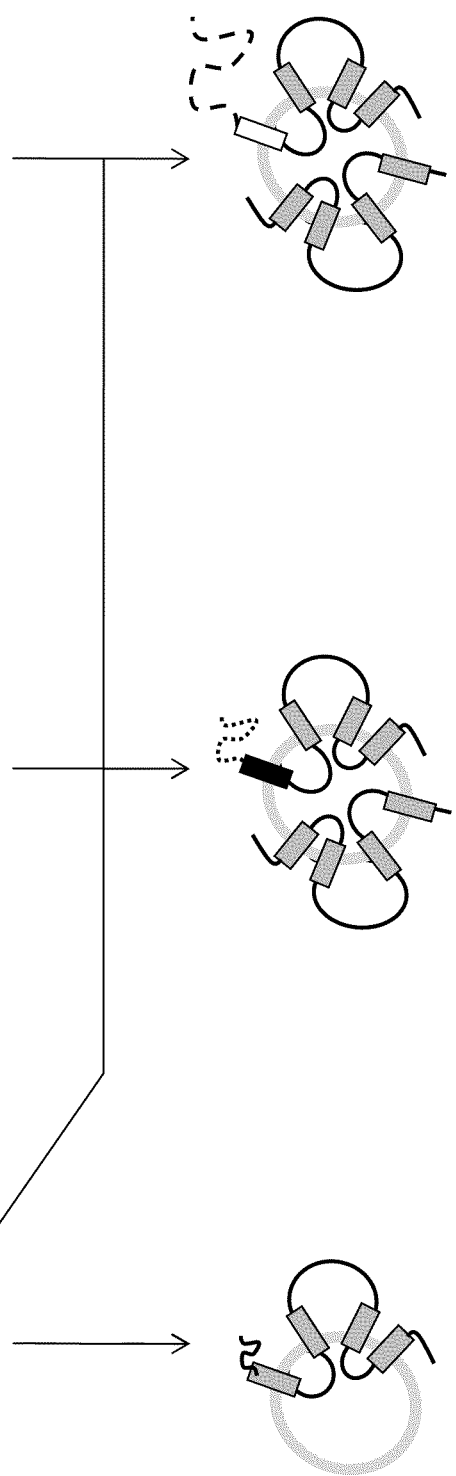

FIGURE 4A
FIGURE 4B
FIGURE 4C
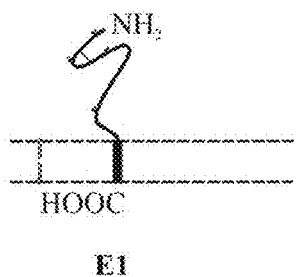
E1
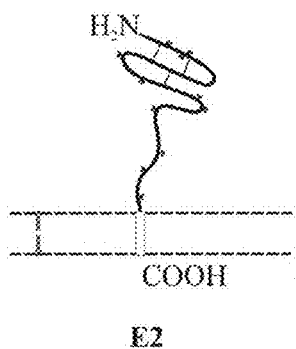
E2
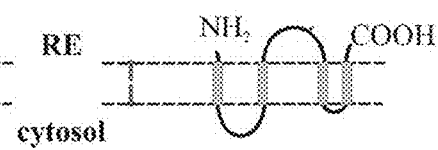
S
FIGURE 4D
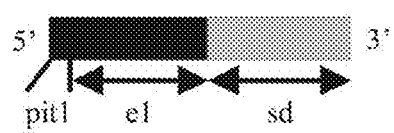
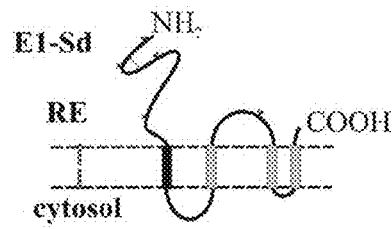
FIGURE 4E
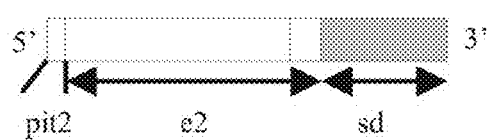
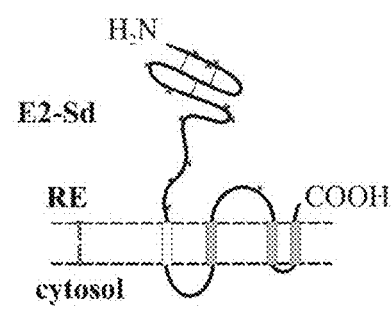

FIGURE 7A

FIGURE 11A
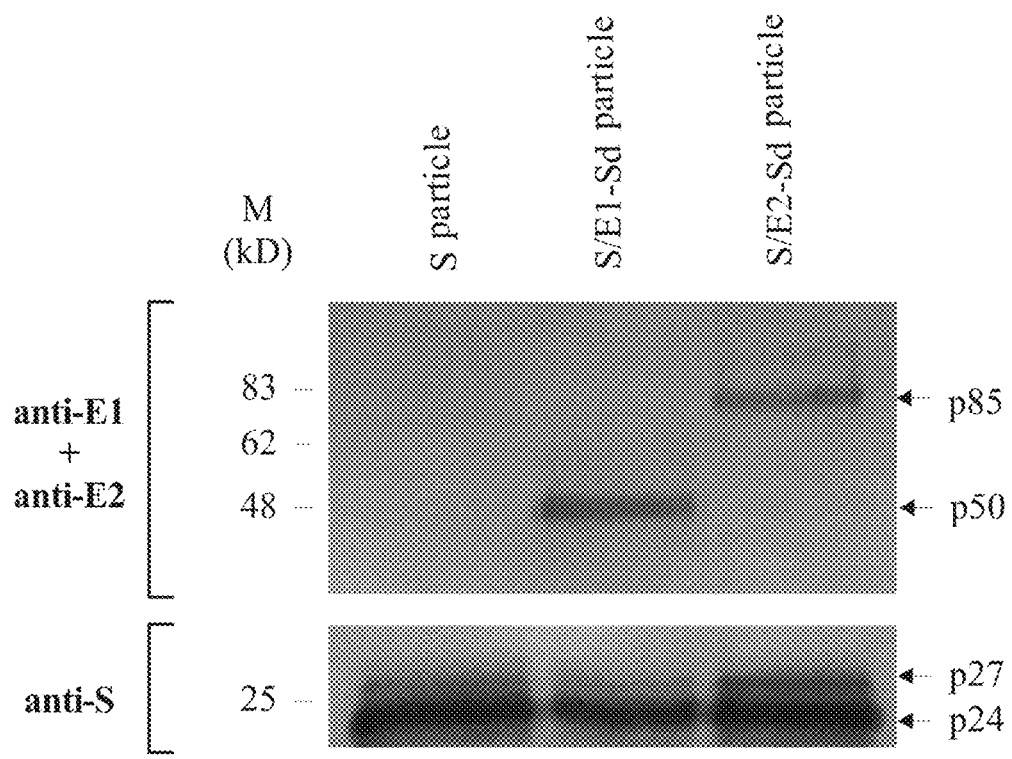
FIGURE 11B                FIGURE 11C                FIGURE 11D
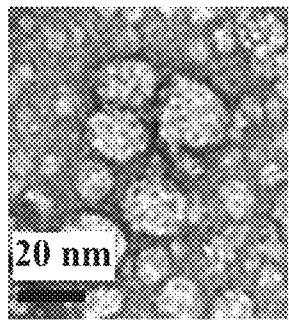   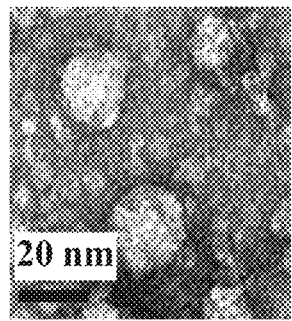   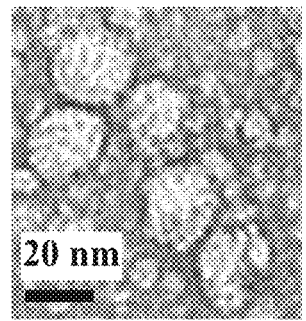

SEQUENCE LISTING

```
<160> NUMBER OF SEQ ID NOS: 16

<210> SEQ ID NO 1
<211> LENGTH: 612
<212> TYPE: DNA
<213> ORGANISM: Hepatitis B virus
<220> FEATURE:
<221> NAME/KEY: CDS
<222> LOCATION: (1)..(612)

<400> SEQUENCE: 1 aca aga atc ctc aca ata ccg cag agt cta gac tcg tgg tgg act tct      48
Thr Arg Ile Leu Thr Ile Pro Gln Ser Leu Asp Ser Trp Trp Thr Ser
1               5                   10                  15 ctc aat ttt cta ggg gga tct ccc gtg tgt ctt ggc caa aat tcg cag      96
Leu Asn Phe Leu Gly Gly Ser Pro Val Cys Leu Gly Gln Asn Ser Gln
            20                  25                  30 tcc cca acc tcc aat cac tca cca acc tcc tgt cct cca att tgt cct     144
Ser Pro Thr Ser Asn His Ser Pro Thr Ser Cys Pro Pro Ile Cys Pro
        35                  40                  45 ggt tat cgc tgg atg tgt ctg cgg cgt ttt atc ata ttc ctc ttc atc     192
Gly Tyr Arg Trp Met Cys Leu Arg Arg Phe Ile Ile Phe Leu Phe Ile
    50                  55                  60 ctg ctg cta tgc ctc atc ttc tta ttg gtt ctt ctg gat tat caa ggt     240
Leu Leu Leu Cys Leu Ile Phe Leu Leu Val Leu Leu Asp Tyr Gln Gly
65                  70                  75                  80 atg ttg ccc gtt tgt cct cta att cca gga tca aca aca acc agt acg     288
Met Leu Pro Val Cys Pro Leu Ile Pro Gly Ser Thr Thr Thr Ser Thr
                85                  90                  95 gga cca tgc aaa acc tgc acg act cct gct caa ggc aac tct atg ttt     336
Gly Pro Cys Lys Thr Cys Thr Thr Pro Ala Gln Gly Asn Ser Met Phe
            100                 105                 110 ccc tca tgt tgc tgt aca aaa cct acg gat gga aat tgc acc tgt att     384
Pro Ser Cys Cys Cys Thr Lys Pro Thr Asp Gly Asn Cys Thr Cys Ile
        115                 120                 125 ccc atc cca tcg tcc tgg gct ttc gca aaa tac cta tgg gag tgg gcc     432
Pro Ile Pro Ser Ser Trp Ala Phe Ala Lys Tyr Leu Trp Glu Trp Ala
    130                 135                 140 tca gtc cgt ttc tct tgg ctc agt tta cta gtg cca ttt gtt cag tgg     480
Ser Val Arg Phe Ser Trp Leu Ser Leu Leu Val Pro Phe Val Gln Trp
145                 150                 155                 160 ttc gta ggg ctt tcc ccc act gtt tgg ctt tca gct ata tgg atg atg     528
Phe Val Gly Leu Ser Pro Thr Val Trp Leu Ser Ala Ile Trp Met Met
                165                 170                 175 tgg tat tgg ggg cca agt ctg tac agc atc gtg agt ccc ttt ata ccg     576
Trp Tyr Trp Gly Pro Ser Leu Tyr Ser Ile Val Ser Pro Phe Ile Pro
            180                 185                 190 ctg tta cca att ttc ttt tgt ctc tgg gta tac att                      612
Leu Leu Pro Ile Phe Phe Cys Leu Trp Val Tyr Ile
        195                 200

<210> SEQ ID NO 2
<211> LENGTH: 204
<212> TYPE: PRT
<213> ORGANISM: Hepatitis B virus
```

<400> SEQUENCE: 2

```
Thr Arg Ile Leu Thr Ile Pro Gln Ser Leu Asp Ser Trp Trp Thr Ser
1               5                   10                  15
Leu Asn Phe Leu Gly Gly Ser Pro Val Cys Leu Gly Gln Asn Ser Gln
            20                  25                  30
Ser Pro Thr Ser Asn His Ser Pro Thr Ser Cys Pro Pro Ile Cys Pro
        35                  40                  45
Gly Tyr Arg Trp Met Cys Leu Arg Arg Phe Ile Ile Phe Leu Phe Ile
    50                  55                  60
Leu Leu Leu Cys Leu Ile Phe Leu Leu Val Leu Leu Asp Tyr Gln Gly
65                  70                  75                  80
Met Leu Pro Val Cys Pro Leu Ile Pro Gly Ser Thr Thr Thr Ser Thr
                85                  90                  95
Gly Pro Cys Lys Thr Cys Thr Thr Pro Ala Gln Gly Asn Ser Met Phe
            100                 105                 110
Pro Ser Cys Cys Cys Thr Lys Pro Thr Asp Gly Asn Cys Thr Cys Ile
        115                 120                 125
Pro Ile Pro Ser Ser Trp Ala Phe Ala Lys Tyr Leu Trp Glu Trp Ala
    130                 135                 140
Ser Val Arg Phe Ser Trp Leu Ser Leu Leu Val Pro Phe Val Gln Trp
145                 150                 155                 160
Phe Val Gly Leu Ser Pro Thr Val Trp Leu Ser Ala Ile Trp Met Met
                165                 170                 175
Trp Tyr Trp Gly Pro Ser Leu Tyr Ser Ile Val Ser Pro Phe Ile Pro
            180                 185                 190
Leu Leu Pro Ile Phe Phe Cys Leu Trp Val Tyr Ile
        195                 200
```

<210> SEQ ID NO 3
<211> LENGTH: 576
<212> TYPE: DNA
<213> ORGANISM: Hepatitis C virus
<220> FEATURE:
<221> NAME/KEY: CDS
<222> LOCATION: (1)..(576)

<400> SEQUENCE: 3

```
tac caa gta cgc aac tcc tcg ggc ctt tac cat gtc acc aat gat tgc      48
Tyr Gln Val Arg Asn Ser Ser Gly Leu Tyr His Val Thr Asn Asp Cys
1               5                   10                  15 cct aac tcg agt att gtg tac gag acg gcc gat acc atc cta cac tct      96
Pro Asn Ser Ser Ile Val Tyr Glu Thr Ala Asp Thr Ile Leu His Ser
            20                  25                  30 ccg ggg tgt gtc cct tgc gtt cgc gag ggc aat gcc tca aaa tgt tgg     144
Pro Gly Cys Val Pro Cys Val Arg Glu Gly Asn Ala Ser Lys Cys Trp
        35                  40                  45 gtg gcg gtg gcc cct aca gtc gcc acc aga gac ggc aag ctc ccc aca     192
Val Ala Val Ala Pro Thr Val Ala Thr Arg Asp Gly Lys Leu Pro Thr
    50                  55                  60 acg cag ctt cga cgt cac atc gat ctg ctc gtc agg agc gcc acc ctc     240
Thr Gln Leu Arg Arg His Ile Asp Leu Leu Val Arg Ser Ala Thr Leu
65                  70                  75                  80 tgc tcg gcc ctc tat gtg ggg gac ttg tgc ggg tcc gtc ttc ctc gtc     288
Cys Ser Ala Leu Tyr Val Gly Asp Leu Cys Gly Ser Val Phe Leu Val
                85                  90                  95 ggt caa ctg ttc acc ttc tcc ccc agg cgc cac tgg aca acg caa gac     336
Gly Gln Leu Phe Thr Phe Ser Pro Arg Arg His Trp Thr Thr Gln Asp
            100                 105                 110
```

```
tgc aac tgt tcc atg tac ccc ggc cat ata acg ggt cac cgt atg gca      384
Cys Asn Cys Ser Met Tyr Pro Gly His Ile Thr Gly His Arg Met Ala
        115                 120                 125 tgg gac atg atg atg aac tgg tcc cct acg aca gcg ctg gta gta gct      432
Trp Asp Met Met Met Asn Trp Ser Pro Thr Thr Ala Leu Val Val Ala
130                 135                 140 cag ctg ctc agg gtc ccg caa gcc atc ttg gac atg atc gct ggt gcc      480
Gln Leu Leu Arg Val Pro Gln Ala Ile Leu Asp Met Ile Ala Gly Ala
145                 150                 155                 160 cac tgg gga gtc cta gcg ggc ata gcg tat ttc tcc atg gtg ggg aac      528
His Trp Gly Val Leu Ala Gly Ile Ala Tyr Phe Ser Met Val Gly Asn
                165                 170                 175 tgg gcg aag gtc ctg gtg gtg ctg ttg ctg ttc gcc agc gtc gat gcg      576
Trp Ala Lys Val Leu Val Val Leu Leu Leu Phe Ala Ser Val Asp Ala
            180                 185                 190
```

<210> SEQ ID NO 4
<211> LENGTH: 192
<212> TYPE: PRT
<213> ORGANISM: Hepatitis C virus

<400> SEQUENCE: 4

Tyr Gln Val Arg Asn Ser Ser Gly Leu Tyr His Val Thr Asn Asp Cys
1               5                   10                  15

Pro Asn Ser Ser Ile Val Tyr Glu Thr Ala Asp Thr Ile Leu His Ser
            20                  25                  30

Pro Gly Cys Val Pro Cys Val Arg Glu Gly Asn Ala Ser Lys Cys Trp
        35                  40                  45

Val Ala Val Ala Pro Thr Val Ala Thr Arg Asp Gly Lys Leu Pro Thr
    50                  55                  60

Thr Gln Leu Arg Arg His Ile Asp Leu Leu Val Arg Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Asp
            100                 105                 110

Cys Asn Cys Ser Met Tyr Pro Gly His Ile Thr Gly His Arg Met Ala
        115                 120                 125

Trp Asp Met Met Met Asn Trp Ser Pro Thr Thr Ala Leu Val Val Ala
    130                 135                 140

Gln Leu Leu Arg Val Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Ser Val Asp Ala
            180                 185                 190

<210> SEQ ID NO 5
<211> LENGTH: 1089
<212> TYPE: DNA
<213> ORGANISM: Hepatitis C virus
<220> FEATURE:
<221> NAME/KEY: CDS
<222> LOCATION: (1)..(1089)

<400> SEQUENCE: 5

```
gaa acc tac acc acc ggg ggg agt att gcc aaa acc gtg caa gga ttc       48
Glu Thr Tyr Thr Thr Gly Gly Ser Ile Ala Lys Thr Val Gln Gly Phe
1               5                   10                  15
```

```
acc agt ttt ttt acc cca ggc gcc aag cag gac atc cag ctg atc aac      96
Thr Ser Phe Phe Thr Pro Gly Ala Lys Gln Asp Ile Gln Leu Ile Asn
         20                  25                  30 acc aac ggc agt tgg cac atc aat cgc acg gcc ttg aac tgt aat gcg     144
Thr Asn Gly Ser Trp His Ile Asn Arg Thr Ala Leu Asn Cys Asn Ala
         35                  40                  45 agc ctc gaa acc ggc tgg ata gcg ggg ctc ttc tac tac aac aaa ttc     192
Ser Leu Glu Thr Gly Trp Ile Ala Gly Leu Phe Tyr Tyr Asn Lys Phe
         50                  55                  60 aac tcc tca ggc tgc ccc gag agg atg gcc agc tgc aaa ccc ctt gcc     240
Asn Ser Ser Gly Cys Pro Glu Arg Met Ala Ser Cys Lys Pro Leu Ala
65                  70                  75                  80 tat ttc gcc caa ggc tgg ggc cct atc agc cat gtc aac gga agc ggc     288
Tyr Phe Ala Gln Gly Trp Gly Pro Ile Ser His Val Asn Gly Ser Gly
                     85                  90                  95 ccc gaa cag cgc ccc tac tgc tgg cac tac gcc cca agg cct tgt ggt     336
Pro Glu Gln Arg Pro Tyr Cys Trp His Tyr Ala Pro Arg Pro Cys Gly
                    100                 105                 110 atc gtg tca gca cag aca gta tgt ggc cca gtg tat tgt ttc act cct     384
Ile Val Ser Ala Gln Thr Val Cys Gly Pro Val Tyr Cys Phe Thr Pro
                115                 120                 125 agc ccc gtg gtg gtg ggg acg acc gac aag ttg ggc gcg cct acc tac     432
Ser Pro Val Val Val Gly Thr Thr Asp Lys Leu Gly Ala Pro Thr Tyr
130                 135                 140 aac tgg ggt gag aat gat acg gac gtc ttc gtc ctc aat aac acc agg     480
Asn Trp Gly Glu Asn Asp Thr Asp Val Phe Val Leu Asn Asn Thr Arg
145                 150                 155                 160 cca ccg ttg ggc aat tgg ttc ggt tgc acc tgg atg aac tca tct gga     528
Pro Pro Leu Gly Asn Trp Phe Gly Cys Thr Trp Met Asn Ser Ser Gly
                165                 170                 175 ttc acc aaa gtg tgc gga gcg cct ccc tgt gcc atc gga gga gtg ggc     576
Phe Thr Lys Val Cys Gly Ala Pro Pro Cys Ala Ile Gly Gly Val Gly
                180                 185                 190 aat aac acc ttg cgc tgt ccc act gac tgt ttc cgc aag cat ccg gaa     624
Asn Asn Thr Leu Arg Cys Pro Thr Asp Cys Phe Arg Lys His Pro Glu
            195                 200                 205 gct aca tac tct cga tgt ggc tcc ggt ccc tgg atc acg ccc agg tgc     672
Ala Thr Tyr Ser Arg Cys Gly Ser Gly Pro Trp Ile Thr Pro Arg Cys
        210                 215                 220 ctg gtc gac tat cct tat agg ctc tgg cat tat cct tgc act gtc aac     720
Leu Val Asp Tyr Pro Tyr Arg Leu Trp His Tyr Pro Cys Thr Val Asn
225                 230                 235                 240 tac acc ctg ttt aaa atc agg atg tac gtg gga ggg gtc gag cac agg     768
Tyr Thr Leu Phe Lys Ile Arg Met Tyr Val Gly Gly Val Glu His Arg
                245                 250                 255 cta caa gct gct tgc aac tgg acg cgg ggc gag cgt tgt gat ctg gac     816
Leu Gln Ala Ala Cys Asn Trp Thr Arg Gly Glu Arg Cys Asp Leu Asp
                260                 265                 270 gac agg gac agg tcc gag ctc agc ccg ctg ctg ctg tcc acc acg cag     864
Asp Arg Asp Arg Ser Glu Leu Ser Pro Leu Leu Leu Ser Thr Thr Gln
            275                 280                 285 tgg cag gtc ctt ccg tgt tct ttc acg acc ttg cca gcc ttg acc acc     912
Trp Gln Val Leu Pro Cys Ser Phe Thr Thr Leu Pro Ala Leu Thr Thr
        290                 295                 300 ggc ctc atc cac ctc cat cag aac atc gtg gac gtg caa tat ttg tac     960
Gly Leu Ile His Leu His Gln Asn Ile Val Asp Val Gln Tyr Leu Tyr
305                 310                 315                 320 ggg gtg ggg tca agc att gtg tcc tgg gcc atc aag tgg gag tac gtc    1008
Gly Val Gly Ser Ser Ile Val Ser Trp Ala Ile Lys Trp Glu Tyr Val
```

```
                    325                 330                 335
att ctc ttg ttt ctc ctg ctt gca gac gcg cgc atc tgc tcc tgc ttg      1056
Ile Leu Leu Phe Leu Leu Leu Ala Asp Ala Arg Ile Cys Ser Cys Leu
        340                 345                 350 tgg atg atg cta ctc ata tcc caa gcg gag gcg                          1089
Trp Met Met Leu Leu Ile Ser Gln Ala Glu Ala
        355                 360

<210> SEQ ID NO 6
<211> LENGTH: 363
<212> TYPE: PRT
<213> ORGANISM: Hepatitis C virus

<400> SEQUENCE: 6

Glu Thr Tyr Thr Thr Gly Gly Ser Ile Ala Lys Thr Val Gln Gly Phe
1               5                   10                  15

Thr Ser Phe Phe Thr Pro Gly Ala Lys Gln Asp Ile Gln Leu Ile Asn
            20                  25                  30

Thr Asn Gly Ser Trp His Ile Asn Arg Thr Ala Leu Asn Cys Asn Ala
        35                  40                  45

Ser Leu Glu Thr Gly Trp Ile Ala Gly Leu Phe Tyr Tyr Asn Lys Phe
50                  55                  60

Asn Ser Ser Gly Cys Pro Glu Arg Met Ala Ser Cys Lys Pro Leu Ala
65                  70                  75                  80

Tyr Phe Ala Gln Gly Trp Gly Pro Ile Ser His Val Asn Gly Ser Gly
                85                  90                  95

Pro Glu Gln Arg Pro Tyr Cys Trp His Tyr Ala Pro Arg Pro Cys Gly
            100                 105                 110

Ile Val Ser Ala Gln Thr Val Cys Gly Pro Val Tyr Cys Phe Thr Pro
        115                 120                 125

Ser Pro Val Val Gly Thr Thr Asp Lys Leu Gly Ala Pro Thr Tyr
130                 135                 140

Asn Trp Gly Glu Asn Asp Thr Asp Val Phe Val Leu Asn Asn Thr Arg
145                 150                 155                 160

Pro Pro Leu Gly Asn Trp Phe Gly Cys Thr Trp Met Asn Ser Ser Gly
                165                 170                 175

Phe Thr Lys Val Cys Gly Ala Pro Pro Cys Ala Ile Gly Gly Val Gly
            180                 185                 190

Asn Asn Thr Leu Arg Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
210                 215                 220

Leu Val Asp Tyr Pro Tyr Arg Leu Trp His Tyr Pro Cys Thr Val Asn
225                 230                 235                 240

Tyr Thr Leu Phe Lys Ile Arg Met Tyr Val Gly Gly Val Glu His Arg
                245                 250                 255

Leu Gln Ala Ala Cys Asn Trp Thr Arg Gly Glu Arg Cys Asp Leu Asp
            260                 265                 270

Asp Arg Asp Arg Ser Glu Leu Ser Pro Leu Leu Leu Ser Thr Thr Gln
        275                 280                 285

Trp Gln Val Leu Pro Cys Ser Phe Thr Thr Leu Pro Ala Leu Thr Thr
290                 295                 300

Gly Leu Ile His Leu His Gln Asn Ile Val Asp Val Gln Tyr Leu Tyr
305                 310                 315                 320

Gly Val Gly Ser Ser Ile Val Ser Trp Ala Ile Lys Trp Glu Tyr Val
```

```
                    325                 330                 335
Ile Leu Leu Phe Leu Leu Leu Ala Asp Ala Arg Ile Cys Ser Cys Leu
            340                 345                 350

Trp Met Met Leu Leu Ile Ser Gln Ala Glu Ala
            355                 360

<210> SEQ ID NO 7
<211> LENGTH: 1182
<212> TYPE: DNA
<213> ORGANISM: Artificial Sequence
<220> FEATURE:
<223> OTHER INFORMATION: derived from HCV and HBV
<220> FEATURE:
<221> NAME/KEY: CDS
<222> LOCATION: (1)..(1182)

<400> SEQUENCE: 7 tac caa gta cgc aac tcc tcg ggc ctt tac cat gtc acc aat gat tgc        48
Tyr Gln Val Arg Asn Ser Ser Gly Leu Tyr His Val Thr Asn Asp Cys
1               5                   10                  15 cct aac tcg agt att gtg tac gag acg gcc gat acc atc cta cac tct        96
Pro Asn Ser Ser Ile Val Tyr Glu Thr Ala Asp Thr Ile Leu His Ser
            20                  25                  30 ccg ggg tgt gtc cct tgc gtt cgc gag ggc aat gcc tca aaa tgt tgg       144
Pro Gly Cys Val Pro Cys Val Arg Glu Gly Asn Ala Ser Lys Cys Trp
        35                  40                  45 gtg gcg gtg gcc cct aca gtc gcc acc aga gac ggc aag ctc ccc aca       192
Val Ala Val Ala Pro Thr Val Ala Thr Arg Asp Gly Lys Leu Pro Thr
    50                  55                  60 acg cag ctt cga cgt cac atc gat ctg ctc gtc agg agc gcc acc ctc       240
Thr Gln Leu Arg Arg His Ile Asp Leu Leu Val Arg Ser Ala Thr Leu
65                  70                  75                  80 tgc tcg gcc ctc tat gtg ggg gac ttg tgc ggg tcc gtc ttc ctc gtc       288
Cys Ser Ala Leu Tyr Val Gly Asp Leu Cys Gly Ser Val Phe Leu Val
                85                  90                  95 ggt caa ctg ttc acc ttc tcc ccc agg cgc cac tgg aca acg caa gac       336
Gly Gln Leu Phe Thr Phe Ser Pro Arg Arg His Trp Thr Thr Gln Asp
            100                 105                 110 tgc aac tgt tcc atg tac ccc ggc cat ata acg ggt cac cgt atg gca       384
Cys Asn Cys Ser Met Tyr Pro Gly His Ile Thr Gly His Arg Met Ala
        115                 120                 125 tgg gac atg atg atg aac tgg tcc cct acg aca gcg ctg gta gta gct       432
Trp Asp Met Met Met Asn Trp Ser Pro Thr Thr Ala Leu Val Val Ala
    130                 135                 140 cag ctg ctc agg gtc ccg caa gcc atc ttg gac atg atc gct ggt gcc       480
Gln Leu Leu Arg Val Pro Gln Ala Ile Leu Asp Met Ile Ala Gly Ala
145                 150                 155                 160 cac tgg gga gtc cta gcg ggc ata gcg tat ttc tcc atg gtg ggg aac       528
His Trp Gly Val Leu Ala Gly Ile Ala Tyr Phe Ser Met Val Gly Asn
                165                 170                 175 tgg gcg aag gtc ctg gtg gtg ctg ttg ctg ttc gcc agc aca aga atc       576
Trp Ala Lys Val Leu Val Val Leu Leu Leu Phe Ala Ser Thr Arg Ile
            180                 185                 190 ctc aca ata ccg cag agt cta gac tcg tgg tgg act tct ctc aat ttt       624
Leu Thr Ile Pro Gln Ser Leu Asp Ser Trp Trp Thr Ser Leu Asn Phe
        195                 200                 205 cta ggg gga tct ccc gtg tgt ctt ggc caa aat tcg cag tcc cca acc       672
Leu Gly Gly Ser Pro Val Cys Leu Gly Gln Asn Ser Gln Ser Pro Thr
    210                 215                 220 tcc aat cac tca cca acc tcc tgt cct cca att tgt cct ggt tat cgc       720
Ser Asn His Ser Pro Thr Ser Cys Pro Pro Ile Cys Pro Gly Tyr Arg
```

```
                  225                 230                 235                 240
tgg atg tgt ctg cgg cgt ttt atc ata ttc ctc ttc atc ctg ctg cta          768
Trp Met Cys Leu Arg Arg Phe Ile Ile Phe Leu Phe Ile Leu Leu Leu
                245                 250                 255 tgc ctc atc ttc tta ttg gtt ctt ctg gat tat caa ggt atg ttg ccc          816
Cys Leu Ile Phe Leu Leu Val Leu Leu Asp Tyr Gln Gly Met Leu Pro
                260                 265                 270 gtt tgt cct cta att cca gga tca aca aca acc agt acg gga cca tgc          864
Val Cys Pro Leu Ile Pro Gly Ser Thr Thr Thr Ser Thr Gly Pro Cys
                275                 280                 285 aaa acc tgc acg act cct gct caa ggc aac tct atg ttt ccc tca tgt          912
Lys Thr Cys Thr Thr Pro Ala Gln Gly Asn Ser Met Phe Pro Ser Cys
                290                 295                 300 tgc tgt aca aaa cct acg gat gga aat tgc acc tgt att ccc atc cca          960
Cys Cys Thr Lys Pro Thr Asp Gly Asn Cys Thr Cys Ile Pro Ile Pro
305                 310                 315                 320 tcg tcc tgg gct ttc gca aaa tac cta tgg gag tgg gcc tca gtc cgt         1008
Ser Ser Trp Ala Phe Ala Lys Tyr Leu Trp Glu Trp Ala Ser Val Arg
                325                 330                 335 ttc tct tgg ctc agt tta cta gtg cca ttt gtt cag tgg ttc gta ggg         1056
Phe Ser Trp Leu Ser Leu Leu Val Pro Phe Val Gln Trp Phe Val Gly
                340                 345                 350 ctt tcc ccc act gtt tgg ctt tca gct ata tgg atg atg tgg tat tgg         1104
Leu Ser Pro Thr Val Trp Leu Ser Ala Ile Trp Met Met Trp Tyr Trp
                355                 360                 365 ggg cca agt ctg tac agc atc gtg agt ccc ttt ata ccg ctg tta cca         1152
Gly Pro Ser Leu Tyr Ser Ile Val Ser Pro Phe Ile Pro Leu Leu Pro
                370                 375                 380 att ttc ttt tgt ctc tgg gta tac att taa                                  1182
Ile Phe Phe Cys Leu Trp Val Tyr Ile
385                 390

<210> SEQ ID NO 8
<211> LENGTH: 393
<212> TYPE: PRT
<213> ORGANISM: Artificial Sequence
<220> FEATURE:
<223> OTHER INFORMATION: Synthetic Construct

<400> SEQUENCE: 8

Tyr Gln Val Arg Asn Ser Ser Gly Leu Tyr His Val Thr Asn Asp Cys
1               5                   10                  15

Pro Asn Ser Ser Ile Val Tyr Glu Thr Ala Asp Thr Ile Leu His Ser
            20                  25                  30

Pro Gly Cys Val Pro Cys Val Arg Glu Gly Asn Ala Ser Lys Cys Trp
        35                  40                  45

Val Ala Val Ala Pro Thr Val Ala Thr Arg Asp Gly Lys Leu Pro Thr
    50                  55                  60

Thr Gln Leu Arg Arg His Ile Asp Leu Leu Val Arg Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Asp
            100                 105                 110

Cys Asn Cys Ser Met Tyr Pro Gly His Ile Thr Gly His Arg Met Ala
        115                 120                 125

Trp Asp Met Met Met Asn Trp Ser Pro Thr Thr Ala Leu Val Val Ala
    130                 135                 140
```

```
Gln Leu Leu Arg Val Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Ser Thr Arg Ile
            180                 185                 190

Leu Thr Ile Pro Gln Ser Leu Asp Ser Trp Trp Thr Ser Leu Asn Phe
        195                 200                 205

Leu Gly Gly Ser Pro Val Cys Leu Gly Gln Asn Ser Gln Ser Pro Thr
    210                 215                 220

Ser Asn His Ser Pro Thr Ser Cys Pro Pro Ile Cys Pro Gly Tyr Arg
225                 230                 235                 240

Trp Met Cys Leu Arg Arg Phe Ile Ile Phe Leu Phe Ile Leu Leu Leu
                245                 250                 255

Cys Leu Ile Phe Leu Leu Val Leu Leu Asp Tyr Gln Gly Met Leu Pro
            260                 265                 270

Val Cys Pro Leu Ile Pro Gly Ser Thr Thr Thr Ser Thr Gly Pro Cys
        275                 280                 285

Lys Thr Cys Thr Thr Pro Ala Gln Gly Asn Ser Met Phe Pro Ser Cys
    290                 295                 300

Cys Cys Thr Lys Pro Thr Asp Gly Asn Cys Thr Cys Ile Pro Ile Pro
305                 310                 315                 320

Ser Ser Trp Ala Phe Ala Lys Tyr Leu Trp Glu Trp Ala Ser Val Arg
                325                 330                 335

Phe Ser Trp Leu Ser Leu Leu Val Pro Phe Val Gln Trp Phe Val Gly
            340                 345                 350

Leu Ser Pro Thr Val Trp Leu Ser Ala Ile Trp Met Met Trp Tyr Trp
        355                 360                 365

Gly Pro Ser Leu Tyr Ser Ile Val Ser Pro Phe Ile Pro Leu Leu Pro
    370                 375                 380

Ile Phe Phe Cys Leu Trp Val Tyr Ile
385                 390

<210> SEQ ID NO 9
<211> LENGTH: 1695
<212> TYPE: DNA
<213> ORGANISM: Artificial Sequence
<220> FEATURE:
<223> OTHER INFORMATION: derived from HCV and HBV
<220> FEATURE:
<221> NAME/KEY: CDS
<222> LOCATION: (1)..(1695)

<400> SEQUENCE: 9 gaa acc tac acc acc ggg ggg agt att gcc aaa acc gtg caa gga ttc    48
Glu Thr Tyr Thr Thr Gly Gly Ser Ile Ala Lys Thr Val Gln Gly Phe
1               5                   10                  15 acc agt ttt ttt acc cca ggc gcc aag cag gac atc cag ctg atc aac    96
Thr Ser Phe Phe Thr Pro Gly Ala Lys Gln Asp Ile Gln Leu Ile Asn
            20                  25                  30 acc aac ggc agt tgg cac atc aat cgc acg gcc ttg aac tgt aat gcg   144
Thr Asn Gly Ser Trp His Ile Asn Arg Thr Ala Leu Asn Cys Asn Ala
        35                  40                  45 agc ctc gaa acc ggc tgg ata gcg ggg ctc ttc tac tac aac aaa ttc   192
Ser Leu Glu Thr Gly Trp Ile Ala Gly Leu Phe Tyr Tyr Asn Lys Phe
    50                  55                  60 aac tcc tca ggc tgc ccc gag agg atg gcc agc tgc aaa ccc ctt gcc   240
Asn Ser Ser Gly Cys Pro Glu Arg Met Ala Ser Cys Lys Pro Leu Ala
```

-continued

```
            65                  70                  75                  80
tat ttc gcc caa ggc tgg ggc cct atc agc cat gtc aac gga agc ggc        288
Tyr Phe Ala Gln Gly Trp Gly Pro Ile Ser His Val Asn Gly Ser Gly
                    85                  90                  95 ccc gaa cag cgc ccc tac tgc tgg cac tac gcc cca agg cct tgt ggt        336
Pro Glu Gln Arg Pro Tyr Cys Trp His Tyr Ala Pro Arg Pro Cys Gly
                100                 105                 110 atc gtg tca gca cag aca gta tgt ggc cca gtg tat tgt ttc act cct        384
Ile Val Ser Ala Gln Thr Val Cys Gly Pro Val Tyr Cys Phe Thr Pro
            115                 120                 125 agc ccc gtg gtg gtg ggg acg acc gac aag ttg ggc gcg cct acc tac        432
Ser Pro Val Val Val Gly Thr Thr Asp Lys Leu Gly Ala Pro Thr Tyr
        130                 135                 140 aac tgg ggt gag aat gat acg gac gtc ttc gtc ctc aat aac acc agg        480
Asn Trp Gly Glu Asn Asp Thr Asp Val Phe Val Leu Asn Asn Thr Arg
145                 150                 155                 160 cca ccg ttg ggc aat tgg ttc ggt tgc acc tgg atg aac tca tct gga        528
Pro Pro Leu Gly Asn Trp Phe Gly Cys Thr Trp Met Asn Ser Ser Gly
                165                 170                 175 ttc acc aaa gtg tgc gga gcg cct ccc tgt gcc atc gga gga gtg ggc        576
Phe Thr Lys Val Cys Gly Ala Pro Pro Cys Ala Ile Gly Gly Val Gly
            180                 185                 190 aat aac acc ttg cgc tgt ccc act gac tgt ttc cgc aag cat ccg gaa        624
Asn Asn Thr Leu Arg Cys Pro Thr Asp Cys Phe Arg Lys His Pro Glu
        195                 200                 205 gct aca tac tct cga tgt ggc tcc ggt ccc tgg atc acg ccc agg tgc        672
Ala Thr Tyr Ser Arg Cys Gly Ser Gly Pro Trp Ile Thr Pro Arg Cys
    210                 215                 220 ctg gtc gac tat cct tat agg ctc tgg cat tat cct tgc act gtc aac        720
Leu Val Asp Tyr Pro Tyr Arg Leu Trp His Tyr Pro Cys Thr Val Asn
225                 230                 235                 240 tac acc ctg ttt aaa atc agg atg tac gtg gga ggg gtc gag cac agg        768
Tyr Thr Leu Phe Lys Ile Arg Met Tyr Val Gly Gly Val Glu His Arg
                245                 250                 255 cta caa gct gct tgc aac tgg acg cgg ggc gag cgt tgt gat ctg gac        816
Leu Gln Ala Ala Cys Asn Trp Thr Arg Gly Glu Arg Cys Asp Leu Asp
            260                 265                 270 gac agg gac agg tcc gag ctc agc ccg ctg ctg ctg tcc acc acg cag        864
Asp Arg Asp Arg Ser Glu Leu Ser Pro Leu Leu Leu Ser Thr Thr Gln
        275                 280                 285 tgg cag gtc ctt ccg tgt tct ttc acg acc ttg cca gcc ttg acc acc        912
Trp Gln Val Leu Pro Cys Ser Phe Thr Thr Leu Pro Ala Leu Thr Thr
    290                 295                 300 ggc ctc atc cac ctc cat cag aac atc gtg gac gtg caa tat ttg tac        960
Gly Leu Ile His Leu His Gln Asn Ile Val Asp Val Gln Tyr Leu Tyr
305                 310                 315                 320 ggg gtg ggg tca agc att gtg tcc tgg gcc atc aag tgg gag tac gtc        1008
Gly Val Gly Ser Ser Ile Val Ser Trp Ala Ile Lys Trp Glu Tyr Val
                325                 330                 335 att ctc ttg ttt ctc ctg ctt gca gac gcg cgc atc tgc tcc tgc ttg        1056
Ile Leu Leu Phe Leu Leu Leu Ala Asp Ala Arg Ile Cys Ser Cys Leu
            340                 345                 350 tgg atg atg cta ctc ata tcc caa aca aga atc ctc aca ata ccg cag        1104
Trp Met Met Leu Leu Ile Ser Gln Thr Arg Ile Leu Thr Ile Pro Gln
        355                 360                 365 agt cta gac tcg tgg tgg act tct ctc aat ttt cta ggg gga tct ccc        1152
Ser Leu Asp Ser Trp Trp Thr Ser Leu Asn Phe Leu Gly Gly Ser Pro
    370                 375                 380 gtg tgt ctt ggc caa aat tcg cag tcc cca acc tcc aat cac tca cca        1200
```

```
Val Cys Leu Gly Gln Asn Ser Gln Ser Pro Thr Ser Asn His Ser Pro
385                 390                 395                 400 acc tcc tgt cct cca att tgt cct ggt tat cgc tgg atg tgt ctg cgg      1248
Thr Ser Cys Pro Pro Ile Cys Pro Gly Tyr Arg Trp Met Cys Leu Arg
                405                 410                 415 cgt ttt atc ata ttc ctc ttc atc ctg ctg cta tgc ctc atc ttc tta      1296
Arg Phe Ile Ile Phe Leu Phe Ile Leu Leu Leu Cys Leu Ile Phe Leu
            420                 425                 430 ttg gtt ctt ctg gat tat caa ggt atg ttg ccc gtt tgt cct cta att      1344
Leu Val Leu Leu Asp Tyr Gln Gly Met Leu Pro Val Cys Pro Leu Ile
        435                 440                 445 cca gga tca aca aca acc agt acg gga cca tgc aaa acc tgc acg act      1392
Pro Gly Ser Thr Thr Thr Ser Thr Gly Pro Cys Lys Thr Cys Thr Thr
    450                 455                 460 cct gct caa ggc aac tct atg ttt ccc tca tgt tgc tgt aca aaa cct      1440
Pro Ala Gln Gly Asn Ser Met Phe Pro Ser Cys Cys Cys Thr Lys Pro
465                 470                 475                 480 acg gat gga aat tgc acc tgt att ccc atc cca tcg tcc tgg gct ttc      1488
Thr Asp Gly Asn Cys Thr Cys Ile Pro Ile Pro Ser Ser Trp Ala Phe
                485                 490                 495 gca aaa tac cta tgg gag tgg gcc tca gtc cgt ttc tct tgg ctc agt      1536
Ala Lys Tyr Leu Trp Glu Trp Ala Ser Val Arg Phe Ser Trp Leu Ser
            500                 505                 510 tta cta gtg cca ttt gtt cag tgg ttc gta ggg ctt tcc ccc act gtt      1584
Leu Leu Val Pro Phe Val Gln Trp Phe Val Gly Leu Ser Pro Thr Val
        515                 520                 525 tgg ctt tca gct ata tgg atg atg tgg tat tgg ggg cca agt ctg tac      1632
Trp Leu Ser Ala Ile Trp Met Met Trp Tyr Trp Gly Pro Ser Leu Tyr
    530                 535                 540 agc atc gtg agt ccc ttt ata ccg ctg tta cca att ttc ttt tgt ctc      1680
Ser Ile Val Ser Pro Phe Ile Pro Leu Leu Pro Ile Phe Phe Cys Leu
545                 550                 555                 560 tgg gta tac att taa                                                  1695
Trp Val Tyr Ile <210> SEQ ID NO 10
<211> LENGTH: 564
<212> TYPE: PRT
<213> ORGANISM: Artificial Sequence
<220> FEATURE:
<223> OTHER INFORMATION: Synthetic Construct

<400> SEQUENCE: 10

Glu Thr Tyr Thr Thr Gly Gly Ser Ile Ala Lys Thr Val Gln Gly Phe
1               5                   10                  15

Thr Ser Phe Phe Thr Pro Gly Ala Lys Gln Asp Ile Gln Leu Ile Asn
            20                  25                  30

Thr Asn Gly Ser Trp His Ile Asn Arg Thr Ala Leu Asn Cys Asn Ala
        35                  40                  45

Ser Leu Glu Thr Gly Trp Ile Ala Gly Leu Phe Tyr Tyr Asn Lys Phe
    50                  55                  60

Asn Ser Ser Gly Cys Pro Glu Arg Met Ala Ser Cys Lys Pro Leu Ala
65                  70                  75                  80

Tyr Phe Ala Gln Gly Trp Gly Pro Ile Ser His Val Asn Gly Ser Gly
                85                  90                  95

Pro Glu Gln Arg Pro Tyr Cys Trp His Tyr Ala Pro Arg Pro Cys Gly
            100                 105                 110

Ile Val Ser Ala Gln Thr Val Cys Gly Pro Val Tyr Cys Phe Thr Pro
        115                 120                 125
```

-continued

```
Ser Pro Val Val Gly Thr Thr Asp Lys Leu Gly Ala Pro Thr Tyr
130                 135                 140

Asn Trp Gly Glu Asn Asp Thr Asp Val Phe Val Leu Asn Asn Thr Arg
145                 150                 155                 160

Pro Pro Leu Gly Asn Trp Phe Gly Cys Thr Trp Met Asn Ser Ser Gly
                165                 170                 175

Phe Thr Lys Val Cys Gly Ala Pro Cys Ala Ile Gly Val Gly
                180                 185                 190

Asn Asn Thr Leu Arg Cys Pro Thr Asp Cys Phe Arg Lys His Pro Glu
                195                 200                 205

Ala Thr Tyr Ser Arg Cys Gly Ser Gly Pro Trp Ile Thr Pro Arg Cys
210                 215                 220

Leu Val Asp Tyr Pro Tyr Arg Leu Trp His Tyr Pro Cys Thr Val Asn
225                 230                 235                 240

Tyr Thr Leu Phe Lys Ile Arg Met Tyr Val Gly Gly Val Glu His Arg
                245                 250                 255

Leu Gln Ala Ala Cys Asn Trp Thr Arg Gly Glu Arg Cys Asp Leu Asp
                260                 265                 270

Asp Arg Asp Arg Ser Glu Leu Ser Pro Leu Leu Leu Ser Thr Thr Gln
                275                 280                 285

Trp Gln Val Leu Pro Cys Ser Phe Thr Thr Leu Pro Ala Leu Thr Thr
290                 295                 300

Gly Leu Ile His Leu His Gln Asn Ile Val Asp Val Gln Tyr Leu Tyr
305                 310                 315                 320

Gly Val Gly Ser Ser Ile Val Ser Trp Ala Ile Lys Trp Glu Tyr Val
                325                 330                 335

Ile Leu Leu Phe Leu Leu Leu Ala Asp Ala Arg Ile Cys Ser Cys Leu
                340                 345                 350

Trp Met Met Leu Leu Ile Ser Gln Thr Arg Ile Leu Thr Ile Pro Gln
                355                 360                 365

Ser Leu Asp Ser Trp Trp Thr Ser Leu Asn Phe Leu Gly Gly Ser Pro
                370                 375                 380

Val Cys Leu Gly Gln Asn Ser Gln Ser Pro Thr Ser Asn His Ser Pro
385                 390                 395                 400

Thr Ser Cys Pro Pro Ile Cys Pro Gly Tyr Arg Trp Met Cys Leu Arg
                405                 410                 415

Arg Phe Ile Ile Phe Leu Phe Ile Leu Leu Leu Cys Leu Ile Phe Leu
                420                 425                 430

Leu Val Leu Leu Asp Tyr Gln Gly Met Leu Pro Val Cys Pro Leu Ile
                435                 440                 445

Pro Gly Ser Thr Thr Thr Ser Thr Gly Pro Cys Lys Thr Cys Thr Thr
450                 455                 460

Pro Ala Gln Gly Asn Ser Met Phe Pro Ser Cys Cys Cys Thr Lys Pro
465                 470                 475                 480

Thr Asp Gly Asn Cys Thr Cys Ile Pro Ile Pro Ser Ser Trp Ala Phe
                485                 490                 495

Ala Lys Tyr Leu Trp Glu Trp Ala Ser Val Arg Phe Ser Trp Leu Ser
                500                 505                 510

Leu Leu Val Pro Phe Val Gln Trp Phe Val Gly Leu Ser Pro Thr Val
                515                 520                 525

Trp Leu Ser Ala Ile Trp Met Met Trp Tyr Trp Gly Pro Ser Leu Tyr
530                 535                 540
```

```
Ser Ile Val Ser Pro Phe Ile Pro Leu Leu Pro Ile Phe Phe Cys Leu
545                 550                 555                 560

Trp Val Tyr Ile

<210> SEQ ID NO 11
<211> LENGTH: 1263
<212> TYPE: DNA
<213> ORGANISM: Artificial Sequence
<220> FEATURE:
<223> OTHER INFORMATION: derived from HCV and HBV
<220> FEATURE:
<221> NAME/KEY: CDS
<222> LOCATION: (1)..(1263)

<400> SEQUENCE: 11 atg aca ggg aac ctt cct ggt tgc tct ttc tct atc ttc ctt ctg gcc      48
Met Thr Gly Asn Leu Pro Gly Cys Ser Phe Ser Ile Phe Leu Leu Ala
1               5                   10                  15 ctg ctc tct tgc ctg act gtg ccc gcg tca gcc tac caa gta cgc aac      96
Leu Leu Ser Cys Leu Thr Val Pro Ala Ser Ala Tyr Gln Val Arg Asn
            20                  25                  30 tcc tcg ggc ctt tac cat gtc acc aat gat tgc cct aac tcg agt att     144
Ser Ser Gly Leu Tyr His Val Thr Asn Asp Cys Pro Asn Ser Ser Ile
        35                  40                  45 gtg tac gag acg gcc gat acc atc cta cac tct ccg ggg tgt gtc cct     192
Val Tyr Glu Thr Ala Asp Thr Ile Leu His Ser Pro Gly Cys Val Pro
    50                  55                  60 tgc gtt cgc gag ggc aat gcc tca aaa tgt tgg gta gcg gtg gcc cct     240
Cys Val Arg Glu Gly Asn Ala Ser Lys Cys Trp Val Ala Val Ala Pro
65                  70                  75                  80 aca gtc gcc acc aga gac ggc aag ctc ccc aca acg cag ctt cga cgt     288
Thr Val Ala Thr Arg Asp Gly Lys Leu Pro Thr Thr Gln Leu Arg Arg
                85                  90                  95 cac atc gat ctg ctc gtc agg agc gcc acc ctc tgc tcg gcc ctc tat     336
His Ile Asp Leu Leu Val Arg Ser Ala Thr Leu Cys Ser Ala Leu Tyr
            100                 105                 110 gtg ggg gac ttg tgc ggg tcc gtc ttc ctc gtc ggt caa ctg ttc acc     384
Val Gly Asp Leu Cys Gly Ser Val Phe Leu Val Gly Gln Leu Phe Thr
        115                 120                 125 ttc tcc ccc agg cgc cac tgg aca acg caa gac tgc aac tgt tcc atg     432
Phe Ser Pro Arg Arg His Trp Thr Thr Gln Asp Cys Asn Cys Ser Met
    130                 135                 140 tac ccc ggc cat ata acg ggt cac cgt atg gca tgg gac atg atg atg     480
Tyr Pro Gly His Ile Thr Gly His Arg Met Ala Trp Asp Met Met Met
145                 150                 155                 160 aac tgg tcc cct acg aca gcg ctg gta gta gct cag ctg ctc agg gtc     528
Asn Trp Ser Pro Thr Thr Ala Leu Val Val Ala Gln Leu Leu Arg Val
                165                 170                 175 ccg caa gcc atc ttg gac atg atc gct ggt gcc cac tgg gga gtc cta     576
Pro Gln Ala Ile Leu Asp Met Ile Ala Gly Ala His Trp Gly Val Leu
            180                 185                 190 gcg ggc ata gcg tat ttc tcc atg gtg ggg aac tgg gcg aag gtc ctg     624
Ala Gly Ile Ala Tyr Phe Ser Met Val Gly Asn Trp Ala Lys Val Leu
        195                 200                 205 gtg gtg ctg ttg ctg ttc gcc agc aca aga atc ctc aca ata ccg cag     672
Val Val Leu Leu Leu Phe Ala Ser Thr Arg Ile Leu Thr Ile Pro Gln
    210                 215                 220 agt cta gac tcg tgg tgg act tct ctc aat ttt cta ggg gga tct ccc     720
Ser Leu Asp Ser Trp Trp Thr Ser Leu Asn Phe Leu Gly Gly Ser Pro
225                 230                 235                 240 gtg tgt ctt ggc caa aat tcg cag tcc cca acc tcc aat cac tca cca     768
```

```
                Val Cys Leu Gly Gln Asn Ser Gln Ser Pro Thr Ser Asn His Ser Pro
                                245                 250                 255 acc tcc tgt cct cca att tgt cct ggt tat cgc tgg atg tgt ctg cgg          816
Thr Ser Cys Pro Pro Ile Cys Pro Gly Tyr Arg Trp Met Cys Leu Arg
            260                 265                 270 cgt ttt atc ata ttc ctc ttc atc ctg ctg cta tgc ctc atc ttc tta          864
Arg Phe Ile Ile Phe Leu Phe Ile Leu Leu Leu Cys Leu Ile Phe Leu
        275                 280                 285 ttg gtt ctt ctg gat tat caa ggt atg ttg ccc gtt tgt cct cta att          912
Leu Val Leu Leu Asp Tyr Gln Gly Met Leu Pro Val Cys Pro Leu Ile
    290                 295                 300 cca gga tca aca aca acc agt acg gga cca tgc aaa acc tgc acg act          960
Pro Gly Ser Thr Thr Thr Ser Thr Gly Pro Cys Lys Thr Cys Thr Thr
305                 310                 315                 320 cct gct caa ggc aac tct atg ttt ccc tca tgt tgc tgt aca aaa cct         1008
Pro Ala Gln Gly Asn Ser Met Phe Pro Ser Cys Cys Cys Thr Lys Pro
                325                 330                 335 acg gat gga aat tgc acc tgt att ccc atc cca tcg tcc tgg gct ttc         1056
Thr Asp Gly Asn Cys Thr Cys Ile Pro Ile Pro Ser Ser Trp Ala Phe
            340                 345                 350 gca aaa tac cta tgg gag tgg gcc tca gtc cgt ttc tct tgg ctc agt         1104
Ala Lys Tyr Leu Trp Glu Trp Ala Ser Val Arg Phe Ser Trp Leu Ser
        355                 360                 365 tta cta gtg cca ttt gtt cag tgg ttc gta ggg ctt tcc ccc act gtt         1152
Leu Leu Val Pro Phe Val Gln Trp Phe Val Gly Leu Ser Pro Thr Val
    370                 375                 380 tgg ctt tca gct ata tgg atg atg tgg tat tgg ggg cca agt ctg tac         1200
Trp Leu Ser Ala Ile Trp Met Met Trp Tyr Trp Gly Pro Ser Leu Tyr
385                 390                 395                 400 agc atc gtg agt ccc ttt ata ccg ctg tta cca att ttc ttt tgt ctc         1248
Ser Ile Val Ser Pro Phe Ile Pro Leu Leu Pro Ile Phe Phe Cys Leu
                405                 410                 415 tgg gta tac att taa                                                     1263
Trp Val Tyr Ile
            420

<210> SEQ ID NO 12
<211> LENGTH: 420
<212> TYPE: PRT
<213> ORGANISM: Artificial Sequence
<220> FEATURE:
<223> OTHER INFORMATION: Synthetic Construct

<400> SEQUENCE: 12

Met Thr Gly Asn Leu Pro Gly Cys Ser Phe Ser Ile Phe Leu Leu Ala
1               5                   10                  15

Leu Leu Ser Cys Leu Thr Val Pro Ala Ser Ala Tyr Gln Val Arg Asn
                20                  25                  30

Ser Ser Gly Leu Tyr His Val Thr Asn Asp Cys Pro Asn Ser Ser Ile
            35                  40                  45

Val Tyr Glu Thr Ala Asp Thr Ile Leu His Ser Pro Gly Cys Val Pro
        50                  55                  60

Cys Val Arg Glu Gly Asn Ala Ser Lys Cys Trp Val Ala Val Ala Pro
65                  70                  75                  80

Thr Val Ala Thr Arg Asp Gly Lys Leu Pro Thr Thr Gln Leu Arg Arg
                85                  90                  95

His Ile Asp Leu Leu Val Arg Ser Ala Thr Leu Cys Ser Ala Leu Tyr
            100                 105                 110

Val Gly Asp Leu Cys Gly Ser Val Phe Leu Val Gly Gln Leu Phe Thr
```

```
            115                 120                 125
Phe Ser Pro Arg Arg His Trp Thr Thr Gln Asp Cys Asn Cys Ser Met
        130                 135                 140
Tyr Pro Gly His Ile Thr Gly His Arg Met Ala Trp Asp Met Met Met
145                 150                 155                 160
Asn Trp Ser Pro Thr Thr Ala Leu Val Val Ala Gln Leu Leu Arg Val
                165                 170                 175
Pro Gln Ala Ile Leu Asp Met Ile Ala Gly Ala His Trp Gly Val Leu
            180                 185                 190
Ala Gly Ile Ala Tyr Phe Ser Met Val Gly Asn Trp Ala Lys Val Leu
        195                 200                 205
Val Val Leu Leu Leu Phe Ala Ser Thr Arg Ile Leu Thr Ile Pro Gln
    210                 215                 220
Ser Leu Asp Ser Trp Trp Thr Ser Leu Asn Phe Leu Gly Gly Ser Pro
225                 230                 235                 240
Val Cys Leu Gly Gln Asn Ser Gln Ser Pro Thr Ser Asn His Ser Pro
                245                 250                 255
Thr Ser Cys Pro Pro Ile Cys Pro Gly Tyr Arg Trp Met Cys Leu Arg
            260                 265                 270
Arg Phe Ile Ile Phe Leu Phe Ile Leu Leu Leu Cys Leu Ile Phe Leu
        275                 280                 285
Leu Val Leu Leu Asp Tyr Gln Gly Met Leu Pro Val Cys Pro Leu Ile
    290                 295                 300
Pro Gly Ser Thr Thr Thr Ser Thr Gly Pro Cys Lys Thr Cys Thr Thr
305                 310                 315                 320
Pro Ala Gln Gly Asn Ser Met Phe Pro Ser Cys Cys Thr Lys Pro
                325                 330                 335
Thr Asp Gly Asn Cys Thr Cys Ile Pro Ile Pro Ser Ser Trp Ala Phe
            340                 345                 350
Ala Lys Tyr Leu Trp Glu Trp Ala Ser Val Arg Phe Ser Trp Leu Ser
        355                 360                 365
Leu Leu Val Pro Phe Val Gln Trp Phe Val Gly Leu Ser Pro Thr Val
    370                 375                 380
Trp Leu Ser Ala Ile Trp Met Met Trp Tyr Trp Gly Pro Ser Leu Tyr
385                 390                 395                 400
Ser Ile Val Ser Pro Phe Ile Pro Leu Leu Pro Ile Phe Phe Cys Leu
                405                 410                 415
Trp Val Tyr Ile
        420

<210> SEQ ID NO 13
<211> LENGTH: 1752
<212> TYPE: DNA
<213> ORGANISM: Artificial Sequence
<220> FEATURE:
<223> OTHER INFORMATION: derived from HCV and HBV
<220> FEATURE:
<221> NAME/KEY: CDS
<222> LOCATION: (1)..(1752)

<400> SEQUENCE: 13 atg ggg aac tgg gcg aag gtc ctg gtg gtg ctg ttg ctg ttc gcc agc    48
Met Gly Asn Trp Ala Lys Val Leu Val Val Leu Leu Leu Phe Ala Ser
1               5                   10                  15 gtc gat gcg gaa acc tac acc acc ggg ggg agt att gcc aaa acc gtg    96
Val Asp Ala Glu Thr Tyr Thr Thr Gly Gly Ser Ile Ala Lys Thr Val
            20                  25                  30
```

```
caa gga ttc acc agt ttt ttt acc cca ggc gcc aag cag gac atc cag    144
Gln Gly Phe Thr Ser Phe Phe Thr Pro Gly Ala Lys Gln Asp Ile Gln
        35                  40                  45 ctg atc aac acc aac ggc agt tgg cac atc aat cgc acg gcc ttg aac    192
Leu Ile Asn Thr Asn Gly Ser Trp His Ile Asn Arg Thr Ala Leu Asn
 50                  55                  60 tgt aat gcg agc ctc gaa acc ggc tgg ata gcg ggg ctc ttc tac tac    240
Cys Asn Ala Ser Leu Glu Thr Gly Trp Ile Ala Gly Leu Phe Tyr Tyr
65                  70                  75                  80 aac aaa ttc aac tcc tca ggc tgc ccc gag agg atg gcc agc tgc aaa    288
Asn Lys Phe Asn Ser Ser Gly Cys Pro Glu Arg Met Ala Ser Cys Lys
                 85                  90                  95 ccc ctt gcc tat ttc gcc caa ggc tgg ggc cct atc agc cat gtc aac    336
Pro Leu Ala Tyr Phe Ala Gln Gly Trp Gly Pro Ile Ser His Val Asn
                100                 105                 110 gga agc ggc ccc gaa cag cgc ccc tac tgc tgg cac tac gcc cca agg    384
Gly Ser Gly Pro Glu Gln Arg Pro Tyr Cys Trp His Tyr Ala Pro Arg
            115                 120                 125 cct tgt ggt atc gtg tca gca cag aca gta tgt ggc cca gtg tat tgt    432
Pro Cys Gly Ile Val Ser Ala Gln Thr Val Cys Gly Pro Val Tyr Cys
        130                 135                 140 ttc act cct agc ccc gtg gtg gtg ggg acg acc gac aag ttg ggc gcg    480
Phe Thr Pro Ser Pro Val Val Val Gly Thr Thr Asp Lys Leu Gly Ala
145                 150                 155                 160 cct acc tac aac tgg ggt gag aat gat acg gac gtc ttc gtc ctc aat    528
Pro Thr Tyr Asn Trp Gly Glu Asn Asp Thr Asp Val Phe Val Leu Asn
                165                 170                 175 aac acc agg cca ccg ttg ggc aat tgg ttc ggt tgc acc tgg atg aac    576
Asn Thr Arg Pro Pro Leu Gly Asn Trp Phe Gly Cys Thr Trp Met Asn
                180                 185                 190 tca tct gga ttc acc aaa gtg tgc gga gcg cct ccc tgt gcc atc gga    624
Ser Ser Gly Phe Thr Lys Val Cys Gly Ala Pro Pro Cys Ala Ile Gly
            195                 200                 205 gga gtg ggc aat aac acc ttg cgc tgt ccc act gac tgt ttc cgc aag    672
Gly Val Gly Asn Asn Thr Leu Arg Cys Pro Thr Asp Cys Phe Arg Lys
        210                 215                 220 cat ccg gaa gct aca tac tct cga tgt ggc tcc ggt ccc tgg atc acg    720
His Pro Glu Ala Thr Tyr Ser Arg Cys Gly Ser Gly Pro Trp Ile Thr
225                 230                 235                 240 ccc agg tgc ctg gtc gac tat cct tat agg ctc tgg cat tat cct tgc    768
Pro Arg Cys Leu Val Asp Tyr Pro Tyr Arg Leu Trp His Tyr Pro Cys
                245                 250                 255 act gtc aac tac acc ctg ttt aaa atc agg atg tac gtg gga ggg gtc    816
Thr Val Asn Tyr Thr Leu Phe Lys Ile Arg Met Tyr Val Gly Gly Val
                260                 265                 270 gag cac agg cta caa gct gct tgc aac tgg acg cgg ggc gag cgt tgt    864
Glu His Arg Leu Gln Ala Ala Cys Asn Trp Thr Arg Gly Glu Arg Cys
            275                 280                 285 gat ctg gac gac agg gac agg tcc gag ctc agc ccg ctg ctg ctg tcc    912
Asp Leu Asp Asp Arg Asp Arg Ser Glu Leu Ser Pro Leu Leu Leu Ser
        290                 295                 300 acc acg cag tgg cag gtc ctt ccg tgt tct ttc acg acc ttg cca gcc    960
Thr Thr Gln Trp Gln Val Leu Pro Cys Ser Phe Thr Thr Leu Pro Ala
305                 310                 315                 320 ttg acc acc ggc ctc atc cac ctc cat cag aac atc gtg gac gtg caa    1008
Leu Thr Thr Gly Leu Ile His Leu His Gln Asn Ile Val Asp Val Gln
                325                 330                 335 tat ttg tac ggg gtg ggg tca agc att gtg tcc tgg gcc atc aag tgg    1056
Tyr Leu Tyr Gly Val Gly Ser Ser Ile Val Ser Trp Ala Ile Lys Trp
```

```
gag tac gtc att ctc ttg ttt ctc ctg ctt gca gac gcg cgc atc tgc    1104
Glu Tyr Val Ile Leu Leu Phe Leu Leu Leu Ala Asp Ala Arg Ile Cys
        355                 360                 365 tcc tgc ttg tgg atg atg cta ctc ata tcc caa aca aga atc ctc aca    1152
Ser Cys Leu Trp Met Met Leu Leu Ile Ser Gln Thr Arg Ile Leu Thr
370                 375                 380 ata ccg cag agt cta gac tcg tgg tgg act tct ctc aat ttt cta ggg    1200
Ile Pro Gln Ser Leu Asp Ser Trp Trp Thr Ser Leu Asn Phe Leu Gly
385                 390                 395                 400 gga tct ccc gtg tgt ctt ggc caa aat tcg cag tcc cca acc tcc aat    1248
Gly Ser Pro Val Cys Leu Gly Gln Asn Ser Gln Ser Pro Thr Ser Asn
                405                 410                 415 cac tca cca acc tcc tgt cct cca att tgt cct ggt tat cgc tgg atg    1296
His Ser Pro Thr Ser Cys Pro Pro Ile Cys Pro Gly Tyr Arg Trp Met
            420                 425                 430 tgt ctg cgg cgt ttt atc ata ttc ctc ttc atc ctg ctg cta tgc ctc    1344
Cys Leu Arg Arg Phe Ile Ile Phe Leu Phe Ile Leu Leu Leu Cys Leu
        435                 440                 445 atc ttc tta ttg gtt ctt ctg gat tat caa ggt atg ttg ccc gtt tgt    1392
Ile Phe Leu Leu Val Leu Leu Asp Tyr Gln Gly Met Leu Pro Val Cys
450                 455                 460 cct cta att cca gga tca aca aca acc agt acg gga cca tgc aaa acc    1440
Pro Leu Ile Pro Gly Ser Thr Thr Thr Ser Thr Gly Pro Cys Lys Thr
465                 470                 475                 480 tgc acg act cct gct caa ggc aac tct atg ttt ccc tca tgt tgc tgt    1488
Cys Thr Thr Pro Ala Gln Gly Asn Ser Met Phe Pro Ser Cys Cys Cys
                485                 490                 495 aca aaa cct acg gat gga aat tgc acc tgt att ccc atc cca tcg tcc    1536
Thr Lys Pro Thr Asp Gly Asn Cys Thr Cys Ile Pro Ile Pro Ser Ser
            500                 505                 510 tgg gct ttc gca aaa tac cta tgg gag tgg gcc tca gtc cgt ttc tct    1584
Trp Ala Phe Ala Lys Tyr Leu Trp Glu Trp Ala Ser Val Arg Phe Ser
        515                 520                 525 tgg ctc agt tta cta gtg cca ttt gtt cag tgg ttc gta ggg ctt tcc    1632
Trp Leu Ser Leu Leu Val Pro Phe Val Gln Trp Phe Val Gly Leu Ser
530                 535                 540 ccc act gtt tgg ctt tca gct ata tgg atg atg tgg tat tgg ggg cca    1680
Pro Thr Val Trp Leu Ser Ala Ile Trp Met Met Trp Tyr Trp Gly Pro
545                 550                 555                 560 agt ctg tac agc atc gtg agt ccc ttt ata ccg ctg tta cca att ttc    1728
Ser Leu Tyr Ser Ile Val Ser Pro Phe Ile Pro Leu Leu Pro Ile Phe
                565                 570                 575 ttt tgt ctc tgg gta tac att taa                                    1752
Phe Cys Leu Trp Val Tyr Ile
            580

<210> SEQ ID NO 14
<211> LENGTH: 583
<212> TYPE: PRT
<213> ORGANISM: Artificial Sequence
<220> FEATURE:
<223> OTHER INFORMATION: Synthetic Construct

<400> SEQUENCE: 14

Met Gly Asn Trp Ala Lys Val Leu Val Val Leu Leu Phe Ala Ser
1               5                   10                  15

Val Asp Ala Glu Thr Tyr Thr Thr Gly Gly Ser Ile Ala Lys Thr Val
            20                  25                  30

Gln Gly Phe Thr Ser Phe Phe Thr Pro Gly Ala Lys Gln Asp Ile Gln
```

```
                35                  40                  45
Leu Ile Asn Thr Asn Gly Ser Trp His Ile Asn Arg Thr Ala Leu Asn
 50                  55                  60
Cys Asn Ala Ser Leu Glu Thr Gly Trp Ile Ala Gly Leu Phe Tyr Tyr
 65                  70                  75                  80
Asn Lys Phe Asn Ser Ser Gly Cys Pro Glu Arg Met Ala Ser Cys Lys
                 85                  90                  95
Pro Leu Ala Tyr Phe Ala Gln Gly Trp Gly Pro Ile Ser His Val Asn
                100                 105                 110
Gly Ser Gly Pro Glu Gln Arg Pro Tyr Cys Trp His Tyr Ala Pro Arg
                115                 120                 125
Pro Cys Gly Ile Val Ser Ala Gln Thr Val Cys Gly Pro Val Tyr Cys
                130                 135                 140
Phe Thr Pro Ser Pro Val Val Val Gly Thr Thr Asp Lys Leu Gly Ala
145                 150                 155                 160
Pro Thr Tyr Asn Trp Gly Glu Asn Asp Thr Asp Val Phe Val Leu Asn
                165                 170                 175
Asn Thr Arg Pro Pro Leu Gly Asn Trp Phe Gly Cys Thr Trp Met Asn
                180                 185                 190
Ser Ser Gly Phe Thr Lys Val Cys Gly Ala Pro Pro Cys Ala Ile Gly
                195                 200                 205
Gly Val Gly Asn Asn Thr Leu Arg Cys Pro Thr Asp Cys Phe Arg Lys
210                 215                 220
His Pro Glu Ala Thr Tyr Ser Arg Cys Gly Ser Gly Pro Trp Ile Thr
225                 230                 235                 240
Pro Arg Cys Leu Val Asp Tyr Pro Tyr Arg Leu Trp His Tyr Pro Cys
                245                 250                 255
Thr Val Asn Tyr Thr Leu Phe Lys Ile Arg Met Tyr Val Gly Gly Val
                260                 265                 270
Glu His Arg Leu Gln Ala Ala Cys Asn Trp Thr Arg Gly Glu Arg Cys
                275                 280                 285
Asp Leu Asp Asp Arg Asp Arg Ser Glu Leu Ser Pro Leu Leu Leu Ser
                290                 295                 300
Thr Thr Gln Trp Gln Val Leu Pro Cys Ser Phe Thr Thr Leu Pro Ala
305                 310                 315                 320
Leu Thr Thr Gly Leu Ile His Leu His Gln Asn Ile Val Asp Val Gln
                325                 330                 335
Tyr Leu Tyr Gly Val Gly Ser Ser Ile Val Ser Trp Ala Ile Lys Trp
                340                 345                 350
Glu Tyr Val Ile Leu Leu Phe Leu Leu Leu Ala Asp Ala Arg Ile Cys
                355                 360                 365
Ser Cys Leu Trp Met Met Leu Leu Ile Ser Gln Thr Arg Ile Leu Thr
                370                 375                 380
Ile Pro Gln Ser Leu Asp Ser Trp Trp Thr Ser Leu Asn Phe Leu Gly
385                 390                 395                 400
Gly Ser Pro Val Cys Leu Gly Gln Asn Ser Gln Ser Pro Thr Ser Asn
                405                 410                 415
His Ser Pro Thr Ser Cys Pro Pro Ile Cys Pro Gly Tyr Arg Trp Met
                420                 425                 430
Cys Leu Arg Arg Phe Ile Ile Phe Leu Phe Ile Leu Leu Leu Cys Leu
                435                 440                 445
Ile Phe Leu Leu Val Leu Leu Asp Tyr Gln Gly Met Leu Pro Val Cys
450                 455                 460
```

```
Pro Leu Ile Pro Gly Ser Thr Thr Ser Thr Gly Pro Cys Lys Thr
465                 470                 475                 480

Cys Thr Thr Pro Ala Gln Gly Asn Ser Met Phe Pro Ser Cys Cys Cys
                485                 490                 495

Thr Lys Pro Thr Asp Gly Asn Cys Thr Cys Ile Pro Ile Pro Ser Ser
            500                 505                 510

Trp Ala Phe Ala Lys Tyr Leu Trp Glu Trp Ala Ser Val Arg Phe Ser
                515                 520                 525

Trp Leu Ser Leu Leu Val Pro Phe Val Gln Trp Phe Val Gly Leu Ser
            530                 535                 540

Pro Thr Val Trp Leu Ser Ala Ile Trp Met Met Trp Tyr Trp Gly Pro
545                 550                 555                 560

Ser Leu Tyr Ser Ile Val Ser Pro Phe Ile Pro Leu Leu Pro Ile Phe
                565                 570                 575

Phe Cys Leu Trp Val Tyr Ile
            580

<210> SEQ ID NO 15
<211> LENGTH: 10855
<212> TYPE: DNA
<213> ORGANISM: Artificial Sequence
<220> FEATURE:
<223> OTHER INFORMATION: Lentivirus containing the sequences derived
      from HCV and HBV

<400> SEQUENCE: 15
ttaattccgt gtattctata gtgtcaccta atcgtatgt gtatgataca taaggttatg      60
tattaattgt agccgcgttc taacgacaat atgtacaagc ctaattgtgt agcatctggc    120
ttactgaagc agaccctatc atctctctcg taaactgccg tcagagtcgg tttggttgga    180
cgaaccttct gagtttctgg taacgccgtc ccgcacccgg aaatggtcag cgaaccaatc    240
agcagggtca tcgctagcca gatcctctac gccggacgca tcgtggccgg catcaccggc    300
gccacaggtg cggttgctgg cgcctatatc gccgacatca ccgatgggga agatcgggct    360
cgccacttcg gctcatgag cgcttgtttc ggcgtgggta tggtggcagg ccccgtggcc     420
gggggactgt gggcgccat ctccttgcat gcaccattcc ttgcggcggc ggtgctcaac     480
ggcctcaacc tactactggg ctgcttccta atgcaggagt cgcataaggg agagcgtcga    540
atggtgcact ctcagtacaa tctgctctga tgccgcatag ttaagccagc cccgacaccc    600
gccaacaccc gctgacgcgc cctgacgggc ttgtctgctc ccggcatccg cttacagaca    660
agctgtgacc gtctccggga gctgcatgtg tcagaggttt tcaccgtcat caccgaaacg    720
cgcgagacga agggcctcg tgatacgcct attttatag gttaatgtca tgataataat     780
ggtttcttag acgtcaggtg cacttttcg gggaaatgtg cgcggaaccc ctatttgttt     840
attttcctaa atacattcaa atatgtatcc gctcatgaga caataaccct gataaatgct    900
tcaataatat tgaaaaagga agagtatgag tattcaacat ttccgtgtcg cccttattcc    960 ctttttttgcg gcattttgcc ttcctgtttt tgctcaccca gaaacgctgg tgaaagtaaa   1020
agatgctgaa gatcagttgg gtgcacgagt gggttacatc gaactggatc tcaacagcgg   1080
taagatcctt gagagttttc gccccgaaga acgttttcca atgatgagca cttttaaagt   1140
tctgctatgt ggcgcggtat tatcccgtat tgacgccggg caagagcaac tcggtcgccg   1200
catacactat tctcagaatg acttggttga gtactcacca gtcacagaaa agcatcttac   1260
ggatggcatg acagtaagag aattatgcag tgctgccata accatgagtg ataacactgc   1320
```

```
ggccaactta cttctgacaa cgatcggagg accgaaggag ctaaccgctt ttttgcacaa    1380 catggggat catgtaactc gccttgatcg ttgggaaccg gagctgaatg aagccatacc     1440
aaacgacgag cgtgacacca cgatgcctgt agcaatggca acaacgttgc gcaaactatt    1500
aactggcgaa ctacttactc tagcttcccg gcaacaatta atagactgga tggaggcgga    1560
taaagttgca ggaccacttc tgcgctcggc ccttccggct ggctggttta ttgctgataa    1620
atctggagcc ggtgagcgtg ggtctcgcgg tatcattgca gcactgggc cagatggtaa    1680 gccctcccgt atcgtagtta tctacacgac ggggagtcag gcaactatgg atgaacgaaa    1740
tagacagatc gctgagatag gtgcctcact gattaagcat tggtaactgt cagaccaagt    1800
ttactcatat atactttaga ttgatttaaa acttcatttt taatttaaaa ggatctaggt    1860
gaagatcctt tttgataatc tcatgaccaa aatcccttaa cgtgagtttt cgttccactg    1920
agcgtcagac cccgtagaaa agatcaaagg atcttcttga gatccttttt ttctgcgcgt    1980
aatctgctgc ttgcaaacaa aaaaaccacc gctaccagcg gtggtttgtt tgccggatca    2040
agagctacca actcttttc cgaaggtaac tggcttcagc agagcgcaga taccaaatac    2100
tgtccttcta gtgtagccgt agttaggcca ccacttcaag aactctgtag caccgcctac    2160
atacctcgct ctgctaatcc tgttaccagt ggctgctgcc agtggcgata gtcgtgtct    2220 taccggggttg gactcaagac gatagttacc ggataaggcg cagcggtcgg gctgaacggg   2280
gggttcgtgc acacagccca gcttggagcg aacgacctac accgaactga gatacctaca   2340
gcgtgagcat tgagaaagcg ccacgcttcc cgaagggaga aaggcggaca ggtatccggt    2400
aagcggcagg gtcggaacag gagagcgcac gagggagctt ccaggggaa acgcctggta    2460 tctttatagt cctgtcgggt ttcgccacct ctgacttgag cgtcgatttt tgtgatgctc    2520
gtcagggggg cggagcctat ggaaaaacgc cagcaacgcg gcctttttac ggttcctggc    2580
cttttgctgg ccttttgctc acatgttctt cctgcgtta tcccctgatt ctgtggataa    2640
ccgtattacc gcctttgagt gagctgatac cgctcgccgc agccgaacga ccgagcgcag    2700
cgagtcagtg agcgaggaag cggaagagcg cccaatacgc aaaccgcctc tccccgcgcg    2760
ttggccgatt cattaatgca gctgtggaat gtgtgtcagt tagggtgtgg aaagtcccca    2820
ggctccccag caggcagaag tatgcaaagc atgcatctca attagtcagc aaccaggtgt    2880
ggaaagtccc caggctcccc agcaggcaga agtatgcaaa gcatgcatct caattagtca    2940
gcaaccatag tcccgcccct aactccgccc atcccgcccc taactccgcc cagttccgcc    3000
cattctccgc cccatggctg actaattttt tttatttatg cagaggccga ggccgcctcg    3060
gcctctgagc tattccagaa gtagtgagga ggcttttttg gaggcctagg cttttgcaaa    3120
aagcttggac acaagacagg cttgcgagat atgtttgaga ataccacttt atcccgcgtc    3180
agggagaggc agtgcgtaaa aagacgcgga ctcatgtgaa atactggttt ttagtgcgcc    3240
agatctctat aatctcgcgc aacctatttt ccctctgaac actttttaag ccgtagataa    3300
acaggctggg acacttcaca tgagcgaaaa atacatcgtc acctgggaca tgttgcagat    3360
ccatgcacgt aaactcgcaa gccgactgat gccttctgaa caatggaaag gcattattgc    3420
cgtaagccgt ggcggtctgt accgggtgcg ttactggcgc gtgaactggg tattcgtcat    3480
gtcgataccg tttgtatttc cagctacgat cacgacaacc agcgcgagct aaagtgctg    3540 aaacgcgcag aaggcgatgg cgaaggcttc atcgttattg atgacctggt ggataccggt    3600
ggtactgcgg ttgcgattcg tgaaatgtat ccaaaagcgc actttgtcac catcttcgca    3660
```

```
aaaccggctg gtcgtccgct ggttgatgac tatgttgttg atatcccgca agatacctgg   3720
attgaacagc cgtgggatat gggcgtcgta ttcgtcccgc caatctccgg tcgctaatct   3780
tttcaacgcc tggcactgcc gggcgttgtt cttttttaact tcaggcgggt tacaatagtt   3840
tccagtaagt attctggagg ctgcatccat gacacaggca aacctgagcg aaaccctgtt   3900
caaaccccgc tttaaacatc ctgaaacctc gacgctagtc cgccgcttta atcacggcgc   3960
acaaccgcct gtgcagtcgg cccttgatgg taaaaccatc cctcactggt atcgcatgat   4020
taaccgtctg atgtggatct ggcgcggcat tgacccacgc gaaatcctcg acgtccaggc   4080
acgtattgtg atgagcgatg ccgaacgtac cgacgatgat ttatacgata cggtgattgg   4140
ctaccgtggc ggcaactgga tttatgagtg ggccccggat cttgtgaag gaaccttact   4200 tctgtggtgt gacataattg gacaaactac ctacagagat ttaaagctct aaggtaaata   4260 taaaatttt aagtgtataa tgtgttaaac tactgattct aattgtttgt gtattttaga   4320
ttccaaccta tggaactgat gaatgggagc agtggtggaa tgcctttaat gaggaaaacc   4380
tgttttgctc agaagaaatg ccatctagtg atgatgaggc tactgctgac tctcaacatt   4440
ctactcctcc aaaaaagaag agaaaggtag aagacccccaa ggactttcct tcagaattgc   4500 taagttttt gagtcatgct gtgtttagta atagaactct tgcttgcttt gctatttaca   4560
ccacaaagga aaaagctgca ctgctataca agaaaattat ggaaaaatat tctgtaacct   4620
ttataagtag gcataacagt tataatcata acatactgtt ttttcttact ccacacaggc   4680
atagagtgtc tgctattaat aactatgctc aaaaattgtg taccttagc ttttaatttt   4740 gtaaaggggt taataaggaa tatttgatgt atagtgcctt gactagagat cataatcagc   4800
cataccacat ttgtagaggt tttacttgct ttaaaaaacc tcccacacct ccccctgaac   4860
ctgaaacata aaatgaatgc aattgttgtt gttaacttgt ttattgcagc ttataatggt   4920
tacaaataaa gcaatagcat cacaaattc acaaataaag cattttttttc actgcattct   4980 agttgtggtt tgtccaaact catcaatgta tcttatcatg tctggatcaa ctggataact   5040
caagctaacc aaaatcatcc caaacttccc accccatacc ctattaccac tgccaattac   5100
ctagtggttt catttactct aaacctgtga ttcctctgaa ttatttcat tttaaagaaa   5160 ttgtatttgt taaatatgta ctacaaactt agtagttgga agggctaatt cactcccaaa   5220
gaagacaaga tatccttgat ctgtggatct accacacaca aggctacttc cctgattagc   5280
agaactacac accagggcca ggggtcagat atccactgac ctttggatgg tgctacaagc   5340
tagtaccagt tgagccagat aaggtagaag aggccaataa aggagagaac accagcttgt   5400
tacaccctgt gagcctgcat gggatggatg acccggagag agaagtgtta gagtggaggt   5460
ttgacagccg cctagcattt catcacgtgg cccgagagct gcatccggag tacttcaaga   5520
actgctgata tcgagcttgc tacaagggac tttccgctgg ggactttcca gggaggcgtg   5580
gcctgggcgg gactggggag tggcgagccc tcagatcctg catataagca gctgcttttt   5640
gcctgtactg ggtctctctg gttagaccag atctgagcct gggagctctc tggctaacta   5700
gggaacccac tgcttaagcc tcaataaagc ttgccttgag tgcttcaagt agtgtgtgcc   5760
cgtctgttgt gtgactctgg taactagaga tccctcagac ccttttagtc agtgtggaaa   5820
atctctagca gtggcgcccg aacagggact tgaaagcgaa agggaaacca gaggagctct   5880
ctcgacgcag gactcggctt gctgaagcgc gcacggcaag aggcgagggg cggcgactgg   5940
tgagtacgcc aaaaattttg actagcggag gctagaagga gagagatggg tgcgagagcg   6000
tcagtattaa gcgggggaga attagatcgc gatgggaaaa aattcggtta aggccagggg   6060
```

```
gaaagaaaaa atataaatta aaacatatag tatgggcaag cagggagcta gaacgattcg    6120
cagttaatcc tggcctgtta gaaacatcag aaggctgtag acaaatactg ggacagctac    6180
aaccatccct tcagacagga tcagaagaac ttagatcatt atataataca gtagcaaccc    6240
tctattgtgt gcatcaaagg atagagataa aagcaccaa ggaagcttta gacaagatag     6300
aggaagagca aaacaaaagt aagaccaccg cacagcaagc ggccgctgat cttcagacct    6360
ggaggaggag atatgaggga caattggaga agtgaattat ataaatataa agtagtaaaa    6420
attgaaccat taggagtagc acccaccaag gcaaagagaa gagtggtgca gagagaaaaa    6480
agagcagtgg gaataggagc tttgttcctt gggttcttgg gagcagcagg aagcactatg    6540
ggcgcagcgt caatgacgct gacggtacag gccagacaat tattgtctgg tatagtgcag    6600
cagcagaaca atttgctgag ggctattgag gcgcaacagc atctgttgca actcacagtc    6660
tggggcatca agcagctcca ggcaagaatc ctggctgtgg aaagatacct aaaggatcaa    6720
cagctcctgg ggatttgggg ttgctctgga aaactcattt gcaccactgc tgtgccttgg    6780
aatgctagtt ggagtaataa atctctggaa cagatttgga atcacacgac ctggatggag    6840
tgggacagag aaattaacaa ttacacaagc ttaatacact ccttaattga agaatcgcaa    6900
aaccagcaag aaaagaatga acaagaatta ttggaattag ataaatgggc aagtttgtgg    6960
aattggttta acataacaaa ttggctgtgg tatataaaat tattcataat gatagtagga    7020
ggcttggtag gtttaagaat agtttttgct gtactttcta tagtgaatag agttaggcag    7080
ggatattcac cattatcgtt tcagacccac ctcccaaccc cgaggggacc cgacaggccc    7140
gaaggaatag aagaagaagg tggagagaga cagagagaca gatccattcg attagtgaac    7200
ggatctcgac ggtatcgccg aattcacaaa tggcagtatt catccacaat tttaaaagaa    7260 aagggggat tggggggtac agtgcagggg aaagaatagt agacataata gcaacagaca    7320
tacaaactaa agaattacaa aaacaaatta caaaaattca aaattttcgg gtttattaca    7380
gggacagcag agatccactt tatcgataag cttgggagtt ccgcgttaca taacttacgg    7440
taaatggccc gcctggctga ccgcccaacg acccccgccc attgacgtca ataatgacgt    7500
atgttcccat agtaacgcca atagggactt tccattgacg tcaatgggtg gagtatttac    7560
ggtaaactgc ccacttggca gtacatcaag tgtatcatat gccaagtacg ccccctattg    7620
acgtcaatga cggtaaatgg cccgcctggc attatgccca gtacatgacc ttacgggact    7680
ttcctacttg gcagtacatc tacgtattag tcatcgctat taccatggtg atgcggtttt    7740
ggcagtacac caatgggcgt ggatagcggt ttgactcacg gggatttcca agtctccacc    7800
ccattgacgt caatgggagt ttgttttggc accaaaatca acgggacttt ccaaaatgtc    7860
gtaacaactc cgccccattg acgcaaatgg gcggtaggcg tgtacggtgg gaggtctata    7920
taagcagagc tcgtttagtg aaccgtcaga tcgcctggag acgccatcca cgctgttttg    7980
acctccatag aagacaccga ctctagctag aggatccatg taccaagtac gcaactcctc    8040
gggcctttac catgtcacca atgattgccc taactcgagt attgtgtacg agacggccga    8100
taccatccta cactctccgg ggtgtgtccc ttgcgttcgc gagggcaatg cctcaaaatg    8160
ttgggtggcg gtggccccta cagtcgccac cagagacgaa agctccccca acgcagctt    8220 tcgacgtcac atcgatctgc tcgtcaggag cgccaccctc tgctcggccc tctatgtggg    8280
ggacttgtgc gggtccgtct tcctcgtcgg tcaactgttc accttctccc ccaggcgcca    8340
ctggacaacg caagactgca actgttccat gtaccccggc catataacgg gtcaccgtat    8400
```

```
ggcatgggac atgatgatga actggtcccc tacgacagcg ctggtagtag ctcagctgct   8460
cagggtcccg caagccatct tggacatgat cgctggtgcc cactggggag tcctagcggg   8520
catagcgtat ttctccatgg tggggaactg ggcgaaggtc ctggtggtgc tgttgctgtt   8580
cgccagcaca agaatcctca caataccgca gagtctagac tcgtggtgga cttctctcaa   8640
ttttctaggg ggatctcccg tgtgtcttgg ccaaaattcg cagtccccaa cctccaatca   8700
ctcaccaacc tcctgtcctc caatttgtcc tggttatcgc tggatgtgtc tgcggcgttt   8760
tatcatattc ctcttcatcc tgctgctatg cctcatcttc ttattggttc ttctggatta   8820
tcaaggtatg ttgcccgttt gtcctctaat tccaggatca acaacaacca gtacgggacc   8880
atgcaaaacc tgcacgactc ctgctcaagg caactctatg tttccctcat gttgctgtac   8940
aaaacctacg gatggaaatt gcacctgtat tcccatccca tcgtcctggg ctttcgcaaa   9000
atacctatgg gagtgggcct cagtccgttt ctcttggctc agtttactag tgccatttgt   9060
tcagtggttc gtagggcttt cccccactgt ttggctttca gctatatgga tgatgtggta   9120
ttggggggcca agtctgtaca gcatcgtgag tcccttatta ccgctgttac caattttctt   9180
ttgtctctgg gtatacattt aataaggatc cggactagta actcgaggcc cctctccctc   9240
cccccccct aacgttactg gccgaagccg cttggaataa ggccggtgtg cgtttgtcta   9300
tatgttattt tccaccatat tgccgtcttt tggcaatgtg agggcccgga aacctggccc   9360
tgtcttcttg acgagcattc ctaggggtct ttccctctc gccaaaggaa tgcaaggtct   9420
gttgaatgtc gtgaaggaag cagttcctct ggaagcttct tgaagacaaa caacgtctgt   9480
agcgacccct tgcaggcagc ggaaccccc acctggcgac aggtgcctct gcggccaaaa   9540
gccacgtgta taagatacac ctgcaaaggc ggcacaaccc cagtgccacg ttgtgagttg   9600
gatagttgtg gaaagagtca aatggctctc ctcaagcgta ttcaacaagg ggctgaagga   9660
tgcccagaag gtacccccatt gtatgggatc tgatctgggg cctcggtaca catgctttac   9720
atgtgtttag tcgaggttaa aaaaacgtct aggcccccg aaccacgggg acgtggtttt   9780
cctttgaaaa acacgatgat aatatggcca caaccatggt gagcaagggc gaggagctgt   9840
tcaccggggt ggtgcccatc ctggtcgagc tggacgcga cgtaaacggc cacaagttca   9900
gcgtgtccgg cgagggcgag ggcgatgcca cctacggcaa gctgaccctg aagttcatct   9960
gcaccaccgg caagctgccc gtgccctggc ccaccctcgt gaccaccctg acctacggcg  10020
tgcagtgctt cagccgctac cccgaccaca tgaagcagca cgacttcttc aagtccgcca  10080
tgcccgaagg ctacgtccag gagcgcacca tcttcttcaa ggacgacggc aactacaaga  10140
cccgcgccga ggtgaagttc gagggcgaca cctggtgaa ccgcatcgag ctgaagggca  10200
tcgacttcaa ggaggacggc aacatcctgg ggcacaagct ggagtacaac tacaacagcc  10260
acaacgtcta tatcatggcc gacaagcaga agaacggcat caaggtgaac ttcaagatcc  10320
gccacaacat cgaggacggc agcgtgcagc tcgccgacca ctaccagcag aacacccca  10380
tcggcgacgg ccccgtgctg ctgcccgaca accactacct gagcacccag tccgccctga  10440
gcaaagaccc caacgagaag cgcgatcaca tggtcctgct ggagttcgtg accgccgccg  10500
ggatcactct cggcatggac gagctgtaca agtaagtcga gggaattcga gctcggtacc  10560
tttaagacca atgacttaca aggcagctgt agatcttagc cacttttaa aagaaaaggg  10620
gggactggaa gggctaattc actcccaacg aagacaagat cttttgctt gtactgggtc  10680
tctctggtta gaccagatct gagcctggga gctctctggc taactaggga acccactgct  10740
taagcctcaa taaagcttgc cttgagtgct tcaagtagtg tgtgcccgtc tgttgtgtga  10800
```

<210> SEQ ID NO 16
<211> LENGTH: 11368
<212> TYPE: DNA
<213> ORGANISM: Artificial Sequence
<220> FEATURE:
<223> OTHER INFORMATION: Lentivirus containing the sequences derived from HCV and HBV

<400> SEQUENCE: 16

```
ttaattccgt gtattctata gtgtcaccta atcgtatgt gtatgataca taaggttatg      60
tattaattgt agccgcgttc taacgacaat atgtacaagc ctaattgtgt agcatctggc    120
ttactgaagc agaccctatc atctctctcg taaactgccg tcagagtcgg tttggttgga    180
cgaaccttct gagtttctgg taacgccgtc ccgcacccgg aaatggtcag cgaaccaatc    240
agcagggtca tcgctagcca gatcctctac gccggacgca tcgtggccgg catcaccggc    300
gccacaggtg cggttgctgg cgcctatatc gccgacatca ccgatgggga agatcgggct    360
cgccacttcg ggctcatgag cgcttgtttc ggcgtgggta tggtggcagg ccccgtggcc    420
gggggactgt tgggcgccat ctccttgcat gcaccattcc ttgcggcggc ggtgctcaac    480
ggcctcaacc tactactggg ctgcttccta atgcaggagt cgcataaggg agagcgtcga    540
atggtgcact ctcagtacaa tctgctctga tgccgcatag ttaagccagc ccgacacccc    600
gccaacaccc gctgacgcgc cctgacgggc ttgtctgctc ccggcatccg cttacagaca    660
agctgtgacc gtctccggga gctgcatgtg tcagaggttt tcaccgtcat caccgaaacg    720
cgcgagacga aagggcctcg tgatacgcct atttttatag gttaatgtca tgataataat    780
ggtttcttag acgtcaggtg cacttttcg gggaaatgtg cgcggaaccc ctatttgttt    840
attttctaa atacattcaa atatgtatcc gctcatgaga caataaccct gataaatgct    900
tcaataatat tgaaaaagga agagtatgag tattcaacat ttccgtgtcg cccttattcc    960
cttttttgcg gcattttgcc ttcctgtttt tgctcaccca gaaacgctgg tgaaagtaaa   1020
agatgctgaa gatcagttgg gtgcacgagt gggttacatc gaactggatc tcaacagcgg   1080
taagatcctt gagagttttc gccccgaaga acgttttcca atgatgagca cttttaaagt   1140
tctgctatgt ggcgcggtat tatcccgtat tgacgccggg caagagcaac tcggtcgccg   1200
catacactat tctcagaatg acttggttga gtactcacca gtcacagaaa agcatcttac   1260
ggatggcatg acagtaagag aattatgcag tgctgccata accatgagtg ataacactgc   1320
ggccaactta cttctgacaa cgatcggagg accgaaggag ctaaccgctt ttttgcacaa   1380
catgggggat catgtaactc gccttgatcg ttgggaaccg gagctgaatg aagccatacc   1440
aaacgacgag cgtgacacca cgatgcctgt agcaatggca acaacgttgc gcaaactatt   1500
aactggcgaa ctacttactc tagcttcccg gcaacaatta atagactgga tggaggcgga   1560
taaagttgca ggaccacttc tgcgctcggc ccttccggct ggctggttta ttgctgataa   1620
atctggagcc ggtgagcgtg ggtctcgcgg tatcattgca gcactggggc cagatggtaa   1680
gccctcccgt atcgtagtta tctacacgac ggggagtcag gcaactatgg atgaacgaaa   1740
tagacagatc gctgagatag gtgcctcact gattaagcat tggtaactgt cagaccaagt   1800
ttactcatat atactttaga ttgatttaaa acttcatttt taatttaaaa ggatctaggt   1860
gaagatcctt tttgataatc tcatgaccaa atcccttaa cgtgagtttt cgttccactg   1920
agcgtcagac cccgtagaaa agatcaaagg atcttcttga tcctttttt tctgcgcgt   1980
```

```
aatctgctgc ttgcaaacaa aaaaaccacc gctaccagcg gtggtttgtt tgccggatca  2040
agagctacca actcttttc cgaaggtaac tggcttcagc agagcgcaga taccaaatac  2100
tgtccttcta gtgtagccgt agttaggcca ccacttcaag aactctgtag caccgcctac  2160
ataccgcgct ctgctaatcc tgttaccagt ggctgctgcc agtggcgata agtcgtgtct  2220 taccggggttg gactcaagac gatagttacc ggataaggcg cagcggtcgg gctgaacggg  2280
gggttcgtgc acacagccca gcttggagcg aacgacctac accgaactga gatacctaca  2340
gcgtgagcat gagaaagcg ccacgcttcc cgaagggaga aggcggaca ggtatccggt  2400 aagcggcagg gtcggaacag gagagcgcac gagggagctt ccaggggaa acgcctggta  2460 tcttttatagt cctgtcgggt ttcgccacct ctgacttgag cgtcgatttt tgtgatgctc  2520 gtcaggggg cggagcctat ggaaaaacgc cagcaacgcg gccttttac ggttcctggc  2580 ctttttgctgg ccttttgctc acatgttctt tcctgcgtta tccctgatt ctgtggataa  2640 ccgtattacc gcctttgagt gagctgatac cgctcgccgc agccgaacga ccgagcgcag  2700
cgagtcagtg agcgaggaag cggaagagcg cccaatacgc aaaccgcctc tccccgcgcg  2760
ttggccgatt cattaatgca gctgtggaat gtgtgtcagt tagggtgtgg aaagtcccca  2820
ggctccccag caggcagaag tatgcaaagc atgcatctca attagtcagc aaccaggtgt  2880
ggaaagtccc caggctcccc agcaggcaga agtatgcaaa gcatgcatct caattagtca  2940
gcaaccatag tcccgcccct aactccgccc atcccgcccc taactccgcc cagttccgcc  3000
cattctccgc cccatggctg actaatttt tttatttatg cagaggccga ggccgcctcg  3060
gcctctgagc tattccagaa gtagtgagga ggcttttttg gaggcctagg cttttgcaaa  3120
aagcttggac acaagacagg cttgcgagat atgtttgaga ataccacttt atcccgcgtc  3180
agggagaggc agtgcgtaaa aagacgcgga ctcatgtgaa atactggttt ttagtgcgcc  3240
agatctctat aatctcgcgc aacctatttt cccctcgaac acttttaag ccgtagataa  3300 acaggctggg acacttcaca tgagcgaaaa atacatcgtc acctgggaca tgttgcagat  3360
ccatgcacgt aaactcgcaa gccgactgat gccttctgaa caatggaaag gcattattgc  3420
cgtaagccgt ggcggtctgt accgggtgcg ttactggcgc gtgaactggg tattcgtcat  3480
gtcgataccg tttgtatttc cagctacgat cacgacaacc agcgcgagct taaagtgctg  3540
aaacgcgcag aaggcgatgg cgaaggcttc atcgttattg atgacctggt ggataccggt  3600
ggtactgcgg ttgcgattcg tgaaatgtat ccaaaagcgc actttgtcac catcttcgca  3660
aaaccggctg gtcgtccgct ggttgatgac tatgttgttg atatcccgca agatacctgg  3720
attgaacagc cgtgggatat gggcgtcgta ttcgtcccgc caatctccgg tcgctaatct  3780
tttcaacgcc tggcactgcc gggcgttgtt cttttaact tcaggcgggt tacaatagtt  3840
tccagtaagt attctggagg ctgcatccat gacacaggca aacctgagcg aaaccctgtt  3900 caaacccgc tttaaacatc ctgaaacctc gacgctagtc cgccgcttta atcacggcgc  3960
acaaccgcct gtgcagtcgg cccttgatgg taaaaccatc cctcactggt atcgcatgat  4020
taaccgtctg atgtggatct ggcgcggcat tgacccacgc gaaatcctcg acgtccaggc  4080
acgtattgtg atgagcgatg ccgaacgtac cgacgatgat ttatacgata cggtgattgg  4140
ctaccgtggc ggcaactgga tttatgagtg ggcccccggat cttttgtgaag gaaccttact  4200 tctgtggtgt gacataattg gacaaactac ctacagagat ttaaagctct aaggtaaata  4260
taaaattttt aagtgtataa tgtgttaaac tactgattct aattgtttgt gtattttaga  4320
```

```
ttccaaccta tggaactgat gaatgggagc agtggtggaa tgcctttaat gaggaaaacc   4380
tgttttgctc agaagaaatg ccatctagtg atgatgaggc tactgctgac tctcaacatt   4440
ctactcctcc aaaaaagaag agaaaggtag aagaccccaa ggactttcct tcagaattgc   4500 taagttttt gagtcatgct gtgtttagta atagaactct tgcttgcttt gctatttaca    4560
ccacaaagga aaaagctgca ctgctataca agaaaattat ggaaaaatat tctgtaacct   4620
ttataagtag gcataacagt tataatcata acatactgtt ttttcttact ccacacaggc   4680
atagagtgtc tgctattaat aactatgctc aaaaattgtg tacctttagc ttttaatt   4740 gtaaaggggt taataaggaa tatttgatgt atagtgcctt gactagagat cataatcagc   4800
cataccacat ttgtagaggt tttacttgct ttaaaaaacc tcccacacct cccctgaac    4860 ctgaaacata aaatgaatgc aattgttgtt gttaacttgt ttattgcagc ttataatggt   4920
tacaaataaa gcaatagcat cacaaatttc acaaataaag catttttttc actgcattct   4980
agttgtggtt tgtccaaact catcaatgta tcttatcatg tctggatcaa ctggataact   5040
caagctaacc aaaatcatcc caaacttccc accccatacc ctattaccac tgccaattac   5100
ctagtggttt catttactct aaacctgtga ttcctctgaa ttattttcat tttaaagaaa   5160
ttgtatttgt taaatatgta ctacaaactt agtagttgga agggctaatt cactcccaaa   5220
gaagacaaga tatccttgat ctgtggatct accacacaca aggctacttc cctgattagc   5280
agaactacac accagggcca ggggtcagat atccactgac ctttggatgg tgctacaagc   5340
tagtaccagt tgagccagat aaggtagaag aggccaataa aggagagaac accagcttgt   5400 tacccctgt gagcctgcat gggatggatg acccggagag agaagtgtta gagtggaggt    5460
ttgacagccg cctagcattt catcacgtgg cccgagagct gcatccggag tacttcaaga   5520
actgctgata tcgagcttgc tacaagggac tttccgctgg ggacttttcca gggaggcgtg   5580 gcctgggcgg gactggggag tggcgagccc tcagatcctg catataagca gctgcttttt   5640
gcctgtactg ggtctctctg gttagaccag atctgagcct gggagctctc tggctaacta   5700
gggaacccac tgcttaagcc tcaataaagc ttgccttgag tgcttcaagt agtgtgtgcc   5760
cgtctgttgt gtgactctgg taactagaga tccctcagac ccttttagtc agtgtggaaa   5820
atctctagca gtggcgcccg aacagggact tgaaagcgaa agggaaacca gaggagctct   5880
ctcgacgcag gactcggctt gctgaagcgc gcacggcaag aggcgagggg cggcgactgg   5940
tgagtacgcc aaaaattttg actagcggag gctagaagga gagagatggg tgcgagagcg   6000
tcagtattaa gcgggggaga attagatcgc gatgggaaaa aattcggtta aggccagggg   6060
gaaagaaaaa atataaatta aacatatag tatgggcaag cagggagcta gaacgattcg    6120
cagttaatcc tggcctgtta gaaacatcag aaggctgtag acaaatactg ggacagctac   6180
aaccatccct tcagacagga tcagaagaac ttagatcatt atataataca gtagcaaccc   6240
tctattgtgt gcatcaaagg atagagataa agacaccaa ggaagcttta gacaagatag    6300
aggaagagca aaacaaaagt aagaccaccg cacagcaagc ggccgctgat cttcagacct   6360
ggaggaggag atatgaggga caattggaga agtgaattat ataaatataa agtagtaaaa   6420
attgaaccat taggagtagc acccaccaag gcaaagagaa gagtggtgca gagagaaaaa   6480
agagcagtgg gaataggagc tttgttcctt gggttcttgg agcagcagg aagcactatg    6540 ggcgcagcgt caatgacgct gacggtacag gccagacaat tattgtctgg tatagtgcag   6600
cagcagaaca atttgctgag ggctattgag gcgcaacagc atctgttgca actcacagtc   6660
tggggcatca agcagctcca ggcaagaatc ctggctgtgg aaagatacct aaaggatcaa   6720
```

```
cagctcctgg ggatttgggg ttgctctgga aaactcattt gcaccactgc tgtgccttgg    6780
aatgctagtt ggagtaataa atctctggaa cagatttgga atcacacgac ctggatggag    6840
tgggacagag aaattaacaa ttacacaagc ttaatacact ccttaattga agaatcgcaa    6900
aaccagcaag aaaagaatga acaagaatta ttggaattag ataaatgggc aagtttgtgg    6960
aattggttta acataacaaa ttggctgtgg tatataaaat tattcataat gatagtagga    7020
ggcttggtag gtttaagaat agttttgct gtactttcta tagtgaatag agttaggcag    7080
ggatattcac cattatcgtt tcagacccac ctcccaaccc cgaggggacc cgacaggccc    7140
gaaggaatag aagaagaagg tggagagaga cagagacaa gatccattcg attagtgaac    7200
ggatctcgac ggtatcgccg aattcacaaa tggcagtatt catccacaat tttaaaagaa    7260 aagggggat tgggggtac agtgcagggg aaagaatagt agacataata gcaacagaca    7320
tacaaactaa agaattacaa aaacaaatta caaaaattca aaattttcgg gtttattaca    7380
gggacagcag agatccactt tatcgataag cttgggagtt ccgcgttaca taacttacgg    7440
taaatggccc gcctggctga ccgcccaacg accccgccc attgacgtca ataatgacgt    7500
atgttcccat agtaacgcca ataggagactt ccattgacg tcaatgggtg gagtatttac    7560
ggtaaactgc ccacttggca gtacatcaag tgtatcatat gccaagtacg ccccctattg    7620
acgtcaatga cggtaaatgg cccgcctggc attatgccca gtacatgacc ttacgggact    7680
ttcctacttg gcagtacatc tacgtattag tcatcgctat taccatggtg atgcggtttt    7740
ggcagtacac caatgggcgt ggatagcggt ttgactcacg gggatttcca agtctccacc    7800
ccattgacgt caatgggagt ttgttttggc accaaaatca acgggacttt ccaaaatgtc    7860
gtaacaactc cgccccattg acgcaaatgg gcggtaggcg tgtacggtgg aggtctata    7920 taagcagagc tcgtttagtg aaccgtcaga tcgcctggag acgccatcca cgctgttttg    7980
acctccatag aagacaccga ctctagctag aggatccatg gaaacctaca ccaccggggg    8040
gagtattgcc aaaaccgtgc aaggattcac cagtttttt accccaggcg ccaagcagga    8100
catccagctg atcaacacca acggcagttg gcacatcaat cgcacggcct tgaactgtaa    8160
tgcgagcctc gaaaccggct ggatagcggg gctcttctac tacaacaaat tcaactcctc    8220
aggctgcccc gagaggatgg ccagctgcaa acccettgcc tatttcgccc aaggctgggg    8280
ccctatcagc catgtcaacg gaagcggccc cgaacagcgc ccctactgct ggcactacgc    8340
cccaaggcct tgtggtatcg tgtcagcaca gacagtatgt ggcccagtgt attgtttcac    8400
tcctagcccc gtggtggtgg ggacgaccga caagttgggc gcgcctacct acaactgggg    8460
tgagaatgat acggacgtct tcgtcctcaa taacaccagg ccaccgttgg gcaattggtt    8520
cggttgcacc tggatgaact catctggatt caccaaagtg tgcggagcgc ctccctgtgc    8580
catcggagga gtgggcaata acaccttgcg ctgtcccact gactgttttcc gcaagcatcc    8640 ggaagctaca tactctcgat gtggctccgg tccctggatc acgcccaggt gcctggtcga    8700
ctatccttat aggctctggc attatccttg cactgtcaac tacaccctgt ttaaaatcag    8760
gatgtacgtg ggagggtcg agcacaggct acaagctgct tgcaactgga cgcggggcga    8820
gcgttgtgat ctggacgaca gggacaggtc cgagctcagc ccgctgctgc tgtccaccac    8880
gcagtggcag gtccttccgt gttctttcac gaccttgcca gccttgacca ccggcctcat    8940
ccacctccat cagaacatcg tggacgtgca atatttgtac ggggtggggt caagcattgt    9000
gtcctgggcc atcaagtggg agtacgtcat tctcttgttt ctcctgcttg cagacgcgcg    9060
```

```
catctgctcc tgcttgtgga tgatgctact catatcccaa acaagaatcc tcacaatacc    9120
gcagagtcta gactcgtggt ggacttctct caattttcta gggggatctc ccgtgtgtct    9180
tggccaaaat tcgcagtccc caacctccaa tcactcacca acctcctgtc ctccaatttg    9240
tcctggttat cgctggatgt gtctgcggcg ttttatcata ttcctcttca tcctgctgct    9300
atgcctcatc ttcttattgg ttcttctgga ttatcaaggt atgttgcccg tttgtcctct    9360
aattccagga tcaacaacaa ccagtacggg accatgcaaa acctgcacga ctcctgctca    9420
aggcaactct atgtttccct catgttgctg tacaaaacct acggatggaa attgcacctg    9480
tattcccatc ccatcgtcct gggctttcgc aaaataccta tgggagtggg cctcagtccg    9540
tttctcttgg ctcagtttac tagtgccatt tgttcagtgg ttcgtagggc tttcccccac    9600
tgtttggctt tcagctatat ggatgatgtg gtattggggg ccaagtctgt acagcatcgt    9660
gagtcccttt ataccgctgt taccaatttt cttttgtctc tgggtataca tttaataagg    9720
atccggacta gtaactcgag gcccctctcc ctcccccccc cctaacgtta ctggccgaag    9780
ccgcttggaa taaggccggt gtgcgtttgt ctatatgtta ttttccacca tattgccgtc    9840
ttttggcaat gtgagggccc ggaaacctgg ccctgtcttc ttgacgagca ttcctagggg    9900
tcttcccct ctcgccaaag gaatgcaagg tctgttgaat gtcgtgaagg aagcagttcc    9960
tctggaagct tcttgaagac aaacaacgtc tgtagcgacc ctttgcaggc agcggaaccc   10020
cccacctggc gacaggtgcc tctgcggcca aaagccacgt gtataagata cacctgcaaa   10080
ggcggcacaa ccccagtgcc acgttgtgag ttggatagtt gtggaaagag tcaaatggct   10140
ctcctcaagc gtattcaaca aggggctgaa ggatgcccag aaggtacccc attgtatggg   10200
atctgatctg gggcctcggt acacatgctt tacatgtgtt tagtcgaggt taaaaaaacg   10260
tctaggcccc ccgaaccacg gggacgtggt tttcctttga aaaacacgat gataatatgg   10320
ccacaaccat ggtgagcaag ggcgaggagc tgttcaccgg ggtggtgccc atcctggtcg   10380
agctggacgg cgacgtaaac ggccacaagt tcagcgtgtc cggcgagggc gagggcgatg   10440
ccacctacgg caagctgacc ctgaagttca tctgcaccac cggcaagctg cccgtgccct   10500
ggcccaccct cgtgaccacc ctgacctacg gcgtgcagtg cttcagccgc taccccgacc   10560
acatgaagca gcacgacttc ttcaagtccg ccatgcccga aggctacgtc caggagcgca   10620
ccatcttctt caaggacgac ggcaactaca agacccgcgc cgaggtgaag ttcgagggcg   10680
acaccctggt gaaccgcatc gagctgaagg gcatcgactt caaggaggac ggcaacatcc   10740
tggggcacaa gctggagtac aactacaaca gccacaacgt ctatatcatg gccgacaagc   10800
agaagaacgg catcaaggtg aacttcaaga tccgccacaa catcgaggac ggcagcgtgc   10860
agctcgccga ccactaccag cagaacaccc ccatcggcga cggccccgtg ctgctgcccg   10920
acaaccacta cctgagcacc cagtccgccc tgagcaaaga ccccaacgag aagcgcgatc   10980
acatggtcct gctggagttc gtgaccgccg ccgggatcac tctcggcatg gacgagctgt   11040
acaagtaagt cgagggaatt cgagctcggt acctttaaga ccaatgactt acaaggcagc   11100
tgtagatctt agccacttt taaaagaaaa gggggactg gaagggctaa ttcactccca   11160
acgaagacaa gatcttttg cttgtactgg gtctctctgg ttagaccaga tctgagcctg   11220
ggagctctct ggctaactag ggaacccact gcttaagcct caataaagct tgccttgagt   11280
gcttcaagta gtgtgtgccc gtctgttgtg tgactctggt aactagagat ccctcagacc   11340
cttttagtca gtgtggaaaa tctctaga                                      11368
```

FUSION PROTEINS AND USE THEREOF FOR PREPARING HEPATITIS C VACCINES

This is a 371 national stage application of PCT/FR2009/051142 filed Jun. 16, 2009 which claims priority of the foreign application France 0803377 filed Jun. 17, 2008.

The object of the invention is novel fusion proteins and use thereof especially for preparing vaccines intended for the prevention and/or the prophylactic and/or therapeutic treatment of hepatitis C, or the prevention and/or the prophylactic and/or therapeutic treatment of hepatitis C and of hepatitis B. The present invention also relates to obtaining chimeric subviral envelope particles between the envelope proteins of the hepatitis B virus (HBV, for hepatitis B virus) and of the hepatitis C virus (HCV, for hepatitis C virus).

The hepatitis C virus, identified in 1989, then cloned and sequenced, still represents at the present time a real problem for public health on account of its widespread distribution throughout the world and the frequent evolution of the illness towards chronicity. In 2000, the WHO estimated that around 3% of the world's population, i.e. around 170 million people, were infected by HCV.

HCV induces chronic hepatitis, which can evolve into cirrhosis and hepatocellular carcinoma. Interferon and ribavirin form the basic treatment of chronic hepatitis induced by the HCV, but these treatments are not sufficiently efficacious and have important secondary effects. The available treatments remain costly, relatively toxic and are only efficacious in half of the cases of infection.

Even though the whole of the genome and the viral proteins have been known for many years, its structure and is morphogenesis remain hypothetical. No vaccine yet exists against hepatitis C and the search for such a vaccine candidate is currently very active, [Houghton, M., and Abrignani, S. (2005). Prospects for a vaccine against the hepatitis C virus. Nature 436 (7053), 961-6].

In the case of a prophylactic vaccine, the quasi-totality of the potential candidates are based on the use of one of the two or both envelope proteins of the HCV, commonly known as the proteins E1 and E2, and capable of inducing both a cellular immune response and a neutralising humoral response.

However, the proteins E1 and E2 of the HCV do not self-assemble into subviral particles as may be the case for other viruses. Furthermore, on account of a high retention of their transmembrane region in the endoplasmic reticulum, their purification necessitates solubilising than with detergents. Disappointing yields ensue and the purity of the fractions obtained is mediocre [Fours, X., Bukh, J., and Purcell, R. H. (2002). The challenge of developing a vaccine against hepatitis C virus. J Hepatol 37(5), 684-95].

The alternative, consisting in resorting to the envelope proteins deleted of their transmembrane domain, makes it possible to favour the secretion of E1 and E2 on the outside of the cell, but the change of three dimensional conformation that ensues may turn out to be undesirable on account of a diminished antigenic capacity with regard to wild-type proteins.

The HBV virus exists in two forms: in the form of infectious virions and in the form of excess of envelope particles that are found in the blood of infected subjects in much higher quantity than the virus itself. This phenomenon is due to the capacity of the S protein of the HBV to self-assemble and break out into subviral particles (or excess of envelope) which do not contain capsid protein or nucleic acid [Moriarty, A. M., Hoyer, B. H., Shih, J. W., Gerin, J. L., and Hamer, D. H. (1981). Expression of the hepatitis B virus surface antigen gene in cell culture by using a simian virus 40 vector. Proc Natl Acad Sci USA 78(4), 2606-10]. The wild-type S protein of the HBV comprises four transmembrane domains. The subviral particles that result from the self-assembly of the wild-type S protein are non-infectious but very immunogenic: they have been considered as a good vaccine candidate against hepatitis B since the mid 1970s. They have in fact served as the foundation for the elaboration of vaccines having proven their efficaciousness to induce a protective immune response of infection by HBV.

The use of subviral envelope particles of HBV as vector for proteins foreign to the hepatitis B virus has already been the object of prior work. Thus, patent application n°US2004/0146529 entitled "HBV/HCV virus like particle" discloses obtaining HBV-HCV envelope chimeras comprising, on the one hand, systematically the whole of the S protein of the HBV virus, and, on the other hand, according to the examples, a fragment of the ectodomain of one of the E1 or E2 envelope proteins of the HCV, grafted at the N-terminal end of the S protein of the HBV virus [Mark Selby, Edward Glazer and Michael Houghton "HBV/HCV virus-like particle" US patent n° 2004/0146552.91.

However, it is not demonstrated that these constructions can induce the formation of well structured subviral particles, and that they are capable of inducing a quality antigenic response.

In response of the drawbacks of the prior art, the aim of the present invention is to provide a HCV-HBV fusion protein capable of forming non infectious, well structured and efficiently secreted subviral particles, and containing the quasi-totality of E1 and/or E2.

One of the objectives of the invention is also to provide a vaccine against hepatitis C and/or against hepatitis B.

An additional interest of the invention stems from the fact that it can be easily adapted to existing industrial production lines for currently commercialised vaccines against hepatitis B.

The object of the invention is an immunogenic fusion protein comprising at least the following two peptides:

a)—on the C-terminal side, a first peptide composed:
of the amino acid sequence of the S protein of a hepatitis B virus (HBV) isolate, which S protein is deleted of the transmembrane domain thereof located at the N-terminal end thereof, or
of an amino acid sequence having a percentage of identity of at least 91%, especially of at least 93%, particularly of at least 95%, and more particularly of at least 97%, with said amino acid sequence of the N-terminal deleted S protein, under the condition that said amino acid sequence maintains the ability to form non infectious subviral particles, or,
of the amino acid sequence of a natural variant derived from another isolate of the HBV virus, or of a synthetic variant, derived from said amino acid sequence of said N-terminal deleted S protein, under the condition that said amino acid sequence maintains the ability to form non infectious subviral particles, and, b)—on the N-terminal side, a second peptide composed:
of the amino acid sequence of the transmembrane domain and the ectodomain of at least one envelope protein of a hepatitis C virus (HCV) isolate, or
of an amino acid sequence having a percentage of identity of at least 78%, especially of at least 80%, particularly of at least 85%, and more particularly of at least 90%, with said amino acid sequence of the transmembrane domain and of the ectodomain of a protein of a hepatitis C virus isolate, under the condition that said amino acid sequence conserves the immunogenic properties vis-à-vis the hepatitis C virus, or, of the amino acid sequence of a natural variant derived from an isolate of the HCV virus, or of a synthetic variant, derived from said amino acid sequence of one of said proteins E1 or E2, under the condition that said amino acid sequence conserves the immunogenic properties vis-à-vis the hepatitis C virus, said second peptide being chosen from the protein E1, the protein E2 or a fusion peptide comprising the protein E1 and the protein E2.

The invention also relates to an immunogenic fusion protein having an amino acid sequence having a percentage of identity of at least 83%, especially of at least 85%, particularly of at least 90%, and more particularly of at least 95%, with the amino acid sequence composed of the S protein deleted of the N-terminal transmembrane domain thereof (Sd), of the transmembrane domain and of the ectodomain of a protein of a hepatitis C virus isolate (E1 or E2).

"Fusion protein" is taken to mean any protein comprising at least the S protein deleted of the transmembrane domain thereof located at the N-terminal end thereof of an HBV (Sd) isolate, and the quasi-integrality of an envelope protein E1 and/or E2 of an HCV isolate, the transmembrane domain of which replaces that deleted at the N-terminal of S of the HBV (FIGS. 3B, 3C, 4D and 4E).

"Immunogenic protein" is taken to mean any protein, especially any fusion protein according to the invention as well as any fragment of any fusion protein disclosed herein, provided with antigenic properties and capable of inducing a reaction or an immune response. In particular, a protein is considered as immunogenic towards HCV and/or HBV if it induces respectively after immunisation an anti-E1, anti-E2 and/or anti-S humoral response, detected for example according to the protocol described:

by Huzly et al., 2008, as regards HBV, [Huzly D, Schenk T, Jilg W, Neumann-Haefelin D. Comparison of nine commercially available assays for quantification of antibody response to hepatitis B virus surface antigen. J Clin Microbiol. 2008 April, 46(4):1298-306], or, By Hamed et al., 2008, as regards HCV, [Hamed M R. Tarr A W, McClure C P, Ball J K, Hickling T P, Irving W L. Association of antibodies to hepatitis C virus glycoproteins 1 and 2 (anti-E1E2) with HCV disease. J Viral Hepat. 2008 May, 15(5):339-45].

"Capacity to form subviral particles" is taken to mean the capacity of any protein, especially the S protein of the HBV, particularly of the S protein deleted of the N-terminal transmembrane domain thereof, and more particularly of a fusion protein of the invention comprising the N-terminal deleted S protein, to self-assemble in the presence of the wild-type S protein or, if appropriate, to self-assemble into filamentous or spherical subviral particles; said capacity to form subviral particles can at least be highlighted by observation according to especially electron microscope analysis, and especially by the test described in examples 1 and 2 (§I-5 and §II-7) of this document and especially illustrated by FIGS. 7D, 7G, 11B to 11D.

"Non infectious subviral particle" is taken to mean any filamentous or spherical particle resulting from the assembly of the wild-type S protein of the HBV (FIG. 2B) and/or of the S protein deleted of the N-terminal transmembrane domain thereof, said particle being devoid of the viral genome, and especially synthesised and secreted in very large excess, and which may be analysed by any protocol making it possible to highlight the absence of specific nucleotide fragments of HBV or HCV, such as especially, by the amplification by PCR previously disclosed for example:

as regards HCV, by [Halfon P. Bourlière M, Ouzan D, Sène D, Saadoun D, Khiri H, Pénaranda G, Martineau A, Oulès V. Cacoub P. Occult HCV infection revisited with ultra-sensitive real-time PCR assay. J. Clin. Microbiol. 2008 Apr. 30], as regards HCV, by [Thibault V. Pichoud C, Mullen C, Rhoads J, Smith J B, Bitbol A, Thamm S, Zoulim F. Characterization of a new sensitive PCR assay for quantification of viral DNA isolated from patients with hepatitis B virus infections. J. Clin. Microbiol. 2007 December 45(12)1948-53], and the result of which is negative.

"Isolate of the HCV virus" is taken to mean any isolate member of the family of Flaviviridae and belonging to the genus *Hepacivirus* and composed of a polyprotein of more than 3 000 amino acids of the HCV virus, schematised in FIG. 1 [Choo, Q. L., Kuo, G., Weiner, A. J., Overby, L. R., Bradley, D. W., and Houghton, M (1989). Isolation of a cDNA clone derived from a blood-borne non-A, non-B viral hepatitis genome. Science 244(4902), 359-362; Choo et al. Proc. Natl. Acad. Sci. USA (1991) v88:2451-2455; Han et al. Characterization of the terminal regions of hepatitis C viral RNA: identification of conserved sequences in the 5' untranslated region and poly(A) tails at the 3' end. Proc. Natl. Acad. Sci. USA (1991) 88:1711-1715]; or any isolate classified by the International Committee for the Taxonomy of Viruses (ICTV) as being related to the HCV.

"Isolate of the HBV virus" is taken to mean any isolate member of the Hepadnaviridae family and belonging to the genus Orthohepadnavirus, or any isolate classified by the International Committee for the Taxonomy of Viruses (ICTV) as being related to the HBV [Schaefer S. Hepatitis B virus taxonomy and hepatitis B virus genotypes. World J. Gastroenterol. 2007 Jan. 7: 13(1):14-21].

"S proteins" or "wild-type S protein" (5) is taken to mean:

the envelope protein of an isolate of the HBV virus comprising especially 226 amino acids and comprising four transmembrane domains (FIG. 2A), and especially the envelope protein of the HBVadw isolate, or the natural variant derived from an isolate of the HBV virus, or the synthetic variant of the aforementioned S protein.

"Assembly" is taken to mean the capacity of a protein to form subviral particles by associating with the wild-type S protein. "Self assembly" is taken to mean the capacity of a protein to form by itself subviral particles.

"S protein deleted of the transmembrane domain thereof located at the N-terminal end thereof" or "N-terminal deleted S protein" or "deleted S protein" (Sd) is taken to mean:

the S protein as defined above, deleted of the region from the amino acid in position 1 to that in position 19, or in position 1 to that in position 20, or in position 1 to that in position 21, and preferentially in position 1 to that in position 22 of the S protein of an isolate of the HBV virus, or the aforementioned S protein having a percentage of identity of at least 91%, especially of at least 93%, particularly of at least 95%, and more particularly of at least 97%, with said region of the deleted S protein, or the "natural variant" derived from an isolate of the HBV virus, or the "synthetic variant" of the aforementioned deleted S protein.

"Envelope protein of a hepatitis C virus isolate" is taken to mean the quasi-integrality of one of the two proteins E1 and E2, composed of their ectodomain and their transmembrane domain (FIGS. 4B and 4C), and, corresponding:

to the peptide fragments of the polyprotein of the HCV virus, and especially of the HCV-1a isolate of the HCV virus, located in the regions extending:
from the amino acid in position 192 to that in position 383, or especially from the amino acid in position 192 to that in position 380, as regards the protein E1, and,
from the amino acid in position 384 to that in position 746, or especially from the amino acid in position 384 to that in position 743, as regards the protein E2; or the fragments having a percentage of identity of at least 75%, especially of at least 80%, particularly of at least 85%, and more particularly of at least 90%, with said aforementioned region E1, or the fragments having a percentage of identity of at least 78%, especially of at least 80%, particularly of at least 85%, and more particularly of at least 90%, with said aforementioned region E2, or the natural variants or synthetic variants of the polyprotein of an isolate of the HCV virus.

"Ectodomain of the envelope proteins of the hepatitis C virus" is taken to mean, the parts of peptide fragments of E1 or E2, derived from the polyprotein of the HCV virus, and especially from the HCV-1a isolate of the HCV virus, located in the regions extending:
from the amino acid in position 192 to that in position 352, or especially from the amino acid in position 192 to that in position 352, which relates to the ectodomain of the protein E1, and,
from the amino acid in position 384 to that in position 717, or especially from the amino acid in position 384 to that in position 717, which relates to the ectodomain of the protein E2; or the fragments having a percentage of identity of at least 75%, especially of at least 80%, particularly of at least 85%, and more particularly of at least 90%, with said aforementioned region E1, or the fragments having a percentage of identity of at least 78%, especially of at least 80%, particularly of at least 85%, and more particularly of at least 90%, with said aforementioned region E2, or natural variants or synthetic variants of the polyprotein of an isolate of the HCV virus.

"Transmembrane domains of envelope proteins of the hepatitis C virus" is taken to mean, the parts of the peptide fragments of E1 or E2, derived from the polyprotein of the HCV virus, and especially of the HCV-1a isolate of the HCV virus, located in the regions extending:
from the amino acid in position 353 to that in position 383, and advantageously from the amino acid in position 353 to that in position 380, as regards the transmembrane domain of the protein E1, and,
from the amino acid in position 718 to that in position 746 and advantageously from the amino acid in position 718 to that in position 743, as regards the transmembrane domain of the protein E2; or the fragments having a percentage of identity of at least 75%, especially of at least 80%, particularly of at least 85%, and more particularly of at least 90%, with said aforementioned region E1, or the fragments having a percentage of identity of at least 78%, especially of at least 80%, particularly of at least 85%, and more particularly of at least 90%, with said aforementioned region E2, or the natural variants or synthetic variants of the polyprotein of an isolate of the HCV virus.

"Percentage of identity" is taken to mean the percentage determined by direct comparison of two sequences of polypeptide molecules, by determining the number of residues of amino acids at the two sequences, then by dividing it by the number of residues of amino acids of the longest sequence of the two, and by multiplying the result by 100.

An object of the present invention relates to a fusion protein comprising any nucleotide and/or peptide sequence of any isolate of the HCV virus and/or of the HBV virus, whatever the aforementioned percentage of identity of said sequence with regard to the specific sequences disclosed herein.

The term "natural variant" refers to any variability, any polymorphism, any diversity, of a sequence of DNA, of an allele, or of a protein sequence, between isolates of a same species or of a same population. The "percentage of natural variability" is determined by direct comparison of two polypeptide or polynucleotide molecules, derived from a wild-type reference molecule and provided with biological properties of interest, such as immunogenic properties and/or the capacity to form subviral particles. It is quantified by determining the exact number of identical residues of amino acids, or of nucleic acids, between the two sequences, then by dividing than by the number of residues of amino acids, or of nucleic acids, of the shorter sequence of the two, and by multiplying the result by 100.

Said percentage of variability between two sequences is particularly versatile because it depends especially on the virus considered, the genotype considered, the fragment of sequence considered—the region of the ectodomain of the HCV being for example more variable than the region of the transmembrane domain—, etc. . . . . . Thus, the percentage of variability of the proteins E1 and E2 of the HCV is 88% of nucleotides and 90% of amino acids, between strains of a same genotype. But it falls to 55% of nucleotides and 59% of amino acids between strains of different genotypes. HBV being a DNA virus, it is much less variable than HCV [Zhang M, Gaschen B, Blay W, Foley B, Haigwood N, Kuiken C, Korber B. Tracking global patterns of N-linked glycosylation site variation in highly variable viral glycoproteins: HIV, SIV, and HCV envelopes and influenza hemagglutinin. Glycobiology. December 14(12):1229-46].

An object of the present invention relates to a fusion protein, and/or a hybrid nucleic acid molecule, comprising any natural variant or any fragment of natural variant, provided with a peptide and/or nucleotide sequence derived from any isolate of the HCV virus and/or of the HBV virus, whatever the aforementioned percentage of natural and/or synthetic variability of said sequence with regard to the specific sequences disclosed herein.

The term "synthetic variant" refers to any polypeptide or polynucleotide molecule according to the invention, or any fragment of polypeptide or polynucleotide molecule disclosed herein, derived by recombination of a reference wild-type molecule, either by addition, deletion or substitution, to said reference wild-type molecule, on condition that it conserves the biological properties of interest, such as the immunogenic properties and/or the capacity to form subviral particles. The "percentage of synthetic variability" is determined by direct comparison of said derived molecule with said reference wild-type molecule, and by determining the exact number of identical residues of amino acids, or of nucleic acids, between the two sequences, with regard to their position and their nature, then by dividing them by the number of residues of amino acids, or of nucleic acids, of the shorter sequence of the two, and by multiplying the result by 100.

An object of the present invention relates to a fusion protein comprising any synthetic variant or any fragment of synthetic variant, provided with a nucleotide and/or peptide sequence derived from any isolate of the HCV virus and/or of the HBV virus.

According to a particularly advantageous aspect of the invention, the transmembrane domains of E1 and/or of E2, and constituting a part of the fusion protein, are deleted of at least one of the last three amino acids, and especially of the last three amino acids, located at the C-terminal position, so that said transmembrane domains deleted of E1 and/or of E2 have a percentage of identity with the transmembrane domains of wild-type E1 and/or E2, of at least 91%, as regards E1 and of at least 90%, as regards E2.

Said deletion of at least one of the three amino acids, and especially of the last three amino acids, at the C-terminal position has the advantage of inactivating the cleavage site of the peptidases represented in FIG. 1 by the symbol ✕, and which is necessary for the maturation of the polyprotein of the HCV, but which is undesirable within the scope of the chimeric constructions of the present invention.

[1]. The object of the invention is an immunogenic fusion protein comprising at least the following two peptides:
 a)—on the C-terminal side, a first peptide composed:
  of the amino acid sequence of the S protein of a hepatitis B virus (HBV) isolate, which S protein is deleted of the transmembrane domain thereof located at the N-terminal end thereof, or
  of an amino acid sequence having a percentage of identity of at least 91%, especially of at least 93%, particularly of at least 95%, and more particularly of at least 97%, with said amino acid sequence of the N-terminal deleted S protein, under the condition that said amino acid sequence maintains the ability to form immunogenic non infectious subviral particles, vis-à-vis the hepatitis B virus, or,
  of the amino acid sequence of a natural variant derived from another isolate of the HBV virus, or of a synthetic variant derived from said amino acid sequence of the deleted S protein, under the condition that said amino acid sequence maintains the ability to form immunogenic non infectious subviral particles, vis-à-vis the hepatitis B virus, and,
 b)—on the N-terminal side, a second peptide composed:
  of the amino acid sequence of the transmembrane domain and of the ectodomain of at least one envelope protein of a hepatitis C virus (HCV) isolate, or
  of an amino acid sequence having a percentage of identity of at least 78%, especially of at least 80%, particularly of at least 85%, and more particularly of at least 90%, with said amino acid sequence of the transmembrane domain and of the ectodomain of a protein of a hepatitis C virus isolate, under the condition that said amino acid sequence maintains the ability to form immunogenic non infectious subviral particles, vis-à-vis the hepatitis C virus, or
  of the amino acid sequence of a natural variant derived from an isolate of the HCV virus, or of a synthetic variant derived from said amino acid sequence, of said proteins E1 or E2, under the condition that said amino acid sequence conserves the immunogenic properties vis-à-vis the hepatitis C virus,
said second peptide being chosen from the protein E1, the protein E2 or a fusion peptide comprising the protein E1 and the protein E2.

The object of the present invention especially relates to a fusion protein comprising at least:
 on the one hand, the deleted S protein of HBV (Sd), essentially composed of its three transmembrane domains located at the C-terminal end (FIGS. 2A and 3A), said deleted S protein conserving the capacity of assembling into subviral particles, and conserving the immunogenic properties against the HBV virus, and
 on the other hand, the quasi-integrality of the sequence of one of proteins E1 and E2, also conserving immunogenic properties against the HCV virus,
so that said fusion protein, especially represented by FIG. 3B or 3C, is capable of self-assembly into subviral particles, in the presence of the wild-type S protein, and is capable of inducing an immunisation against the HBV and/or HCV viruses, and especially of inducing a double immunisation against the HBV and HCV viruses.

[1a]. Advantageously, the object of the present invention is an aforementioned immunogenic fusion protein, comprising at the N-terminal end of said second peptide (E1 or E2), a third peptide composed of the sequence of amino acids of a transfer initiation peptide (PIT) of a hepatitis C virus isolate.

"Transfer initiation peptide" is taken to means a protein E1 or E2 (respectively PIT1 and PIT2) or a fusion protein according to the invention,
 the peptide fragment of the polyprotein of the HCV virus, and especially of the HCV-1a isolate, located in the region extending:
  from the amino acid in position 166 to that in position 191 as regards the protein E1, and,
  from the amino acid in position 366 to that in position 383 as regards the protein E2; or
 the natural variant derived from an isolate of the HCV virus, or the synthetic variant of said aforementioned peptide fragment, or
 any peptide fragment grafted at the N-terminal of said second peptide,
under the condition that said peptide fragment, when it constitutes a part of the fusion protein of the present invention, maintains the ability to address, after translation, said fusion protein to the endoplasmic reticulum so that it is correctly glycosylated and that its three dimensional conformation, and/or that its antigenic characteristics, are at best preserved with regard to wild-type S proteins.

[2]. According to another particularly advantageous aspect, the object of the present invention is an aforementioned immunogenic fusion protein, in which the second peptide located on the N-terminal side, is composed:
 of the totality of the amino acid sequence of the transmembrane domain and of the ectodomain of the envelope protein E1, or
 of an amino acid sequence having a percentage of identity of at least 75%, especially of at least 80%, particularly of at least 85%, and more particularly of at least 90%, with said amino acid sequence of the transmembrane domain and of the ectodomain of the envelope protein E1, under the condition that said amino acid sequence conserves the immunogenic properties vis-à-vis the hepatitis C virus, or
 of the amino acid sequence of a natural variant derived from an isolate of the HCV virus, or of a synthetic variant derived from said protein E1; under the condition that said amino acid sequence conserves the immunogenic properties vis-à-vis the hepatitis C virus.

A particular object of the invention resides in the fusion protein E1-Sd, a schematic representation of which is given in FIG. 3B, and which comprises the quasi-integrality of the protein E1 of the HCV, grafted at the N-terminal of the deleted S protein of HBV.

[3]. Advantageously, the object of the present invention is particularly an aforementioned immunogenic fusion protein in which the second peptide located on the N-terminal side, is composed:
- of the totality of the amino acid sequence of the transmembrane domain and of the ectodomain of the envelope protein E2, or
- of an amino acid sequence having a percentage of identity of at least 78%, especially of at least 80%, particularly of at least 85%, and more particularly of at least 90%, with said amino acid sequence of the transmembrane domain and of the ectodomain of the envelope protein E2, under the condition that said amino acid sequence conserves the immunogenic properties vis-à-vis the hepatitis C virus, or
- of the amino acid sequence of a natural variant derived from an isolate of the HCV virus, or of a synthetic variant derived from said protein E2, under the condition that said amino acid sequence conserves the immunogenic properties vis-à-vis the hepatitis C virus.

A particular object of the invention resides in the fusion protein E2-Sd, a schematic representation of which is given in FIG. 3C, and which comprises the quasi-integrality of the protein E2 of the HCV, grafted at the N-terminal of the deleted S protein of HBV.

[3b]. In this respect, the invention relates more particularly to an immunogenic fusion protein, comprising the following three peptides:
a)—on the C-terminal side, a first peptide composed:
- of the amino acid sequence of the S protein deleted of the transmembrane domain thereof of the N-terminal end of a hepatitis B virus (HBV) isolate, or
- of an amino acid sequence having a percentage of identity of at least 91%, especially of at least 93%, particularly of at least 95%, and more particularly of at least 97%, with said amino acid sequence of the N-terminal deleted S protein, under the condition that said amino acid sequence maintains the ability to form immunogenic non infectious subviral particles, vis-à-vis the hepatitis B virus, or
- of the amino acid sequence of a natural variant, derived from an isolate of the HBV virus, or of a synthetic variant derived from said amino acid sequence of the N-terminal deleted S protein, under the condition that said amino acid sequence maintains the ability to form immunogenic non infectious subviral particles, vis-à-vis the hepatitis B virus;

b)—a second peptide of sequence composed:
- of the totality of the amino acid sequence of the transmembrane domain and the ectodomain of an envelope protein E2 of a hepatitis C virus isolate, or
- of an amino acid sequence having a percentage of identity of at least 78%, especially of at least 80%, particularly of at least 85%, and more particularly of at least 90%, with said amino acid sequence of the transmembrane domain and of the ectodomain of said envelope protein, under the condition that said amino acid sequence conserves the immunogenic properties vis-à-vis the hepatitis C virus, or
- of the amino acid sequence of a natural variant, derived from an isolate of the HCV virus, or of a synthetic variant derived from said amino acid sequence of the protein E2, under the condition that said amino acid sequence conserves the immunogenic properties vis-à-vis the hepatitis C virus, and, c)—on the N-terminal side, a third peptide of sequence composed:
- of the totality of the amino acid sequence of the transmembrane domain and of the ectodomain of an envelope protein E1, of a hepatitis C virus isolate, or
- of an amino acid sequence having a percentage of identity of at least 75%, especially of at least 80%, particularly of at least 85%, and more particularly of at least 90%, with said amino acid sequence of the transmembrane domain and of the ectodomain of said envelope protein, under the condition that said amino acid sequence conserves the immunogenic properties vis-à-vis the hepatitis C virus, or
- of the amino acid sequence of a natural variant, derived from an isolate of the HCV virus, or of a synthetic variant, derived from said amino acid sequence of a protein E1, under the condition that said amino acid sequence conserves the immunogenic properties vis-à-vis the hepatitis C virus, said second peptide being located between the first and the third peptide, the first, second and third peptides being preferably contiguous.

A particular object of the invention resides in the fusion protein E1-E2-Sd, which comprises the ectodomain of E1 of the HCV grafted at the N-terminal of the quasi-integrality of the protein E2, itself grafted at the N-terminal of the deleted S protein of HBV.

A particular object of the invention also resides in the fusion protein E2-E1-Sd, and which comprises the ectodomain of E2 of the HCV grafted at the N-terminal of the quasi-integrality of the protein E1, itself grafted at the N-terminal of the deleted S protein of HBV.

[4]. According to a particularly advantageous aspect of the invention, the first and the second peptide constituting the immunogenic fusion protein are contiguous, and the C-terminal end of the second peptide is bonded in a covalent manner to the N-terminal end of the first peptide.

Advantageously, according to the invention, the proteins E1 or E2 of the HCV virus, or the fragments of a fusion protein of the invention PIT1-E1, PIT2-E2, E1-E2, or PIT1-E1-E2 are bonded in a covalent and contiguous manner to the deleted S protein of the HBV virus.

According to another advantageous aspect of the invention, a binding peptide links the first and the second peptide constituting the aforementioned fusion protein, said binding peptide being composed of 1 amino acid, or 2 amino acids, or 3 amino acids, or 4 amino acids, or 5 amino acids; under the condition that said immunogenic fusion protein maintains the ability for self-assembling into subviral particles, in the presence of the wild-type S protein, and the immunogenic properties vis-à-vis the HCV virus, or the HBV virus, or, the HCV and HBV viruses.

[5]. Another particular object of the invention is an aforementioned immunogenic fusion protein, in which the first peptide in C-terminal position is composed:
- of an amino acid sequence bounded by the contiguous amino acids located in the region extending from the amino acid in position 23 to that in position 226 of the N-terminal deleted S protein of the HBV virus, and particularly of the HBVadw isolate, and especially of the amino acid sequence represented by the SEQ ID NO: 2, or
- of an amino acid sequence having a percentage of identity of at least 91%, especially of at least 93%, particularly of at least 95%, and more particularly of at least 97%, with said contiguous amino acid sequence of the N-terminal deleted S protein, under the condition that said amino acid sequence maintains the ability to form immunogenic non infectious subviral particles, vis-à-vis the hepatitis B virus, or of the amino acid sequence of a natural variant derived from an isolate of the HBV virus, or of a synthetic variant, derived from said amino acid sequence of the N-terminal deleted S protein, under the condition that said amino acid sequence maintains the ability to form immunogenic non infectious subviral particles, vis-à-vis the hepatitis B virus.

A more particular object of the invention resides in the fusion protein E1-Sd or E2-Sd, or E1-E2-Sd, for which the deleted S protein is that of the HBVadw isolate and has for sequence the SEQ ID NO: 2 (cf. table 1).

[6]. Another particular object of the invention is an aforementioned immunogenic fusion protein, in which the second peptide in N-terminal position is composed:

of an amino acid sequence bounded by the contiguous amino acids located in the region extending from the amino acid in position 192 to that in position 380 of the protein E1 of HCV, and particularly of the HCV-1a isolate, and especially of the amino acid sequence represented by the SEQ ID NO: 4, or of an amino acid sequence having a percentage of identity of at least 75%, especially of at least 80%, particularly of at least 85%, and more particularly of at least 90%, with said contiguous amino acid sequence of said protein E1, under the condition that said amino acid sequence conserves the immunogenic properties vis-à-vis the hepatitis C virus, or of the amino acid sequence of a natural variant derived from an isolate of the HCV virus, or of a synthetic variant derived from said contiguous amino acid sequence of said protein E1, under the condition that said amino acid sequence conserves the immunogenic properties vis-à-vis the hepatitis C virus.

Another particular object of the invention is a fusion protein for which the sequence of protein E1 is derived from the HCV-1a isolate, and corresponds specifically to the aforementioned region, such as especially the fusion proteins E1-Sd of SEQ ID NO: 4 or E1-E2-Sd, PIT1-E1-E2-Sd (cf. table 1).

[7]. The invention particularly relates to an aforementioned immunogenic fusion protein, in which the first and the second peptide are contiguous, said fusion protein being composed of:

the amino acid sequence represented by the SEQ ID NO: 8, or an amino acid sequence having a percentage of identity of at least 88%, especially of at least 90%, particularly of at least 92%, and more particularly of at least 95%, with SEQ ID NO: 8, under the condition that said amino acid sequence maintains the ability to form non infectious subviral particles, immunogenic vis-à-vis HCV and/or vis-à-vis HBV, or of the amino acid sequence of a synthetic variant derived from said SEQ ID NO: 8, under the condition that said amino acid sequence maintains the ability to form immunogenic non infectious subviral particles, vis-à-vis HCV and/or vis-à-vis HBV.

Another object of the invention is a fusion protein E1-Sd for which the sequence of protein E1 is derived from the HCV-1a isolate, and is provided with the aforementioned sequence SEQ ID NO: 8, said sequence corresponding to the SEQ ID NO: 2 of Sd, grafted ahead of the SEQ ID NO: 4 of E1.

[7b]. In this respect, the object of the invention is more particularly an aforementioned immunogenic fusion protein, comprising a third transfer initiation peptide located at the N-terminal side of the second peptide, said fusion protein being represented by:

the SEQ ID NO: 12, or an amino acid sequence having an homology of identity of at least 83%, especially of at least 85%, particularly of at least 90%, and more particularly of at least 95%, with said SEQ ID NO: 12, under the condition that said amino acid sequence maintains the ability to form immunogenic non infectious subviral particles, vis-à-vis the hepatitis B virus and/or vis-à-vis the hepatitis C virus, or of the amino acid sequence of a synthetic variant derived from said SEQ ID NO: 12, under the condition that said amino acid sequence maintains the ability to form immunogenic non infectious subviral particles, vis-à-vis the hepatitis B virus and/or vis-à-vis the hepatitis C virus.

Another object of the invention is the fusion protein PIT1-E1-Sd, for which the sequence of protein E1 is derived from HCV, and particularly from the HCV-1a isolate, and is provided with the aforementioned sequence SEQ ID NO: 12, said sequence corresponding SEQ ID NO: 2 of Sd, grafted at the N-terminal of the SEQ ID NO: 4 of E1, itself grafted at the N-terminal of the amino acid sequence of the transfer initiation peptide of the protein E1 (PIT1) included in the region extending from the amino acid in position 166 to that in position 191 of the HCV.

The insertion of a transfer initiation peptide at the N-terminal of the aforementioned fusion protein E1-Sd has the particular advantage of addressing the latter once translated to the endoplasmic reticulum, so that it is correctly glycosylated and that its three dimensional conformation and/or that its antigenic characteristics do not show any substantial alteration with regard to wild-type proteins.

[8]. Another object of the invention is an aforementioned immunogenic fusion protein, in which the second peptide in N-terminal position is composed:

of an amino acid sequence bounded by the contiguous amino acids located from the amino acid in position 384 to that in position 743 of the protein E2 of HCV, and particularly of the HCV-1a isolate, and especially the amino acid sequence represented by the SEQ ID NO: 6, or of an amino acid sequence having a percentage of identity of at least 78%, especially of at least 80%, particularly of at least 85%, and more particularly of at least 90%, with said contiguous amino acid sequence of protein E2, under the condition that said amino acid sequence conserves the immunogenic properties vis-à-vis the hepatitis C virus, or of the amino acid sequence of a natural variant derived from an isolate of the HCV virus or of a synthetic variant, derived from said contiguous amino acid sequence of protein E2, under the condition that said amino acid sequence conserves the immunogenic properties vis-à-vis the hepatitis C virus, Another object of the invention is the fusion protein E2-Sd or E1-E2-Sd, for which the sequence of protein E2 is derived from the HCV, and particularly from the HCV-1a isolate, and corresponds specifically to the aforementioned region of the sequence of the protein E2.

[9]. The invention particularly relates to an aforementioned immunogenic fusion protein, in which the first and the second peptide are contiguous, said fusion protein being composed of:

the amino acid sequence represented by SEQ ID NO: 10, or an amino acid sequence having a percentage of identity of at least 86%, especially of at least 88%, particularly of at least 90%, and more particularly of at least 95%, SEQ ID NO: 10, under the condition that said amino acid sequence maintains the ability to form immunogenic non infectious subviral particles, vis-à-vis the hepatitis B virus and/or vis-à-vis the hepatitis C virus, or of the amino acid sequence of a synthetic variant derived from said SEQ ID NO: 10, under the condition that said amino acid sequence maintains the ability to form immunogenic non infectious subviral particles, vis-à-vis the hepatitis B virus and/or vis-à-vis the hepatitis C virus.

Another object of the invention is the fusion protein E2-Sd, for which the sequence of the protein E2 is derived from the HCV-1a isolate, and is provided with the aforementioned sequence SEQ ID NO: 10, said sequence corresponding to SEQ ID NO: 2 of Sd, grafted ahead of the SEQ ID NO: 6 of E2.

[9b]. In this respect, the object of the invention is more particularly an aforementioned immunogenic fusion protein (PIT2-E2-Sd), comprising a third transfer initiation peptide located on the N-terminal side of the second peptide, said fusion protein being represented by:

the SEQ ID NO: 14, or an amino acid sequence having an homology of identity of at least 82%, especially of at least 85%, particularly of at least 90%, and more particularly of at least 95%, with said SEQ ID NO: 14, or the amino acid sequence of a synthetic variant derived from said SEQ ID NO: 14, under the condition that said SEQ ID NO: 14 maintains the ability to form immunogenic non infectious subviral particles, vis-à-vis the hepatitis B virus and/or vis-à-vis the hepatitis C virus.

Another object of the invention is the fusion protein PIT2-E2-Sd, for which the sequence of protein E2 is derived from the HCV-1a isolate, and is provided with the aforementioned sequence SEQ ID NO: 14, said sequence corresponding to the SEQ ID NO: 2 of Sd, grafted at the N-terminal of the SEQ ID NO: 6 of E2, itself grafted at the N-terminal of the amino acid sequence of the transfer initiation peptide of the protein E2 (PIT2) included in the region composed of the amino acid in position 366 to that in position 383 of HCV.

Another object of the invention is the fusion protein E1-E2-Sd or PIT1-E1-E2-Sd. Another object of the invention is the aforementioned fusion proteins in purified form.

The invention also relates to a hybrid nucleic acid molecule encoding for any of the aforementioned fusion proteins.

"Hybrid nucleic acid molecule" is taken to mean any nucleic acid molecule comprising at least one sequence encoding for the S protein deleted of the transmembrane domain thereof located at the N-terminal end thereof of a hepatitis B virus (HBV) isolate, and at least one sequence encoding for the quasi-integrality of an envelope protein of a hepatitis C virus isolate, or any molecule derived from a molecule defined above, and modified following the natural degeneration of its genetic code.

Advantageously, the invention relates to an aforementioned hybrid nucleic acid molecule, encoding for a fusion protein defined above, comprising the following three nucleic acid sequences:

a)—on the 3' side, a first nucleic acid sequence encoding for the S protein deleted of the transmembrane domain thereof located at the N-terminal end thereof, of a hepatitis B virus (HBV) isolate, or of a nucleic acid sequence having an homology of at least 91%, especially of at least 93%, particularly of at least 95%, and more particularly of at least 97%, with said nucleic acid sequence of the N-terminal deleted S protein, under the condition that the protein encoded by said nucleic acid sequence maintains the ability to form immunogenic non infectious subviral particles, vis-à-vis the hepatitis B virus, or of the nucleic acid sequence of a natural variant derived from another isolate of the HBV virus, or of a synthetic variant, derived from a nucleic acid sequence of said N-terminal deleted S protein, under the condition that the protein encoded by said nucleic acid sequence maintains the ability to form immunogenic non infectious subviral particles, vis-à-vis the hepatitis B virus, and, b)—on the 5' side of the first sequence, a second nucleic acid sequence encoding for the transmembrane domain and the ectodomain of at least one envelope protein E1 or E2 of a hepatitis C virus isolate, or of a nucleic acid sequence having an homology of identity of at least 78%, especially of at least 80%, particularly of at least 85%, and more particularly of at least 90%, with said nucleic acid sequence encoding for one of said proteins E1 or E2 of a hepatitis C virus isolate, under the condition that the protein encoded by said nucleic acid sequence conserves the immunogenic properties vis-à-vis the hepatitis C virus, of the nucleic acid sequence of a natural variant derived from an isolate of the HCV virus, or of a synthetic variant, derived from said nucleic acid sequence of one of said proteins E1 or E2, under the condition that the protein encoded by said nucleic acid sequence conserves the immunogenic properties vis-à-vis the hepatitis C virus, said second sequence being chosen from the sequences encoding for the protein E1, for the protein E2 or for a fusion peptide comprising the protein E1 and the protein E2, and, c)—on the 5' side of the second sequence, a third nucleic acid sequence encoding for a transfer initiation peptide of an envelope protein E1 or E2 of a hepatitis C virus isolate (PIT), or a nucleic acid sequence of a natural variant derived from an isolate of the HCV virus, or of a synthetic variant, derived from said nucleic acid sequence of the protein encoding for a transfer initiation peptide (PIT), under the condition that the transfer initiation peptide encoded by said nucleic acid sequence maintains the ability to address, after translation, said fusion protein to the endoplasmic reticulum so that it is correctly glycosylated and that its three dimensional conformation has the fewest possible alterations, and/or that its antigenic characteristics are at best preserved with regard to wild-type S proteins, or, any nucleic acid sequence encoding for a peptide capable of addressing, after translation, said fusion protein to the endoplasmic reticulum so that it is correctly glycosylated and that its three dimensional conformation presents the fewest possible alterations, and/or that its antigenic characteristics are at best preserved with regard to wild-type proteins.

Advantageously, the object of the present invention is an aforementioned hybrid nucleic acid molecule (especially the molecules e1-sd or e2-sd, or e1-e2-sd, pit1-e1-sd or pit2-e2- sd, as defined in table 1 below), encoding for an aforementioned fusion protein (especially E1-Sd or E2-Sd, or E1-E2-Sd, PIT1-E1-Sd or PIT2-E2-Sd), comprising respectively from its 5' end to its 3' end, a nucleic acid sequence encoding for a transfer initiation peptide (PIT) of an isolate of the hepatitis C virus, a nucleic acid sequence encoding for a protein E1 or E2 of an isolate of the HCV virus, a nucleic acid sequence encoding for the deleted S protein of an isolate of the HBV virus.

The insertion of a nucleic acid sequence encoding for said transfer initiation peptide grafted at the N-terminal of the aforementioned fusion protein (especially E1-Sd or E2-Sd, or E1-E2-Sd) has the particular advantage that the latter once translated is addressed to the endoplasmic reticulum, so that it is correctly glycosylated and that its three dimensional conformation and/or that its antigenic characteristics do not show substantial alteration with regard to wild-type S proteins.

Another object of the present invention is an aforementioned hybrid nucleic acid molecule only comprising the first two aforementioned nucleic acid sequences and devoid of nucleic acid sequence encoding for a transfer initiation peptide.

The object the present invention especially relates to an aforementioned hybrid nucleic acid molecule encoding for a fusion protein of the invention, comprising at least:
- the nucleic acid sequence encoding for the deleted S protein of HBV (Sd), essentially composed of its three transmembrane domains located at the C-terminal end (FIGS. 2A and 3A), said deleted S protein conserving the capacity of assembling into subviral particles, and conserving the immunogenic properties against the HBV virus, and
- the nucleic acid sequence encoding for the quasi-integrality of the sequence of one of the proteins E1 and E2 (FIGS. 3B and 3C), also conserving the immunogenic properties against the HCV virus,
- the nucleic acid sequence encoding for a transfer initiation peptide of the invention, conserving the capacity of addressing after translation said fusion protein to the endoplasmic reticulum so that it is correctly glycosylated and that its three dimensional conformation has the least possible alterations, and/or that the antigenic characteristics are at best preserved with regard to wild-type S proteins,
- so that the fusion protein encoded by said aforementioned hybrid nucleic acid molecule maintains the ability to form subviral particles, and the immunogenic properties vis-à-vis the HBV and/or HCV virus, and especially the property of inducing a double immunisation against the HBV and HCV viruses.

"Percentage of homology" is taken to mean the percentage determined by direct comparison of two sequences of polynucleotide molecules, by determining the number of residues of nucleic acids of the two sequences, then by dividing it by the number of residues of nucleic acids of the longest sequence of the two, and by multiplying the result by 100.

According to a particularly advantageous aspect of the invention, the nucleic acid sequences encoding for the transmembrane domains of E1 and/or of E2, are deleted of at least one of the last nine nucleic acids, and preferentially of the last nine nucleic acids, located in 3' position, so that the nucleic acid sequences encoding for the transmembrane domains of E1 and/or of E2 correspond:

- to the nucleotide fragments of the genome of an isolate of HCV, located in the regions extending:
  - from the nucleic acid in position 1398 to that in position 1490 and, advantageously, from the nucleic acid in position 1398 to that in position 1481 as regards the nucleic acid sequence encoding for the transmembrane domains of E1, or
  - from the nucleic acid in position 2493 to that in position 2579 and, advantageously, from the nucleic acid in position 2493 to that in position 2570 as regards the nucleic acid sequence encoding for the transmembrane domains of E2, or
- to the nucleotide fragments of the genome of an isolate of HCV having a percentage of homology with said aforementioned wild-type nucleotide fragments of the genome of the HCV, of at least 91%, as regards E1 and of at least 90%, as regards E2, or
- to the nucleotide fragments derived from natural variants of the HCV virus, and/or derived from synthetic variants of said wild-type nucleotide fragments of the genome of an isolate of HCV.

The expression "transmembrane domains of E1 and/or of E2 deleted of at least one of the last nine nucleic acids located in 3'" position relates to deletions of 3 nucleic acids, or of 6 nucleic acids, or of 9 nucleic acids located in 3' position of one of said transmembrane domains.

Advantageously, the first and the second nucleic acid sequence of the aforementioned hybrid nucleic acid molecule and encoding for the aforementioned immunogenic fusion protein are contiguous, and the 5' end of the first nucleic acid sequence is bonded in a covalent manner to the 3' end of the second nucleic acid sequence.

According to a particularly advantageous aspect, the hybrid nucleic acid molecule defined above corresponds for example to the following molecules: e1-sd, e2-sd, or pit1-e1-sd or pit 2-e2-sd, encoding respectively for the following fusion proteins: E1-Sd, E2-Sd, PIT1-E1-Sd or PIT2-E2-Sd).

According to another advantageous aspect of the invention, a nucleotide sequence encoding for a binding peptide, links said aforementioned first and second nucleotide sequences, said nucleotide sequence being composed:
- of 3 nucleic acids, or 6 nucleic acids, or 9 nucleic acids, or 12 nucleic acids, or 15 nucleic acids, or
- of any nucleotide sequence encoding for any binding peptide;
- under the condition that the immunogenic fusion protein encoded by the hybrid nucleic acid molecule and which comprises said binding peptide, itself encoded by said nucleotide sequence, maintains the ability for self-assembling into non infectious subviral particles, in the presence of the wild-type S protein, and conserves the immunogenic properties vis-à-vis the HCV virus, and/or, the HBV virus.

In this respect, the object of the invention is particularly an aforementioned hybrid nucleic acid molecule, in which the first nucleic acid sequence encoding for the N-terminal deleted S protein, of HBV, and particularly of the HBVadw isolate, is located on the 3' side of said hybrid nucleic acid molecule, and is composed:
- of a nucleic acid sequence bounded by the contiguous nucleic acids located from the position 1630 to the position 2241 of the genome of HBV, and especially,
- of the nucleic acid sequence represented by the SEQ ID NO: 1, or
- of a nucleic acid sequence having an homology of at least 91%, especially of at least 93%, particularly of at least 95%, and more particularly of at least 97%, with said nucleic acid sequence encoding for said N-terminal deleted S protein, under the condition that the protein encoded by said nucleic acid sequence maintains the ability to form immunogenic non infectious subviral particles, vis-à-vis the hepatitis B virus, or, of the nucleic acid sequence of a natural variant derived from an isolate of the HBV virus or of a synthetic variant, derived from said nucleic acid sequence encoding for said N-terminal deleted S protein, under the condition that the protein encoded by said nucleic acid sequence maintains the ability to form immunogenic non infectious subviral particles, vis-à-vis the hepatitis B virus.

A more particular object of the invention relates to an aforementioned hybrid nucleic acid molecule (especially e1-sd or e2-sd, or e1-e2-sd, pit1-e1-sd or pit2-e2-sd, or pit1-e1-e2-sd) encoding for an aforementioned fusion protein (especially E1-Sd or E2-Sd, or E1-E2-Sd, PIT1-E1-Sd or PIT2-E2-Sd, or PIT1-E1-E2-Sd) for which said nucleic acid sequence encoding for the deleted S protein of the HCV is that of the HBVadw isolate, and has for sequence SEQ ID NO: 1.

In this respect again, the invention relates more particularly to an aforementioned hybrid nucleic acid molecule, in which the second nucleic acid sequence encoding for the transmembrane domain and the ectodomain of the protein E1 of HCV, and particularly of the HCV-1a isolate, is located on the 5' side of said hybrid nucleic acid molecule, and is composed:

of a nucleic acid sequence bounded by the contiguous nucleic acids located from the position 915 to the position 1490, and particularly from the position 915 to the position 1481, of the genome of HCV, and particularly of the HCV-1a isolate, and especially the nucleic acid sequence represented by the SEQ ID NO: 3, or of a nucleic acid sequence having a homology of at least 75%, especially of at least 80%, particularly of at least 85%, and more particularly of at least 90%, with said nucleic acid sequence of the protein E1, under the condition that the protein encoded by said nucleic acid sequence conserves the immunogenic properties vis-à-vis the hepatitis C virus, or of the nucleic acid sequence of a natural variant derived from an isolate of the HCV virus or of a synthetic variant derived from said nucleic acid sequence of the protein E1, under the condition that the protein encoded by said nucleic acid sequence conserves the immunogenic properties vis-à-vis the hepatitis C virus.

A more particular object of the invention relates to an aforementioned hybrid nucleic acid molecule (especially e1-sd or pit1-e1-sd, or e1-e2-sd, or pit1-e1-e2-sd) encoding for a fusion protein (especially E1-Sd or PIT1-E1-Sd, or E1-E2-Sd, or PIT1-E1-E2-Sd), for which said nucleic acid sequence encoding for the protein E1 is that of the HCV-1a isolate, is the sequence SEQ ID NO: 3.

The invention particularly relates to an aforementioned hybrid nucleic acid molecule, encoding for an aforementioned fusion protein, comprising a transfer initiation peptide located on the N-terminal side, said hybrid nucleic acid molecule being represented by:

the SEQ ID NO: 11, or a nucleic acid sequence having an homology of identity of at least 78%, especially of at least 80%, particularly of at least 85%, and more particularly of at least 90%, with said SEQ ID NO: 11, under the condition that the protein encoded by said nucleic acid sequence conserves the immunogenic properties vis-à-vis HCV and/or HBV, or the nucleic acid sequence of a synthetic variant, derived from said SEQ ID NO: 11, under the condition that the protein encoded by said nucleic acid sequence conserves the immunogenic properties vis-à-vis HCV and/or HBV.

The nucleic acid sequence SEQ ID NO: 11, also named pit1-e1-sd, encodes for the fusion protein PIT1-E1-Sd of SEQ ID NO: 12 (cf. table 1).

Another object of the invention is a hybrid nucleic acid molecule (especially pit1-e1-sd of SEQ ID NO: 11) for which:

the nucleic acid sequence encoding for the protein E1 is derived from HCV, and particularly from the HCV-1a isolate, and is the aforementioned sequence SEQ ID NO: 3 and, the nucleic acid sequence encoding for the S protein is derived from HBV, and particularly from the HBVadw isolate, and is the aforementioned sequence SEQ ID NO: 1, said SEQ ID NO: 1 being grafted at the 5' side of the SEQ ID NO: 3 of E1, itself grafted at the 5' side of the nucleic acid sequence encoding for the transfer initiation peptide of the protein E1 (PIT1) included in the region constituted of the nucleic acid in position 837 to that in position 914 of HCV.

In this respect, the object of the invention relates more particularly to an aforementioned hybrid nucleic acid molecule, in which the second nucleic acid sequence encoding for the transmembrane domain and the ectodomain of the protein E2 of HCV, and particularly of the HCV-1a isolate, is located on the 5' side of said molecule, and is composed:

of a nucleic acid sequence bounded by the contiguous nucleic acids located from the position 1491 to the position 2579, and particularly from the position 1491 to the position 2570, of the genome of HCV, and particularly of the HCV-1a isolate, and especially the nucleic acid sequence represented by the SEQ ID NO: 5, or of a nucleic acid sequence having an homology of at least 78%, especially of at least 80%, particularly of at least 85%, and more particularly of at least 90%, with said nucleic acid sequence of the protein E2, under the condition that the protein encoded by said nucleic acid sequence conserves the immunogenic properties vis-à-vis the hepatitis C virus, or of the nucleic acid sequence of a natural variant derived from an isolate of the HCV virus or from a synthetic variant, derived from said SEQ ID NO: 5, under the condition that the protein encoded by said nucleic acid sequence conserves the immunogenic properties vis-à-vis the hepatitis C virus.

A more particular object of the invention relates to an aforementioned hybrid nucleic acid molecule (especially e2-sd or pit2-e2-sd) encoding for a fusion protein (especially E2-Sd or PIT2-E2-Sd).

The invention relates particularly to an aforementioned hybrid nucleic acid molecule, encoding for a fusion protein of the invention, comprising a transfer initiation peptide located on the N-terminal side, said hybrid nucleic acid molecule being represented by:

the SEQ ID NO: 13, or a nucleic acid sequence having an homology of identity of at least 80%, especially of at least 85%, particularly of at least 90%, and more particularly of at least 95%, with said SEQ ID NO: 13, under the condition that the protein encoded by said nucleic acid sequence conserves the immunogenic properties vis-à-vis the HCV and/or HBV virus, or the nucleic acid sequence derived from a synthetic variant, derived from said SEQ ID NO: 13, under the condition that the protein encoded by said nucleic acid sequence conserves the immunogenic properties vis-à-vis the HCV and/or HBV virus.

The nucleic acid sequence SEQ ID NO: 13, also named pit2-e2-sd, encodes for the fusion protein PIT2-E2-Sd of SEQ ID NO: 14 (cf. table 1).

Another object of the invention is a hybrid nucleic acid molecule (especially pit2-e2-sd de SEQ ID NO: 3) for which:

the nucleic acid sequence encoding for the protein E2 is derived from HCV, and particularly from the HCV-1a isolate, and is the aforementioned sequence SEQ ID NO: 5 and, for which the nucleic acid sequence encoding for the S protein is derived from HBV, and particularly from the HBVadw isolate, and is the aforementioned sequence SEQ ID NO: 1, said SEQ ID NO: 1 being grafted at the 5' side of the SEQ ID NO: 5 de E2, itself grafted at the 5' side of the nucleic acid sequence encoding for the transfer initiation peptide of the protein E2 (PIT2) included in the region constituted of the nucleic acid in position 1437 to that in position 1490 of the HCV.

Another object of the invention is a vector comprising an aforementioned hybrid nucleic acid molecule encoding for an aforementioned fusion protein, as well as the means necessary for their expression linked in an operational manner to said hybrid nucleic acid molecule.

As regards expression vectors that are suitable for the purposes of the invention, plasmids, viral vectors of lentiviral type, Semliki, adenovirus, poxvirus, vaccine virus, baculovirus, bacterial vectors of the *salmonella* type and BCG may for example be cited.

"Necessary means for the expression" is taken to mean a protein, the term protein being used for any molecule of amino acids, such as protein, fusion protein, fragment of protein, peptide, polyprotein, polypeptide, etc., any means which make it possible to obtain the protein, such as especially a promoter, a transcription terminator, an origin of replication and preferably a selection marker. The means necessary for the expression of a peptide are linked in an operational manner to the nucleic acid sequence encoding for the peptide of interest.

"Linked in an operational manner" is taken to mean a juxtaposition of said necessary components for the expression and the gene encoding for the peptide of interest, which are in a relation such that it allows them to function in an expected manner. For example, there may exist supplementary bases between the promoter and the gene of interest as long as their functional relation is preserved.

The necessary means for the expression of a peptide may be homologous means, in other words included in the genome of the vector used, or instead may be heterologous. In the latter case, said means are cloned with the peptide of interest to be expressed.

Preferably, the promoter used in the Semliki vector and the lentiviral vector used as expression vector is a homologous promoter and is a cytomegolovirus (CMV) promoter.

Non limiting examples of heterologous promoters comprise especially (i) viral promoters such as the SV40 (Simian Virus 40) promoter, the promoter of the gene of the thymidine-kinase of the Herpes simplex virus (TK-HSV-1), the LTR of the Rous sarcoma virus (RSV), the cytomegolovirus (CMV) promoter and the adenovirus major late promoter (MLP), as well as (ii) any cell promoter which controls the transcription of genes encoding for peptides in higher eukaryotes, such as the promoter of the constitutive gene of phosphoglycerate-kinase (PGK) (Adra et al., 1987, Gene, 60: 65-74), the promoter of specific genes of the liver alpha1-antitrypsine and FIX and the specific promoter SM22 of the cells of the smooth muscle (Moessler et al., 1996, Development, 122: 2415-2425).

The invention particularly relates to an aforementioned vector, further comprising a lentiviral vector.

The object of the invention is more particularly an aforementioned vector, in which the lentiviral vector is the vector pLenti.

The latter has been disclosed previously, especially by Naldini, L., Blomer, U., Gallay, P., Ory, D., Mulligan, R., Gage, F. H., Verma, I. M., and Trono, D. (1996). In vivo gene delivery and stable transduction of nondividing cells by a lentiviral vector. Science 272(5259), 263-7.

Another object of the invention is an aforementioned vector, further comprising a defective viral vector derived from the genome of the Semliki Forest virus.

The latter have been disclosed previously, especially by Schlesinger, S., and T. M. Dubensky, Jr. 1999. Alphavirus vectors for gene expression and vaccines. Curr. Opin. Biotechnol. 10:434-439.

The object of the invention is especially an aforementioned vector, in which the defective viral vector derived from the genome of the Semliki Forest virus is the vector pSFV1, the latter being especially commercialised by Invitrogen.

In this respect, the object of the invention is more particularly an aforementioned vector, in which the hybrid nucleic acid molecule is composed:

of the nucleic acid sequence represented by SEQ ID NO: 11, or of a nucleic acid sequence having an homology of at least 78%, especially of at least 80%, particularly of at least 85%, and more particularly of at least 90%, with said sequence SEQ ID NO: 11, under the condition that the protein encoded by said nucleic acid sequence encoding for a fusion protein is capable of forming immunogenic non infectious subviral particles, vis-à-vis HCV and/or HBV, which vector is especially represented by the SEQ ID NO: 15, or of the nucleic acid sequence of a synthetic variant derived from the nucleic acid sequence represented by SEQ ID NO: 11, under the condition that the protein encoded by said nucleic acid sequence encodes for a fusion protein capable of forming immunogenic non infectious subviral particles, vis-à-vis HCV and/or HBV.

Another object of the invention is a vector derived from pSFV1 of sequence SEQ ID NO: 15, comprising a hybrid nucleic acid molecule (especially pit1-e1-sd of SEQ ID NO: 11) encoding for the aforementioned fusion protein (especially PIT1-E1-Sd of SEQ ID NO: 12), and for which:

the nucleic acid sequence encoding for the protein E1 is derived from HCV, and particularly from the HCV-1a isolate, and is the aforementioned sequence SEQ ID NO: 3 and, for which the nucleic acid sequence encoding for the S protein is derived from HBV, and particularly from the HBVadw isolate, and is the aforementioned sequence—SEQ ID NO: 1, said SEQ ID NO: 1 being grafted at the 5' side of the SEQ ID NO: 3 of E1, itself grafted at the 5' side of the nucleic acid sequence encoding for the transfer initiation peptide of the protein E1 (PIT1) included in the region constituted of the nucleic acid in position 837 to that in position 914 of HCV.

In this respect, the object of the invention is more particularly one of the aforementioned vectors, in which the hybrid nucleic acid molecule is composed:

of the nucleic acid sequence represented by SEQ ID NO: 13, or of a nucleic acid sequence having an homology of at least 80%, particularly of at least 85%, more particularly of at least 90%, and even more particularly of at least 95%, with said sequence SEQ ID NO: 13, under the condition that said nucleic acid sequence encodes for a peptide capable of forming immunogenic non infectious subviral particles, vis-à-vis the HBV and/or HCV virus, which vector is especially represented by the SEQ ID NO: 16, of the nucleic acid sequence of a synthetic variant, derived from said SEQ ID NO: 13, under the condition that the protein encoded by said nucleic acid sequence encodes for a peptide capable of forming immunogenic non infectious subviral particles, vis-à-vis the HBV and/or HCV virus.

Another object of the invention is a vector of SEQ ID NO: 16, comprising a hybrid nucleic acid molecule (especially pit1-e1-sd of SEQ ID NO: 13) encoding for the aforementioned fusion protein (especially PIT1-E1-Sd of SEQ ID NO: 14), and for which:

the nucleic acid sequence encoding for the protein E2 is derived from HCV, and particularly from the HCV-1a isolate, and is the aforementioned sequence SEQ ID NO: 5 and, for which the nucleic acid sequence encoding for the S protein is derived from HBV, and particularly from the HBVadw isolate, and is the aforementioned sequence SEQ ID NO: 1, said SEQ ID NO: 1 being grafted at the 5' side of the SEQ ID NO: 5 of E2, itself grafted at the 5' side of the nucleic acid sequence encoding for the transfer initiation peptide of the protein E2 (PIT2) included in the region constituted of the nucleic acid in position 1437 to that in position 1490 of HCV.

The invention also relates to an aforementioned vector, comprising a hybrid nucleic acid molecule composed of the following three nucleic acid sequences:

a)—on the 3' side, a first nucleic acid sequence encoding for the S protein deleted of the transmembrane domain thereof located at the N-terminal end thereof (Sd), of a hepatitis B virus (HBV) isolate, or of a nucleic acid sequence having an homology of at least 91%, especially of at least 93%, particularly of at least 95%, and more particularly of at least 97%, with said nucleic acid sequence of the N-terminal deleted S protein, under the condition that said nucleic acid sequence encodes for a peptide capable of forming immunogenic non infectious subviral particles, vis-à-vis the HBV virus, or of the nucleic acid sequence of a natural variant derived from an isolate of the HCV virus or of a synthetic variant derived from said nucleic acid sequence encoding for the deleted S protein (Sd), under the condition that the protein encoded by said nucleic acid sequence encodes for a peptide capable of forming immunogenic non infectious subviral particles, vis-à-vis the HBV virus, and, b)—at the 5' end of said first nucleic acid sequence, a second nucleic acid sequence encoding for the transmembrane domain and the ectodomain of at least one envelope protein E1 or E2, of a hepatitis C virus isolate, or a nucleic acid sequence having an homology of at least 78%, especially of at least 80%, particularly of at least 85%, and more particularly of at least 90%, with said nucleic acid sequence encoding for one of said proteins E1 or E2, of a hepatitis C virus isolate, under the condition that the protein encoded by said nucleic acid sequence encodes for a peptide immunogenic vis-à-vis the hepatitis C virus, or the nucleic acid sequence of a natural variant derived from an isolate of the HCV virus or of a synthetic variant derived from said second nucleic acid sequence encoding for an envelope protein E1 or E2, under the condition that the protein encoded by said nucleic acid sequence encodes for a peptide immunogenic vis-à-vis the hepatitis C virus, said second sequence being chosen from the sequences encoding for the protein E1, for the protein E2 or for a fusion peptide comprising the protein E1 and the protein E2, and, c)—at the 5' end of said second nucleic acid sequence, a third nucleic acid sequence encoding for a transfer initiation peptide (PIT) of a hepatitis C virus isolate, or a nucleic acid sequence of a natural variant derived from an isolate of the HCV virus, or of a synthetic variant, derived from said nucleic acid sequence of the protein encoding for a transfer initiation peptide (PIT), under the condition that the transfer initiation peptide encoding by said nucleic acid sequence, maintains the ability of addressing, after translation, said fusion protein to the endoplasmic reticulum so that it is correctly glycosylated and that its three dimensional conformation has the least alteration possible, and/or that its antigenic characteristics are at best preserved with regard to wild-type proteins, or, any nucleic acid sequence encoding for a peptide capable of addressing, after translation, said fusion protein to the endoplasmic reticulum so that it is correctly glycosylated and that its three dimensional conformation has the least possible alterations, and/or that its antigenic characteristics are at best preserved with regard to wild-type proteins.

Advantageously, another object of the invention is an aforementioned vector, in which the first and the second nucleic acid sequence of the aforementioned hybrid nucleic acid molecule (especially e1-sd or e1-e2-sd) and encoding for the aforementioned immunogenic fusion protein (especially E1-Sd or E2-Sd) are contiguous, and the 5' end of the first nucleic acid sequence is bonded in a covalent manner to the 3' end of the second nucleic acid sequence.

According to another advantageous aspect, the invention relates to the aforementioned vector (especially a lentiviral vector, such as the vector pLenti, or a defective viral vector derived from the genome of the Semliki Forest virus, such as the vector pSFV1) for which a nucleotide sequence, encoding for a binding peptide, links said first and second nucleotide sequences encoding for the aforementioned immunogenic fusion protein (especially E1-Sd or E2-Sd), said sequence nucleotide being composed of 3 nucleic acids, or 6 nucleic acids, or 9 nucleic acids, or 12 nucleic acids, or 15 nucleic acids, under the condition that said nucleotide sequence, encoding for a binding peptide, does not alter the capacity of the aforementioned immunogenic fusion protein (especially E1-Sd or E2-Sd), to self-assembly into subviral particles, in the presence of the wild-type S protein, and that the latter also conserves the immunogenic properties vis-à-vis the HCV virus, and/or, the HBV virus.

Advantageously, the aforementioned vector comprises the first nucleic acid sequence encoding for the N-terminal deleted S protein, of HBV, and especially of the HBVadw isolate of the hepatitis B virus, said sequence being:

a nucleic acid sequence bounded by the contiguous nucleic acids located in positions 1630 to 2241 of HBV, and particularly of the HBVadw isolate, and especially the nucleic acid sequence represented by the SEQ ID NO: 1, or a nucleic acid sequence having an homology of at least 91%, especially of at least 93%, particularly of at least 95%, and more particularly of at least 97%, with said SEQ ID NO: 1, under the condition that the protein encoded by said nucleic acid sequence maintains the ability to form immunogenic non infectious subviral particles, vis-à-vis the hepatitis B virus, or the nucleic acid sequence of a natural variant derived from an isolate of the HBV virus or of a synthetic variant derived from the SEQ ID NO: 1, under the condition that the protein encoded by said nucleic acid sequence maintains the ability to form immunogenic non infectious subviral particles, vis-à-vis the hepatitis B virus.

A more particular object of the invention resides in the aforementioned vector (especially a lentiviral vector, such as the vector pLenti, or a defective viral vector derived from the genome of the Semliki Forest virus, such as the vector pSFV1) comprising an aforementioned hybrid nucleic acid molecule (especially e1-sd or e2-sd, or e1-e2-sd, pit1-e1-sd or pit2-e2-sd) encoding for a fusion protein (especially E1-Sd or E2-Sd, or E1-E2-Sd, PIT1-E1-Sd or PIT2-E2-Sd) for which said nucleic acid sequence encoding for the deleted S protein of the HBV is that of the HBVadw isolate, and has for sequence SEQ ID NO: 1.

According to a particular aspect of the invention, the aforementioned vector comprises the second nucleic acid sequence encoding for the transmembrane domain and the ectodomain of the protein E1 of HCV, and particularly of the HCV-1a isolate, which is located on the 5' side of said molecule, and which is composed:

of a nucleic acid sequence bounded by the contiguous nucleic acids located from the position 915 to the position 1490, and particularly from the position 915 to the position 1481, of the genome of HCV, and particularly the HCV-1a isolate, and especially the nucleic acid sequence represented by the SEQ ID NO: 3, or of a nucleic acid sequence having an homology of at least 75%, especially of at least 80%, particularly of at least 85%, and more particularly of at least 90%, with said nucleic acid sequence encoding for the protein E1, under the condition that the protein encoded by said nucleic acid sequence conserves the immunogenic properties vis-à-vis the hepatitis C virus, or of the nucleic acid sequence of a natural variant derived from an isolate of the HCV virus or of a synthetic variant, derived from said nucleic acids encoding for said protein E1, under the condition that the protein encoded by said nucleic acid sequence conserves the immunogenic properties vis-à-vis the hepatitis C virus.

A more particular object of the invention resides in the aforementioned vector (especially a lentiviral vector, such as the vector pLenti, or a defective viral vector derived from the genome of the Semliki Forest virus, such as the vector pSFV1) comprising an aforementioned hybrid nucleic acid molecule (especially e1-sd, or e1-e2-sd, pit1-e1-sd) encoding for a fusion protein (especially E1-Sd, or E1-E2-Sd, PIT1-E1-Sd) for which said nucleic acid sequence encoding for the protein E1 of the HCV is that of the HCV-1a isolate, and has for sequence SEQ ID NO: 3.

According to an advantageous aspect of the invention, the aforementioned vector comprises the second nucleic acid sequence encoding for the transmembrane domain and the ectodomain of the protein E2 of HCV, and particularly of the HCV-1a isolate, which is located on the 5' side of said molecule, and which is composed:

of a nucleic acid sequence bounded by the contiguous nucleic acids located from the position 1491 to the position 2579, and particularly from the position 1491 to the position 2570, of the genome of HCV, and particularly of the HCV-1a isolate, and especially the nucleic acid sequence represented by the SEQ ID NO: 5, or of a nucleic acid sequence having a homology of at least 78%, especially of at least 80%, particularly of at least 85%, and more particularly of at least 90%, with said nucleic acid sequence encoding for the protein E2, under the condition that the protein encoded by said nucleic acid sequence conserves the immunogenic properties vis-à-vis the hepatitis C virus, or of the nucleic acid sequence of a natural variant, derived from an isolate of the HCV virus, or of a synthetic variant derived from said nucleic acids encoding for said protein E2, under the condition that the protein encoded by said nucleic acid sequence conserves the immunogenic properties vis-à-vis the hepatitis C virus.

A more particular object of the invention resides in the aforementioned vector (especially a lentiviral vector, such as the vector pLenti, or a defective viral vector derived from the genome of the Semliki Forest virus, such as the vector pSFV1) comprising an aforementioned hybrid nucleic acid molecule (especially e2-sd, or e1-e2-sd, pit2-e2-sd) encoding for a fusion protein (especially E2-Sd, or E1-E2-Sd, PIT2-E2-Sd) for which said nucleic acid sequence encoding for the protein E2 of the HCV is that of the HCV-1a isolate, and has for sequence SEQ ID NO: 5.

Another object of the invention is a subviral, chimeric, immunogenic and non infectious envelope particle, comprising the following proteins:

the protein composed of the wild-type S protein of the surface antigen of a hepatitis B virus (HBV) isolate, and, at least one aforementioned immunogenic fusion protein.

The term "chimeric subviral particle" is taken to mean any subviral particle comprising at least the wild-type S protein of HBV and an aforementioned immunogenic fusion protein resulting from the self-assembly of the wild-type S protein, or the assembly of an aforementioned fusion protein, in the presence of the wild-type S protein.

Advantageously, the immunogenic fusion protein of the aforementioned immunogenic chimeric subviral particle is:

the amino acid sequence represented by the SEQ ID NO: 8, or an amino acid sequence having a percentage of identity of at least 88%, especially of at least 90%, particularly of at least 92%, and more particularly of at least 95%, with said SEQ ID NO: 8, under the condition that said amino acid sequence maintains the ability to form immunogenic non infectious subviral particles, vis-à-vis HCV and/or vis-à-vis HBV, or the amino acid sequence of a natural variant derived from an isolate of the HCV virus and/or of the HBV virus or of a synthetic variant, derived from said SEQ ID NO: 8, under the condition that said amino acid sequence maintains the ability to form immunogenic non infectious subviral particles, vis-à-vis HCV and/or vis-à-vis HBV.

Another object of the invention is an aforementioned immunogenic chimeric subviral particle comprising an aforementioned fusion protein, and especially the fusion protein E1-Sd of SEQ ID NO: 8, or E1-E2-Sd, and for which the sequence of the protein E1 is especially the aforementioned SEQ ID NO: 4, and is especially grafted at the C-terminal of the amino acid sequence of the S protein (Sd) deleted of the sequence SEQ ID NO: 2.

According to a particular aspect of the invention, the immunogenic fusion protein of the aforementioned immunogenic chimeric subviral particle is composed of:
the amino acid sequence represented by the SEQ ID NO: 10, or
an amino acid sequence having a percentage of identity of at least 86%, especially of at least 88%, particularly of at least 92%, and more particularly of at least 95%, with SEQ ID NO: 10, under the condition that said amino acid sequence maintains the ability to form immunogenic non infectious subviral particles, vis-à-vis the hepatitis B virus and/or vis-à-vis the hepatitis C virus, or
the amino acid sequence of a synthetic variant, derived from the SEQ ID NO: 10, under the condition that said amino acid sequence maintains the ability to form immunogenic non infectious subviral particles, vis-à-vis the hepatitis B virus and/or vis-à-vis the hepatitis C virus.

Another object of the invention is an aforementioned immunogenic chimeric subviral particle comprising an aforementioned fusion protein, and especially the fusion protein E1-Sd of SEQ ID NO: 10, or E1-E2-Sd, and for which the sequence of the protein E1 is especially the aforementioned SEQ ID NO: 6, and is especially grafted at the C-terminal of the amino acid sequence of the S protein (Sd) deleted of sequence SEQ ID NO: 2.

According to an advantageous aspect of the invention, the aforementioned immunogenic chimeric subviral particle comprises the following two fusion proteins:
the amino acid sequence represented by the SEQ ID NO: 8, or
an amino acid sequence having a percentage of identity of at least 88%, especially of at least 90%, particularly of at least 92%, and more particularly of at least 95%, with said SEQ ID NO: 8, under the condition that said SEQ ID NO: 8 encodes for a protein that maintains the ability to form immunogenic non infectious subviral particles, vis-à-vis the hepatitis B virus and/or vis-à-vis the hepatitis C virus, or
the amino acid sequence of a synthetic variant, derived from the SEQ ID NO: 8, under the condition that said SEQ ID NO: 8 encodes for a protein that maintains the ability to form immunogenic non infectious subviral particles, vis-à-vis the hepatitis B virus and/or vis-à-vis the hepatitis C virus, and
the amino acid sequence represented by the SEQ ID NO: 10, or
an amino acid sequence having a percentage of identity of at least 86%, especially of at least 88%, particularly of at least 90%, and more particularly of at least 95%, with SEQ ID NO: 10, under the condition that said amino acid sequence maintains the ability to form immunogenic non infectious subviral particles, vis-à-vis the hepatitis B virus and/or vis-à-vis the hepatitis C virus, or
the amino acid sequence of a synthetic variant, derived from the SEQ ID NO: 10, under the condition that said amino acid sequence maintains the ability to form immunogenic non infectious subviral particles, vis-à-vis the hepatitis B virus and/or vis-à-vis the hepatitis C virus.

Another object of the invention is an aforementioned immunogenic chimeric subviral particle comprising two aforementioned fusion proteins (especially E1-Sd of SEQ ID NO: 8, or E1-E2-Sd; and E2-Sd of SEQ ID NO: 10).

The invention also relates to an aforementioned immunogenic chimeric subviral particle, in which the immunogenic fusion protein comprises at least one of the envelope proteins (E1) of a hepatitis C virus isolate, said protein being composed:
of an amino acid sequence corresponding to the residues of amino acids located in the region constituted of the amino acid in position 192 to that in position 380 of the wild-type S protein of HCV, and particularly of the HCV-1a isolate, or
of an amino acid sequence having a percentage of identity of at least 75%, especially of at least 80%, particularly of at least 85%, and more particularly of at least 90%, with said sequence of the wild-type proteins E1 of an isolate of HCV, under the condition that said amino acid sequence conserves the immunogenic properties vis-à-vis the hepatitis C virus, or
of the amino acid sequence of a natural variant derived from an isolate of the HCV virus or of a synthetic variant, derived from said protein E1, under the condition that said amino acid sequence conserves the immunogenic properties vis-à-vis the hepatitis C virus.

Another object of the invention is an aforementioned immunogenic chimeric subviral particle comprising an aforementioned fusion protein (especially E1-Sd, or E1-E2-Sd or PIT1-E1-E2-Sd, or PIT2-E2-E1-Sd), for which the sequence of the protein E1 is derived from the HCV-1a isolate.

Another object of the invention is an aforementioned immunogenic chimeric subviral particle, in which the immunogenic fusion protein comprises at least one of the envelope proteins of a hepatitis C virus isolate, said protein being composed of sequences of amino acids chosen from the following:
an amino acid sequence corresponding to the residues of amino acids located in the region constituted of the amino acid in position 384 to that in position 743 of the wild-type S protein E2 of HCV, and particularly of the HCV-1a isolate, or
an amino acid sequence having a percentage of identity of at least 78%, especially of at least 80%, particularly of at least 85%, and more particularly of at least 90%, with said sequences of the wild-type proteins E2 of said HCV isolate, under the condition that said amino acid sequence conserves the immunogenic properties vis-à-vis the hepatitis C virus, or
the amino acid sequence of a natural variant derived from an isolate of the HCV virus or of a synthetic variant, derived from said protein E2, under the condition that said amino acid sequence conserves the immunogenic properties vis-à-vis the hepatitis C virus.

Another object of the invention is an aforementioned immunogenic chimeric subviral particle comprising an aforementioned fusion protein (especially E2-Sd, or E1-E2-Sd or PIT1-E1-E2-Sd), for which the sequence of the protein E2 is derived from the HCV-1a isolate.

According to a particular aspect, the invention also relates to an aforementioned immunogenic chimeric subviral particle, comprising the following two fusion proteins:
the fusion protein comprising the amino acid sequence constituted of the amino acid in position 192 to that in position 383, and particularly in position 192 to that in position 380 of the wild-type E1 protein of HCV, and particularly of the HCV-1a isolate; or
an amino acid sequence having a percentage of identity of at least 75%, especially of at least 80%, particularly of at least 85%, and more particularly of at least 90%, with said sequence of the wild-type proteins E1 of an isolate of HCV, under the condition that said amino acid sequence conserves the immunogenic properties vis-à-vis the hepatitis C virus, or the amino acid sequence of a natural variant derived from an isolate of the HCV virus or of a synthetic variant, derived from said protein E1, under the condition that said amino acid sequence conserves the immunogenic properties vis-à-vis the hepatitis C virus, and the fusion protein comprising the amino acid sequence composed of the amino acid in position 384 to that in position 746, and particularly in position 384 to that in position 743 of the wild-type E2 protein of HCV, and particularly the HCV-1a isolate, or an amino acid sequence having a percentage of identity of at least 78%, especially of at least 80%, particularly of at least 85%, and more particularly of at least 90%, with said sequences of the wild-type proteins E2 of said HCV isolate, under the condition said amino acid sequence conserves the immunogenic properties vis-à-vis the hepatitis C virus, or the amino acid sequence of a natural variant derived from an isolate of the HCV virus or of a synthetic variant, derived from said protein E2, under the condition that said amino acid sequence conserves the immunogenic properties vis-à-vis the hepatitis C virus.

Another object of the invention is an aforementioned immunogenic chimeric subviral particle comprising two aforementioned fusion proteins (especially E1-Sd, or PIT1-E1-Sd or E2-Sd or PIT1-E1-Sd or E1-E2-Sd or PIT1-E1-E2-Sd).

Another object of the invention is an immunogenic composition comprising as active ingredient at least one compound chosen from:

an aforementioned fusion protein,
a hybrid nucleic acid molecule described previously,
an aforementioned vector comprising said hybrid nucleic acid molecule,
a chimeric subviral particle described above,
and, a pharmaceutically acceptable vehicle.

According to a particular embodiment of the invention, the pharmaceutical composition also contains a pharmaceutically acceptable vehicle, of which those skilled in the art will easily determine the nature and the quantity to use as a function of usual parameters and the constituents of the desired pharmaceutical composition, the pharmaceutical form and the mode of administration.

The pharmaceutical compositions of the invention are suitable for oral, sublingual, sub-cutaneous, intramuscular, intravenous, topic, local, intra-tracheal, intra-nasal, transdermal, rectal, intraocular, intra-aulicular administration, said active ingredient being able to be administered in unit administration form.

The unit administration forms may for example be tablets, capsules, granules, powders, injectable solutions or oral suspensions, transdermal patches, sublingual, buccal, intra-tracheal, intraocular, intra-nasal, intra-auricular administration forms, by inhalation, topical forms of administration, transdermal, sub-cutaneous, intramuscular or intravenous, rectal forms of administration or implants. For topical administration, creams, gels, ointments, lotions or eye drops may be envisaged.

Advantageously, the aforementioned immunogenic composition comprises an active ingredient chosen from at least one of the following three compounds:

a)—an aforementioned fusion protein composed of:
the amino acid sequence represented by the SEQ ID NO: 8, or
an amino acid sequence having a percentage of identity of at least 88%, especially of at least 90%, particularly of at least 92%, and more particularly of at least 95%, with SEQ ID NO: 8, under the condition that said amino acid sequence maintains the ability to form immunogenic non infectious subviral particles, vis-à-vis the hepatitis B virus and/or vis-à-vis the hepatitis C virus, or
the amino acid sequence of a synthetic variant, derived from the SEQ ID NO: 8, under the condition that said amino acid sequence maintains the ability to form immunogenic non infectious subviral particles, vis-à-vis the hepatitis B virus and/or vis-à-vis the hepatitis C virus, b)—a hybrid nucleic acid molecule composed of:
the nucleic acid sequence represented by SEQ ID NO: 11, or
a nucleic acid sequence having an homology of at least 78%, especially of at least 80%, particularly of at least 85%, and more particularly of at least 90%, with said sequence SEQ ID NO: 11, under the condition that the protein encoded by said nucleic acid sequence maintains the ability to form immunogenic non infectious subviral particles, vis-à-vis the hepatitis B virus and/or vis-à-vis the hepatitis C virus, or
the nucleic acid sequence of a synthetic variant, derived from the SEQ ID NO: 11, under the condition that the protein encoded by said nucleic acid sequence maintains the ability to form immunogenic non infectious subviral particles, vis-à-vis the hepatitis B virus and/or vis-à-vis the hepatitis C virus, or an aforementioned vector comprising said hybrid nucleic acid molecule, c)—a chimeric subviral particle, comprising the immunogenic fusion protein composed of:
the amino acid sequence represented by the SEQ ID NO: 8, or
an amino acid sequence having a percentage of identity of at least 88%, especially of at least 90%, particularly of at least 92%, and more particularly of at least 95%, with SEQ ID NO: 8, under the condition that said amino acid sequence maintains the ability to form immunogenic non infectious subviral particles, vis-à-vis HBV and HCV, or
the amino acid sequence of a synthetic variant, derived from the SEQ ID NO: 8, under the condition that said amino acid sequence maintains the ability to form immunogenic non infectious subviral particles, vis-à-vis HBV and HCV.

A particular object of the invention relates to one of the three following compounds:

a)—the aforementioned fusion protein comprising the protein E1 (especially E1-Sd, PIT1-E1-Sd, E1-E2-Sd, PIT1-E1-E2-Sd), a schematic representation of which is given in FIG. 3B, and which comprises the quasi-integrality of the protein E1 of the HCV, grafted at the N-terminal of the deleted S protein of HBV, or b)—the aforementioned hybrid nucleic acid molecule comprising a nucleic acid sequence encoding for the protein E1 (especially e1-sd, pit1-e1-sd, e1-e2-sd, pit1-e1-e2-sd), and which comprises the quasi-integrality of the nucleic acid sequence encoding for the protein E1 of the HCV, grafted at the 5' side of the nucleic acid sequence encoding for the deleted S protein of HBV, Of c)—the aforementioned subviral particle comprising the protein E1 (especially E1-Sd, PIT1-E1-Sd, E1-E2-Sd, PIT1-

E1-E2-Sd), a schematic representation of which is given in FIG. 3B, and which comprises the quasi-integrality of the protein E1 of the HCV, grafted at the N-terminal of the deleted S protein of HBV.

According to a particular aspect of the invention, the aforementioned immunogenic composition comprises an active ingredient chosen from at least one of the following compounds:

a)—a fusion protein composed of:
- the amino acid sequence represented by the SEQ ID NO: 10, or
- an amino acid sequence having a percentage of identity of at least 86%, especially of at least 88%, particularly of at least 90%, and more particularly of at least 95%, with SEQ ID NO: 10, under the condition that said amino acid sequence maintains the ability to form non infectious subviral particles, immunogenic vis-à-vis the hepatitis B virus and/or vis-à-vis the hepatitis C virus, or
- the amino acid sequence of a synthetic variant, derived from the SEQ ID NO: 10, under the condition that said amino acid sequence maintains the ability to form immunogenic non infectious subviral particles, vis-à-vis the hepatitis B virus and/or vis-à-vis the hepatitis C virus, b)—a hybrid nucleic acid molecule composed of:
- the nucleic acid sequence represented by SEQ ID NO: 13, or
- a nucleic acid sequence having an homology of at least 80%, especially of at least 85%, particularly of at least 90%, and more particularly of at least 95%, with said SEQ ID NO: 13, under the condition that the protein encoded by said nucleic acid sequence maintains the ability to form immunogenic non infectious subviral particles, vis-à-vis the hepatitis B virus and/or vis-à-vis the hepatitis C virus, or
- the nucleic acid sequence of a synthetic variant, derived from the SEQ ID NO: 13, under the condition that the protein encoded by said nucleic acid sequence maintains the ability to form immunogenic non infectious subviral particles, vis-à-vis the hepatitis B virus and/or vis-à-vis the hepatitis C virus; or an aforementioned vector comprising said hybrid nucleic acid molecule, c)—a chimeric subviral particle, comprising the immunogenic fusion protein composed of:
- the amino acid sequence represented by the SEQ ID NO: 10, or
- an amino acid sequence having a percentage of identity of at least 86%, especially of at least 88%, particularly of at least 90%, and more particularly of at least 95%, with SEQ ID NO: 10, under the condition that said amino acid sequence maintains the ability to form immunogenic non infectious subviral particles, vis-à-vis the hepatitis B virus and/or vis-à-vis the hepatitis C virus, or
- the amino acid sequence of a synthetic variant, derived from the SEQ ID NO: 10, under the condition that said amino acid sequence maintains the ability to form immunogenic non infectious subviral particles, vis-à-vis the hepatitis B virus and/or vis-à-vis the hepatitis C virus.

A particular object of the invention relates to one of the following three compounds:

a)—the aforementioned fusion protein comprising the protein E2 (especially E2-Sd, PIT2-E2-Sd, E1-E2-Sd, PIT1-E1-E2-Sd), a schematic representation of which is given in FIG. 3C, and which comprises the quasi-integrality of the protein E2 of the HCV, grafted at the N-terminal of the deleted S protein of HBV, or b)—the aforementioned hybrid nucleic acid molecule comprising a nucleic acid sequence encoding for the protein E2 (especially e2-sd, pit2-e2-sd, e1-e2-sd, pit1-e1-e2-sd), and which comprises the quasi-integrality of the nucleic acid sequence encoding for the protein E1 of the HCV, grafted at the 5' side of the nucleic acid sequence encoding for the deleted S protein of HBV, or c)—the aforementioned subviral particle comprising the protein E1 (especially E1-Sd, PIT-E1-Sd, E1-E2-Sd, PIT-E1-E2-Sd), and which comprises the quasi-integrality of the protein E2 of the HCV, grafted at the N-terminal of the deleted S protein of HBV.

According to an advantageous aspect of the invention, the aforementioned immunogenic composition comprises for active ingredient a chimeric subviral particle, comprising at least the two immunogenic fusion proteins composed of:
- the amino acid sequence represented by the SEQ ID NO: 8, or
- an amino acid sequence having a percentage of identity of at least 88%, especially of at least 90%, particularly of at least 92%, and more particularly of at least 95%, with said SEQ ID NO: 8, under the condition that said amino acid sequence maintains the ability to form immunogenic non infectious subviral particles, vis-à-vis the hepatitis B virus and/or vis-à-vis the hepatitis C virus, or
- the amino acid sequence of a synthetic variant, derived from the SEQ ID NO: 8, under the condition that said amino acid sequence maintains the ability to form immunogenic non infectious subviral particles, vis-à-vis the hepatitis B virus and/or vis-à-vis the hepatitis C virus, and,
- the amino acid sequence represented by the SEQ ID NO: 10, or
- an amino acid sequence having a percentage of identity of at least 86%, especially of at least 88%, particularly of at least 90%, and more particularly of at least 95%, with SEQ ID NO: 10 of E2-Sd, under the condition that said amino acid sequence maintains the ability to form immunogenic non infectious subviral particles, vis-à-vis the hepatitis B virus and/or vis-à-vis the hepatitis C virus, or
- the amino acid sequence of a synthetic variant, derived from the SEQ ID NO: 10, under the condition that said amino acid sequence maintains the ability to form immunogenic non infectious subviral particles, vis-à-vis the hepatitis B virus and/or vis-à-vis the hepatitis C virus.

A particular object of the invention relates to the aforementioned subviral particle comprising two aforementioned fusion proteins, one comprising:
- the protein E1 of the HCV (especially E1-Sd, PIT1-E1-Sd, E1-E2-Sd, PIT-E1-E2-Sd), and the protein E2 of HCV, grafted at the N-terminal of the deleted S protein of HBV, and the other
- the protein E2 of HCV (especially E2-Sd, PIT2-E2-Sd, E1-E2-Sd, PIT-E1-E2-Sd), grafted at the N-terminal of the deleted S protein of HBV.

[27]. According to a particularly advantageous aspect of the invention, the active ingredient of the aforementioned immunogenic composition is composed of the mixture comprising:
- at least two of the following fusion proteins:
  - one composed of:
    - the amino acid sequence represented by the SEQ ID NO: 8, or
    - an amino acid sequence having a percentage of identity of at least 88%, especially of at least 90%, particularly of at least 92%, and more particularly of at least 95%, with SEQ ID NO: 8, under the condition that said amino acid sequence maintains the ability to form immunogenic non infectious subviral particles, vis-à-vis the hepatitis B virus and/or vis-à-vis the hepatitis C virus, or the amino acid sequence of a synthetic variant, derived from the SEQ ID NO: 8, under the condition that said amino acid sequence maintains the ability to form immunogenic non infectious subviral particles, vis-à-vis the hepatitis B virus and/or vis-à-vis the hepatitis C virus;

the other composed of:
  the amino acid sequence represented by the SEQ ID NO: 10, or
  an amino acid sequence having a percentage of identity of at least 86%, especially of at least 88%, particularly of at least 90%, and more particularly of at least 95%, with SEQ ID NO: 10, under the condition that said amino acid sequence maintains the ability to form immunogenic non infectious subviral particles, vis-à-vis the hepatitis B virus and/or vis-à-vis the hepatitis C virus, or
  the amino acid sequence of a synthetic variant, derived from the SEQ ID NO: 10, under the condition that said amino acid sequence maintains the ability to form immunogenic non infectious subviral particles, vis-à-vis the hepatitis B virus and/or vis-à-vis the hepatitis C virus.

at least two molecules of the following hybrid nucleic acids:
one composed:
  of the nucleic acid sequence represented by SEQ ID NO: 11, or
  of a nucleic acid sequence having an homology of at least 78%, especially of at least 80%, particularly of at least 85%, and more particularly of at least 90%, with said sequence SEQ ID NO: 11, under the condition that the protein encoded by said nucleic acid sequence maintains the ability to form immunogenic non infectious subviral particles, vis-à-vis HCV and/or HBV, or
  the nucleic acid sequence of a synthetic variant derived from said sequence SEQ ID NO: 11, under the condition that the protein encoded by said nucleic acid sequence maintains the ability to form immunogenic non infectious subviral particles, vis-à-vis HCV and/or HBV, or an aforementioned vector comprising said hybrid nucleic acid molecule,
the other composed:
  of the nucleic acid sequence represented by SEQ ID NO: 13, or
  of a nucleic acid sequence having an homology of at least 80%, particularly of at least 85%, more particularly of at least 90%, and even more particularly of at least 95%, with said sequence SEQ ID NO: 13, under the condition that the protein encoded by said nucleic acid sequence maintains the ability to form immunogenic non infectious subviral particles, vis-à-vis HCV and/or HBV, or
  of the nucleic acid sequence of a synthetic variant, derived from said sequence SEQ ID NO: 13, under the condition that the protein encoded by said nucleic acid sequence maintains the ability to form immunogenic non infectious subviral particles, vis-à-vis HCV and/or HBV or an aforementioned vector comprising said hybrid nucleic acid molecule;

at least two of the following chimeric subviral particles:
  one comprising the immunogenic fusion protein composed of:
    the amino acid sequence represented by the SEQ ID NO: 8, or
    an amino acid sequence having a percentage of identity of at least 88%, especially of at least 90%, particularly of at least 92%, and more particularly of at least 95%, with said SEQ ID NO: 8, under the condition that said amino acid sequence maintains the ability to form immunogenic non infectious subviral particles, vis-à-vis HCV and/or vis-à-vis HBV, or
    of the amino acid sequence of a synthetic variant, derived from said SEQ ID NO: 8, under the condition that said amino acid sequence maintains the ability to form immunogenic non infectious subviral particles, vis-à-vis HCV and/or vis-à-vis HBV,
  one comprising the immunogenic fusion protein composed of:
    the amino acid sequence represented by the SEQ ID NO: 10, or
    an amino acid sequence having a percentage of identity of at least 86%, especially of at least 88%, particularly of at least 92%, and more particularly of at least 95%, with SEQ ID NO: 10, under the condition that said amino acid sequence maintains the ability to form immunogenic non infectious subviral particles, vis-à-vis HCV and/or vis-à-vis HBV, or
    the amino acid sequence of a synthetic variant, derived from the SEQ ID NO: 10,
    under the condition that said amino acid sequence maintains the ability to form immunogenic non infectious subviral particles, vis-à-vis HCV and/or vis-à-vis HBV.

A particular object of the invention relates to the mixture comprising the following compounds:

a)—at least two aforementioned fusion proteins, one comprising the protein E1 (especially E1-Sd of sequence SEQ ID NO: 8, or PIT1-E1-Sd, or E1-E2-Sd, or PIT1-E1-E2-Sd) the other comprising the protein E2 (especially E2-Sd of sequence SEQ ID NO: 10, or PIT2-E2-Sd, or E1-E2-Sd, or PIT1-E1-E2-Sd) of the HCV, the latter being grafted at the N-terminal of the deleted S protein of HBV, or b)—at least two aforementioned hybrid nucleic acid molecules, one comprising the nucleic acid sequence encoding for the protein E1 (especially pit1-e1-sd of sequence SEQ ID NO: 11, or e1-sd, or e1-e2-Sd, or pit1-e1-e2-sd), the other comprising the nucleic acid sequence encoding for the protein E1 (especially pit2-e2-sd of sequence SEQ ID NO: 13, or e2-sd, or e1-e2-Sd, or pit1-e1-e2-sd), the latter being grafted at the 5' side of the nucleic acid sequence encoding for the deleted S protein of HBV, or c)—at least two aforementioned subviral particles, one comprising the protein E1 (especially E1-Sd of sequence SEQ ID NO: 8, or PIT1-E1-Sd, or E1-E2-Sd, or PIT1-E1-E2-Sd) the other comprising the protein E2 (especially E2-Sd of sequence SEQ ID NO: 10, or PIT2-E2-Sd, or E1-E2-Sd, or PIT1-E1-E2-Sd) of HCV, the latter being grafted at the N-terminal of the deleted S protein of HBV.

Another object of the invention is the use of an aforementioned immunogenic composition for the manufacture of a medicine for the prophylactic and/or therapeutic treatment and/or for the prevention of hepatitis C.

The present invention also relates to the use of an aforementioned immunogenic composition for the manufacture of a medicine for the prophylactic and/or therapeutic treatment and/or for the prevention of hepatitis B.

Advantageously, the object of the present invention relates to the use of an aforementioned immunogenic composition for the manufacture of a medicine for the prophylactic and/or therapeutic treatment and/or for the prevention of hepatitis B and of hepatitis C.

Another object of the invention is a cell line that expresses the previously described chimeric, immunogenic non infectious subviral particles.

By way of examples of micro-organisms that are suitable for the purposes of the invention, may be cited yeasts, such as the following families: *Saccharomyces, Schizosaccharomyces, Kluveromyces, Pichia, Hanseluna, Yarowia, Schwaniomyces, Zygosaccharomyces, Saccharomyces cerevisiae, Saccharomyces carlsbergensis* and *Kluveromyces lactis* being preferred; and bacteria, such as *E. coli* and those of the following families: *Lactobacillus, Lactococcus, Salmonella, Streptococcus, Bacillus* and *Streptomyces*.

As examples of eukaryote cells, cells from animals such as mammals, reptiles, insects and equivalent may be cited. The preferred eukaryote cells are cells from the Chinese hamster (CHO cells), from the monkey (COS and Vero cells), the kidney of the dwarf hamster (BHK cells), the kidney of the pig (PK 15 cells) and the kidney of the rabbit (RK13 cells), human cell lines of the osteosacorma (143 B cells), human HeLa cell lines and human cell lines of the hepatoma (Hep G2 type cells), as well as insect cell lines (for example *Spodoptera frugiperda*).

Advantageously, the object of the present invention relates to an aforementioned cell line which is Chinese hamster ovary line known as CHO.

These have been previously disclosed, especially by Michel M L Pontisso P, Sobezak E, Malpiéce Y, Streeck R E, Tiollais P. Synthesis in animal cells of hepatitis B surface antigen particles carrying a receptor for polymerized human serum albumin. Proc Natl Acad Sci USA. 1984 December; 81(24):7708-12.

The present invention also relates to an aforementioned cell line, which is a yeast, said yeast may be especially *Saccharomyces cerevisae*.

Another object of the invention is a cell line disclosed above, which is the new-born hamster kidney cell line (BHK), and is particularly the new-born hamster kidney cell line (BHK-21).

The latter have been disclosed previously, especially by Goldman R D, Follett E A. Birefringent filamentous organelle in BHK-21 cells and its possible role in cell spreading and motility. Science. 1970 Jul. 17; 169(942):286-8.

According to a particular aspect, the invention also relates to a method of production of aforementioned chimeric, immunogenic non infectious subviral particles from an aforementioned cell line, comprising the following steps:

1—a step of TRANSDUCTION of the cells of the cell line with a lentiviral vector comprising a nucleic acid sequence encoding for the wild-type S protein of a hepatitis B virus (HBV) isolate, 2—a step of CULTURE of said cells in order to produce a cell line capable of expressing the wild-type subviral envelope particles of the hepatitis B virus.

3—a step of SELECTION of a clone having an optimal secretion of wild-type subviral envelope particles of the hepatitis B virus, 4—a step of OVER-TRANSDUCTION of said clone with an aforementioned vector, 5—a step of CULTURE of said cells in order to produce a cell line capable of expressing the aforementioned chimeric, immunogenic non infectious subviral particles, 6—a step of SELECTION of said cells capable of secreting in an optimal manner the aforementioned chimeric, immunogenic non infectious subviral particles, 7—a step of CULTURE of said clone for the production of the aforementioned chimeric, immunogenic non infectious subviral particles, and 8—a step of PURIFICATION of the subviral particles from the culture medium collected (centrifugation, ultra-centrifugation on gradients, collection of the positive fractions for the chimeric subviral particles, dialysis).

Table 1 provides a list of nucleic acid sequences and of amino acids disclosed in the present invention. By convention, lower case letters are used for nucleic acid sequences and upper case letters for amino acids sequences.

TABLE 1

LIST OF SEQUENCES

| Nucleic acids | Amino acids |
|---|---|
| SEQ ID N° 1: sd | SEQ ID N° 2: Sd |
| SEQ ID N° 3: e1 | SEQ ID N° 4: E1 |
| SEQ ID N° 5: e2 | SEQ ID N° 6: E2 |
| SEQ ID N° 7: e1-sd | SEQ ID N° 8: E1-Sd |
| SEQ ID N° 9: e2-sd | SEQ ID N° 10: E2-Sd |
| SEQ ID N° 11: pit1-e1-sd | SEQ ID N° 12: PIT1-E1-Sd |
| SEQ ID N° 13: pit2-e2-sd | SEQ ID N° 14: PIT2-E2-Sd |
| SEQ ID N° 15: Vector with pit1-e1-sd | / |
| SEQ ID N° 16: Vector with pit2-e2-sd | / |

Other characteristics and advantages of the invention will become clearer on reading the following description of a preferential embodiment, given by way of simple illustrative and non limiting example, and by referring to the appended figures, among which:

FIG. 1 schematises the topology of a fragment of the polyprotein of the HCV virus of more than 3 000 amino acids. The cleavages carried out by the cellular peptidases (✂) result in the maturation of said polyprotein especially into structural proteins (capsid, envelope E1 and E2). The numbers indicate the position of the residues of amino acids bounding the domains of the different structural proteins of the polyprotein.

FIGS. 2A and 2B schematise the transmembrane topology of the wild-type S protein of the HBV virus.

FIG. 2A schematises the 226 residues of amino acids of the wild-type S protein of the HBV virus, which comprises especially four transmembrane domains, represented by grey vertical rectangles, and the N- and C-terminal ends of which are oriented towards the light of the RE. In the case of the HBVadw isolate, this protein of around 25 kD comprises 226 residues of amino acids.

FIG. 2B represents a subviral particle obtained following the self-assembly of said wild-type S protein.

FIGS. 3A to 3C represent the co-expression of the fusion proteins E1-Sd (FIG. 3B) or E2-Sd (FIG. 3C) which, in the presence of the wild-type S protein (FIG. 3B), assemble themselves into chimeric subviral particles of the present invention.

FIG. 3A represents the wild-type S protein of HBV, which self-assembles into subviral particles.

FIG. 3B represents the fusion protein E1-Sd, which results from the substitution of the transmembrane domain located at the N-terminal end of the wild-type S protein by the transmembrane domain of the envelope protein E1 of the HCV virus, represented by a black vertical rectangle, and by the ectodomain of E1, represented by dotted lines; then schematises the assembly of said fusion protein E1-Sd, in the presence of the wild-type S protein, into subviral particles S+E1-Sd.

According to the particular but non limiting embodiment of the invention, the fusion protein E1-Sd of around 50 kD comprises 393 residues of amino acids derived from the protein E1 and of the S domain. The residues 192 to 380 of the complete protein E1 are linked to the N-terminal end of the deleted S protein composed of residues 23 to 226 of the wild-type S protein.

FIG. 3C represents the fusion protein E2-Sd, which results from the substitution of the transmembrane domain located at the N-terminal end of the wild-type S protein by the transmembrane domain of the envelope protein E2 of the HCV virus, represented by a white vertical rectangle, and by the ectodomain of E2, represented by dotted lines; then schematises the assembly of said fusion protein E2-Sd, in the presence of the wild-type S protein, into subviral particles S+E2-Sd.

According to the particular but non limitative embodiment of the invention, the fusion protein E2-Sd of around 85 kD comprises 564 residues of amino acids derived from the protein E2 and of the domain S. The residues 384 to 743 of the complete protein E2 are linked to the N-terminal end of the deleted S protein composed of residues 23 to 226 of the wild-type S protein.

FIGS. 4A to 4E schematise the topology of the wild-type envelope S proteins of the HBV, E1 and E2 of the HCV, as well as the fusion proteins E1-Sd and E2-Sd.

FIG. 4A represents the topology of the wild-type envelope protein E1 of the HCV, which is composed of a unique transmembrane domain (black vertical rectangle) and a wide ectodomain oriented towards the light of the RE. In the case of the HCV1a isolate, this protein of around 35 kD comprises 192 residues of amino acids.

FIG. 4B represents the topology of the wild-type envelope protein E2 of the HCV, which is composed of a unique transmembrane domain (white vertical rectangle) and a large ectodomain oriented towards the light of the RE. In the case of the HCV1a isolate, this protein of around 70 kD comprises 363 residues of amino acids.

FIG. 4C represents the topology of the wild-type envelope S protein of the HBV, which comprises especially four transmembrane domains (grey vertical rectangles).

FIG. 4D represents the DNA sequence of the hybrid nucleic acid molecule pit1-e1-sd, composed of its 5' to 3' end:
the sequence encoding for the transfer initiation peptide PIT1 of the HCV virus,
the sequence encoding for the whole of the ectodomain of the protein E1 and the sequence encoding for the transmembrane domain of the protein E1 deleted of the last 3 codons of the 3' end of the HCV virus,
the sequence encoding for the deleted S protein of the HBV virus, and its use for the production of the fusion protein E1-Sd of the invention.

FIG. 4E represents the DNAc sequence of the hybrid nucleic acid molecule pit2-e2-sd, composed of its 5' to 3' end:
the sequence encoding for the transfer initiation peptide PIT2 of the HCV virus,
the sequence encoding for the whole of the ectodomain of the protein E2, the sequence encoding for the transmembrane domain of the protein E2 deleted of the last 3 codons of the 3' end of the HCV virus,
the sequence encoding for the deleted S protein of the HBV virus,
and its use for the production of the fusion protein E2-Sd of the invention.

Figure 1:
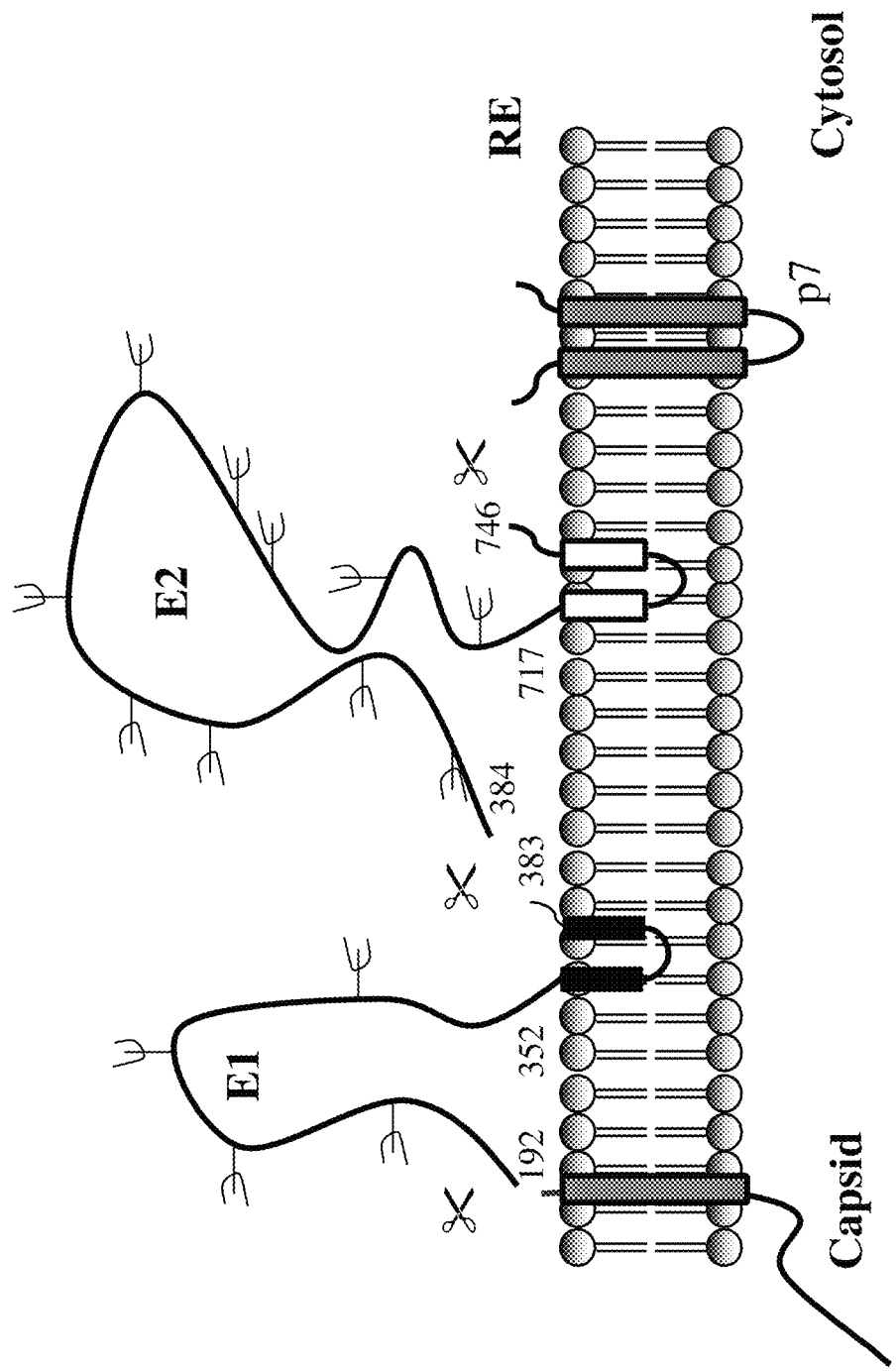
Figure 2A:
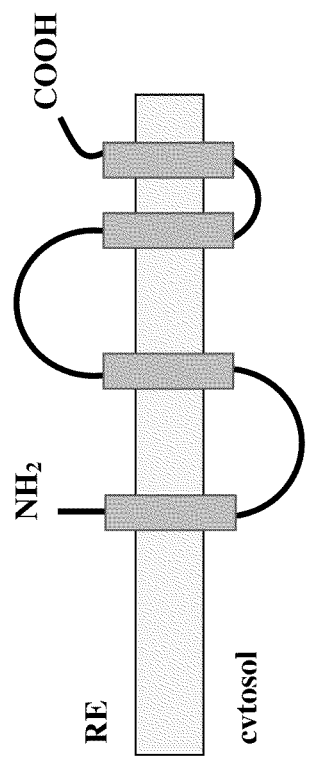
Figure 2B:
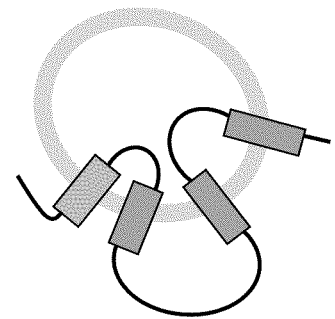
Figure 5:
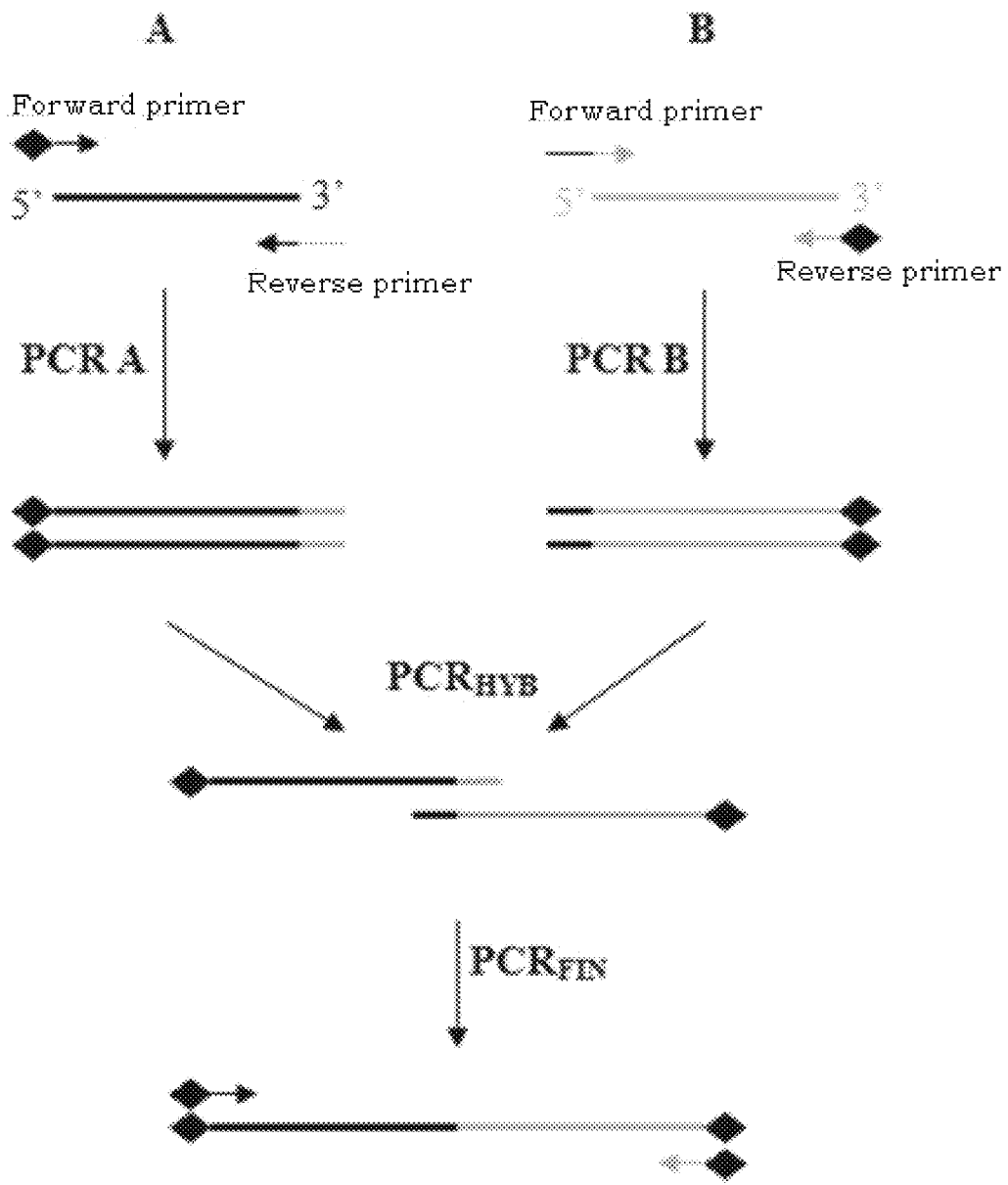

FIG. 5 schematises the protocol used for obtaining DNAc encoding for the fusion proteins of the invention. The sequence encoding for the proteins E1 and E2 is represented by a black line (sequence A). The sequence encoding for the deleted S protein is represented by a grey line (sequence B). The BamHI restriction site is represented by a black diamond. The forward and reverse primers used for the amplification of the nucleic acid sequences e1-sd A, e1-sd B, e2-sd A and e2-sd B are listed in table x.

Figure 6A:
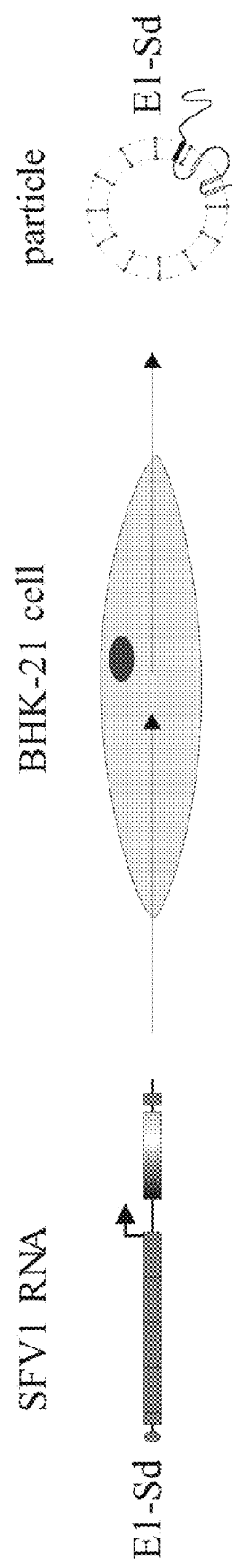
Figure 6B:
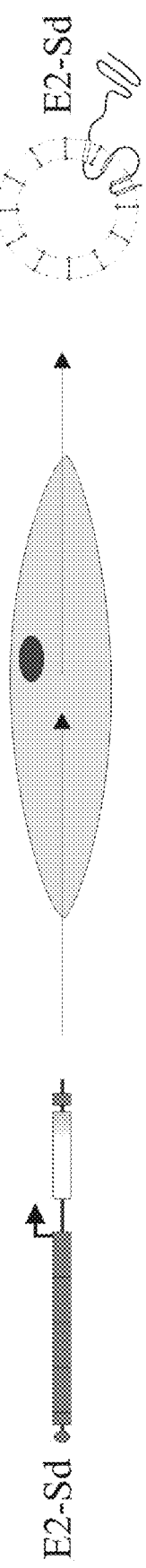

FIGS. 6A and 6B propose a schematic representation of the experimental protocol for the transitory production of one of the fusion proteins of the invention E1-Sd or E2-Sd in Semliki/BHK-21 cells system.

FIG. 6A shows that the RNA derived from the plasmid pSFV1-E1-Sd is transfected into BHK-21 cells with the aim of obtaining the production of chimeric subviral envelope particles E1-Sd.

FIG. 6B shows that the RNA derived from the plasmid pSFV1-E2-Sd is transfected into the BHK-21 cells with the aim of obtaining the production of chimeric subviral envelope particles E2-Sd.

Figure 6D:
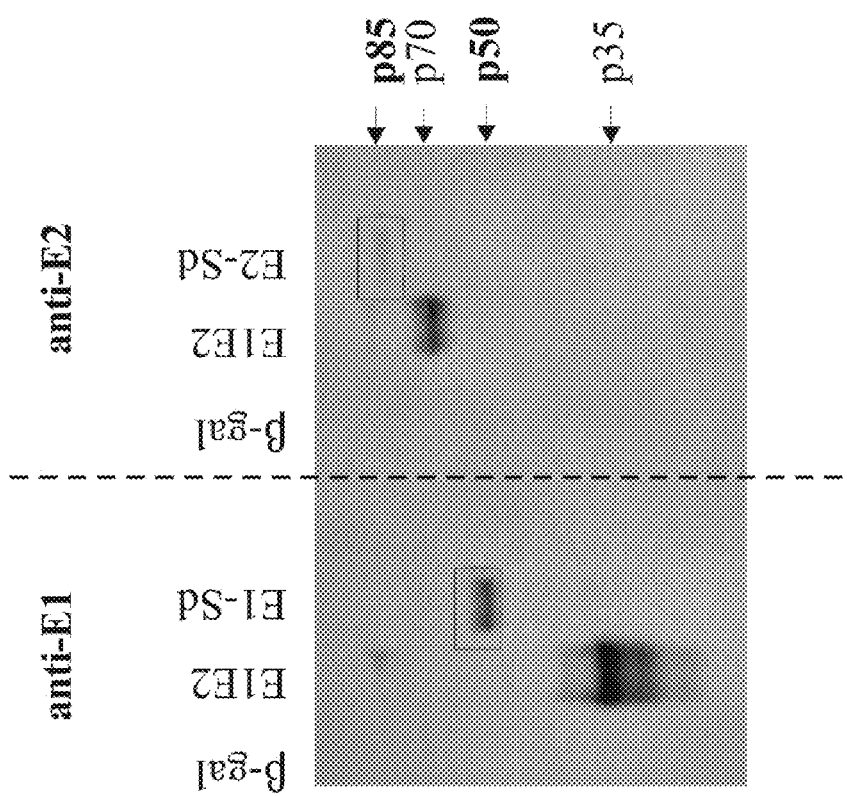
Figure 6C:
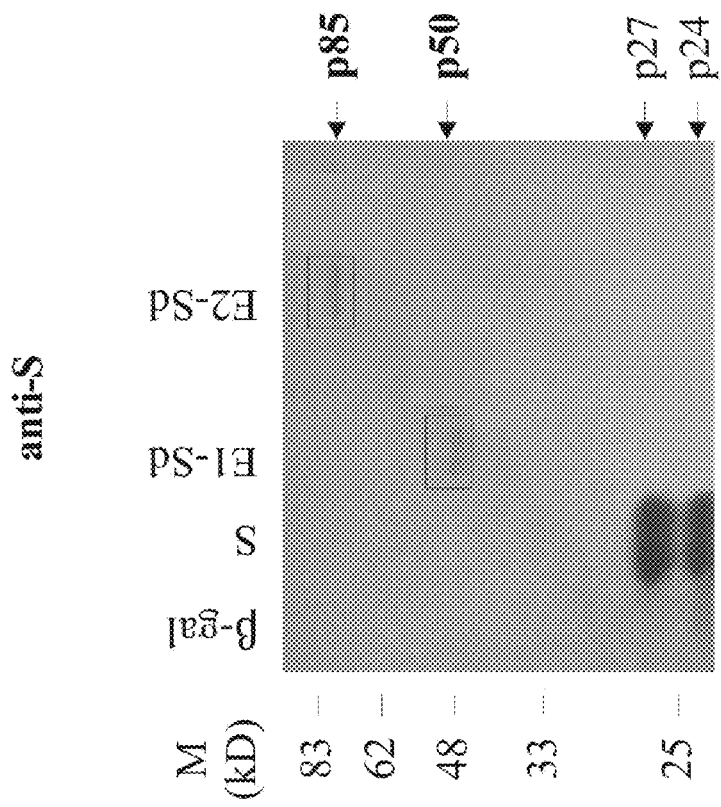

FIGS. 6C and 6D show the Western-blot revealed either with an anti-S (6C) antibody, or with an anti-E1 and anti-E2 (6D) antibody, on the lysates of cells transfected by the RNA derived from plasmids pSFV1-E1-Sd and pSFV1-E2-Sd.

FIG. 6C shows that the fusion proteins E1-Sd and E2-Sd (framed strips) are detected at the sizes of 50 kD and 85 kD respectively, corresponding to the theoretical sizes. M: molecular weight marker (kD).

FIG. 6D shows that the fusion proteins E1-Sd and E2-Sd (framed strips) are detected at the sizes of 50 kD and 85 kD respectively, by the anti-E1 and anti-E2 antibodies respectively. M: molecular weight marker (kD).

Figure 7A:
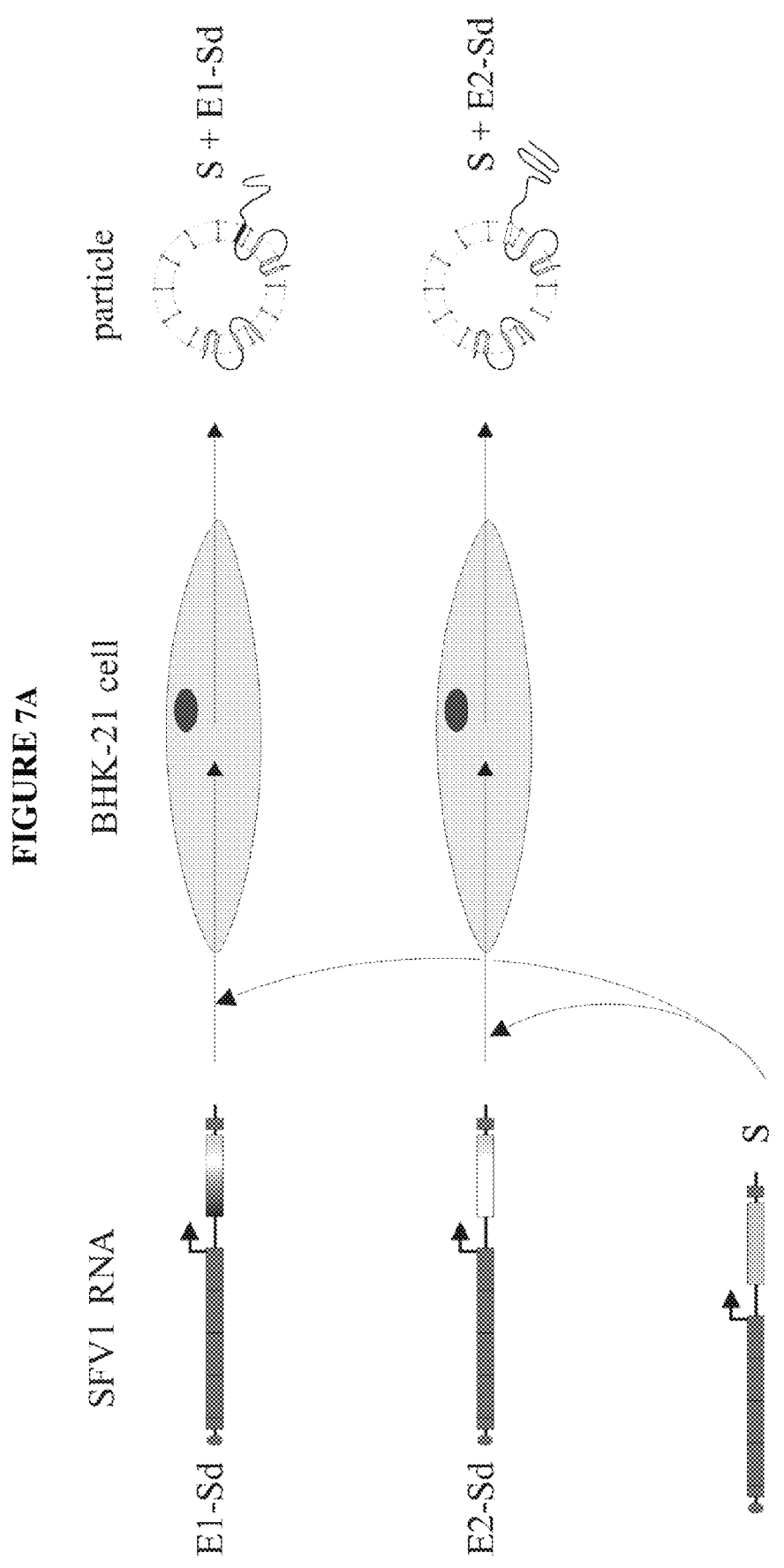
Figure 7B:
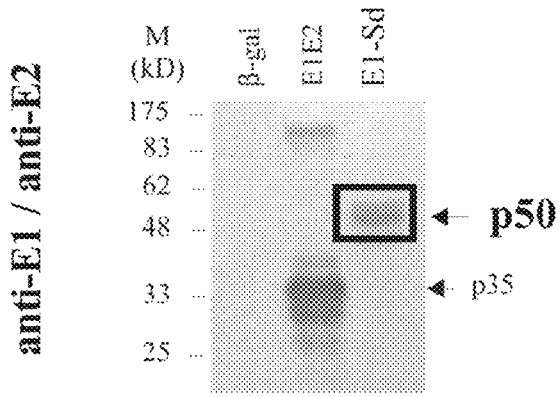

FIG. 7A to 7B show the co-production of the wild-type S protein of the HBV and the two fusion proteins E1-Sd and E2-Sd in Semliki/BHK-21 cells system Caption: M: molecular weight marker (kD); the β-gal, E1E2 or E1E2 and S tracks represent control cellular lysates derived from transfections of BHK-21 cells by the corresponding SFV RNA.

FIG. 7A proposes a schematic representation of the experimental protocol. The RNA derived from plasmids pSFV1-E1-Sd and pSFV1-E2-Sd are co-transfected individually in BHK-21 cells with the RNA derived from the plasmid pSFV1-S with the aim of obtaining the production of two types of chimeric subviral envelope particles S+E1-Sd and S+E2-Sd, the first comprising the wild-type S protein and the fusion protein E1-Sd, the second comprising the wild-type S protein and the fusion protein E2-Sd.

FIG. 7B shows a Western-blot revealed with an anti-E1 antibody on the intracellular particles purified from cells transfected by the RNA derived from vectors pSFV1-E1-Sd and pSFV1-S. The results show that the fusion protein E1-Sd (framed strip) is detected at the size of 50 kD corresponding to the theoretical size.

Figure 7E:
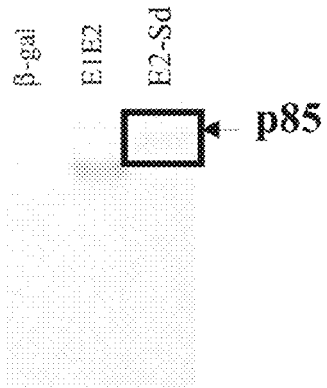
Figure 7C:
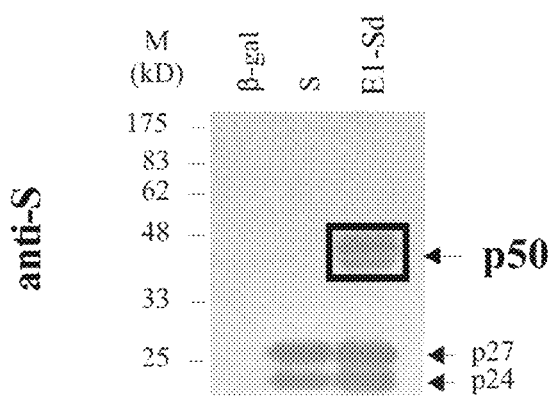

FIG. 7C shows a Western-blot revealed with an anti-S antibody on the intracellular particles purified from cells transfected by the RNA derived from vectors pSFV1-E1-Sd and pSFV1-S. The results show that the fusion protein E1-Sd (framed strip) is detected at the size of 50 kD corresponding to the theoretical size.

Figure 7F:
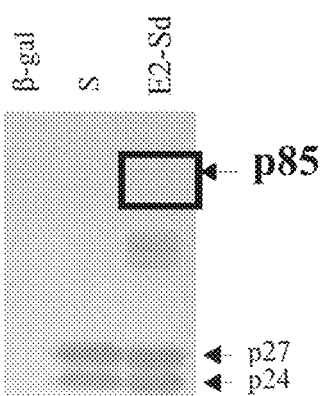
Figure 7D:
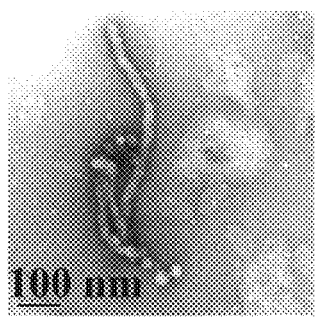

FIG. 7D shows a transmission electron microscopy micrograph by negative coloration on the intracellular particles purified from cells transfected by the RNA derived from plasmids pSFV1-E1-Sd and pSFV1-S. Bar: 100 nm.

FIG. 7E shows a Western-blot revealed with an anti-E2 antibody on the intracellular particles purified from cells transfected by the RNA derived from plasmids pSFV1-E2-Sd and pSFV1-S. The results show that the fusion protein E2-Sd (framed strip) is detected at the size of 85 kD corresponding to the theoretical size.

FIG. 7F shows a Western-blot revealed with an anti-S antibody on the intracellular particles purified from cells transfected by the RNA derived from plasmids pSFV1-E2-Sd and pSFV1-S. The results show that the chimeric protein E2-Sd (framed strip) is detected at the size of 85 kD corresponding to the theoretical size.

Figure 7G:
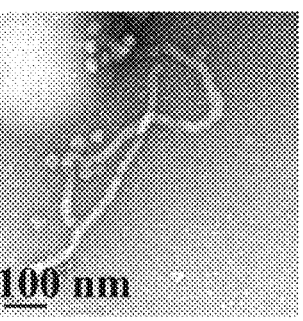

FIG. 7G shows a transmission electron microscopy micrograph by negative coloration on the intracellular particles purified from cells transfected by the RNA derived from plasmids pSFV1-E2-Sd and pSFV1-S. Bar: 100 nm.

Figure 8:
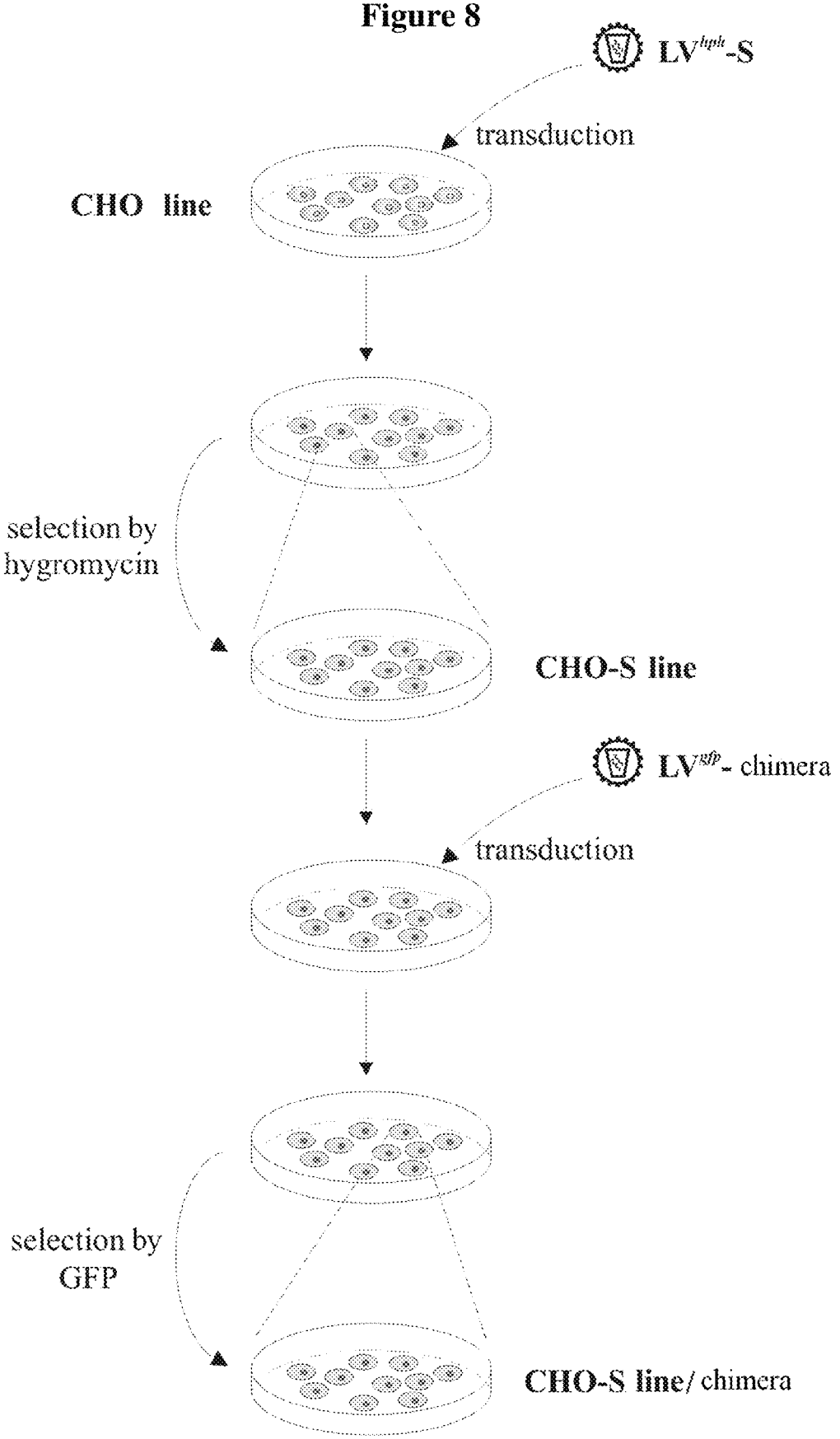

FIG. 8 represents the protocol for obtaining CHO clonal lines producing the wild-type S protein and the fusion proteins of the invention. It schematises how, from a CHO cell line, the transduction by a lentivirus (LV) containing a hygromycin resistance gene (hph) as well as the gene encoding for the wild-type S protein of the HBV enables the development of a first cellular clone named CHO-S and producer of the wild-type S protein. This clone was then over-transduced by a lentivirus (LV) containing the GFP gene (gfp) as well as the gene encoding for one of the two fusion proteins E1-Sd or E2-Sd. This second transduction enabled the development of two other cellular clones named CHO-S/E1-Sd and—S/E2-Sd.

Figure 9:
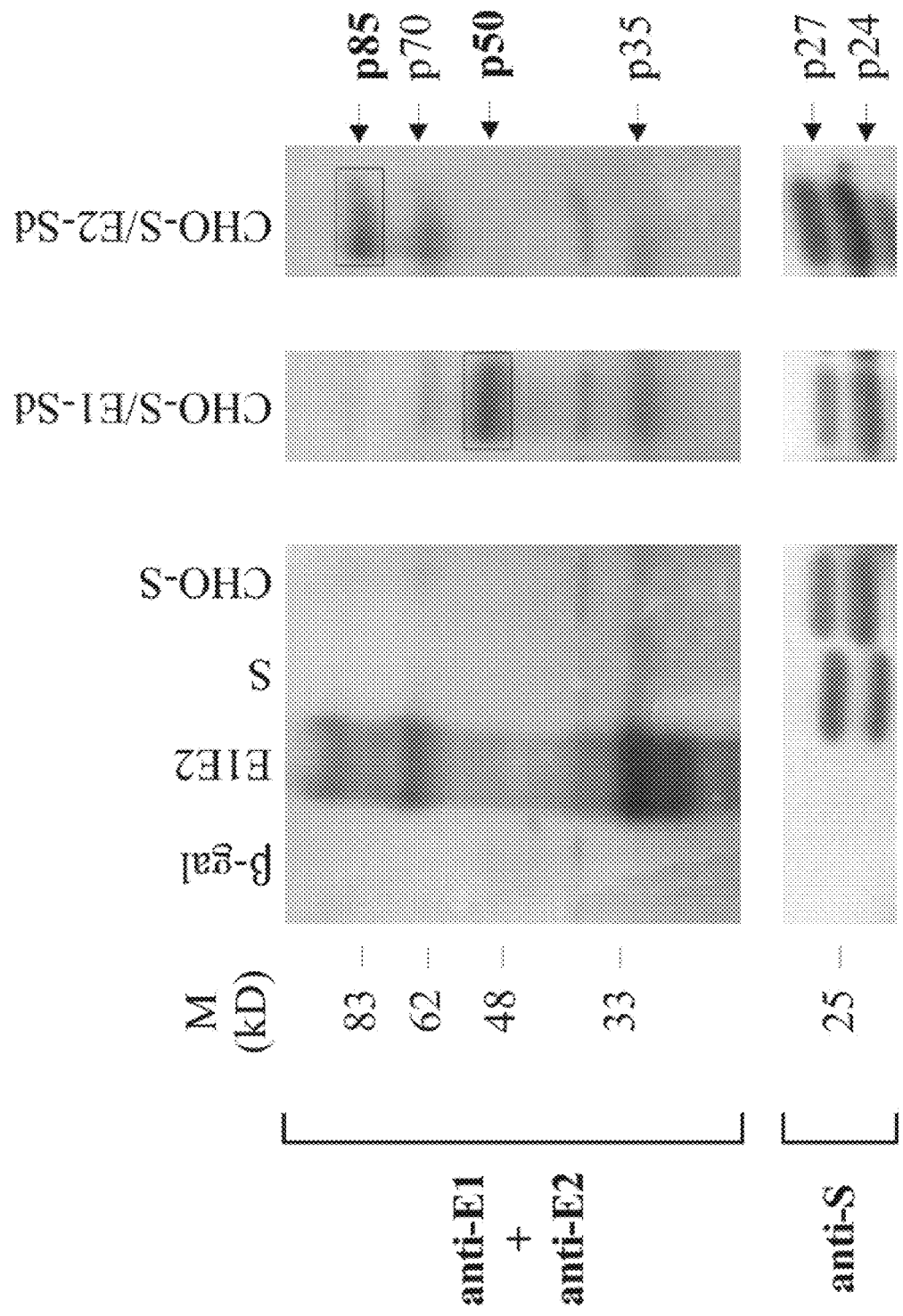

FIG. 9 shows an analysis by Western-blot of the intracellular production of the wild-type S protein and the fusion proteins of the invention in the different stable CHO clones. It shows that the intracellular proteins of the clones CHO-S, CHO-S/E1-Sd and CHO-S/E2-Sd are revealed by means of anti-E1, anti-E2 and anti-S antibodies. The searched-for fusion proteins are indicated by black boxes. M: molecular weight marker (kD); β-gal, E1E2 and S tracks: control cellular lysates derived from transfections of BHK-21 cells by the corresponding SFV RNA.

Figure 10:
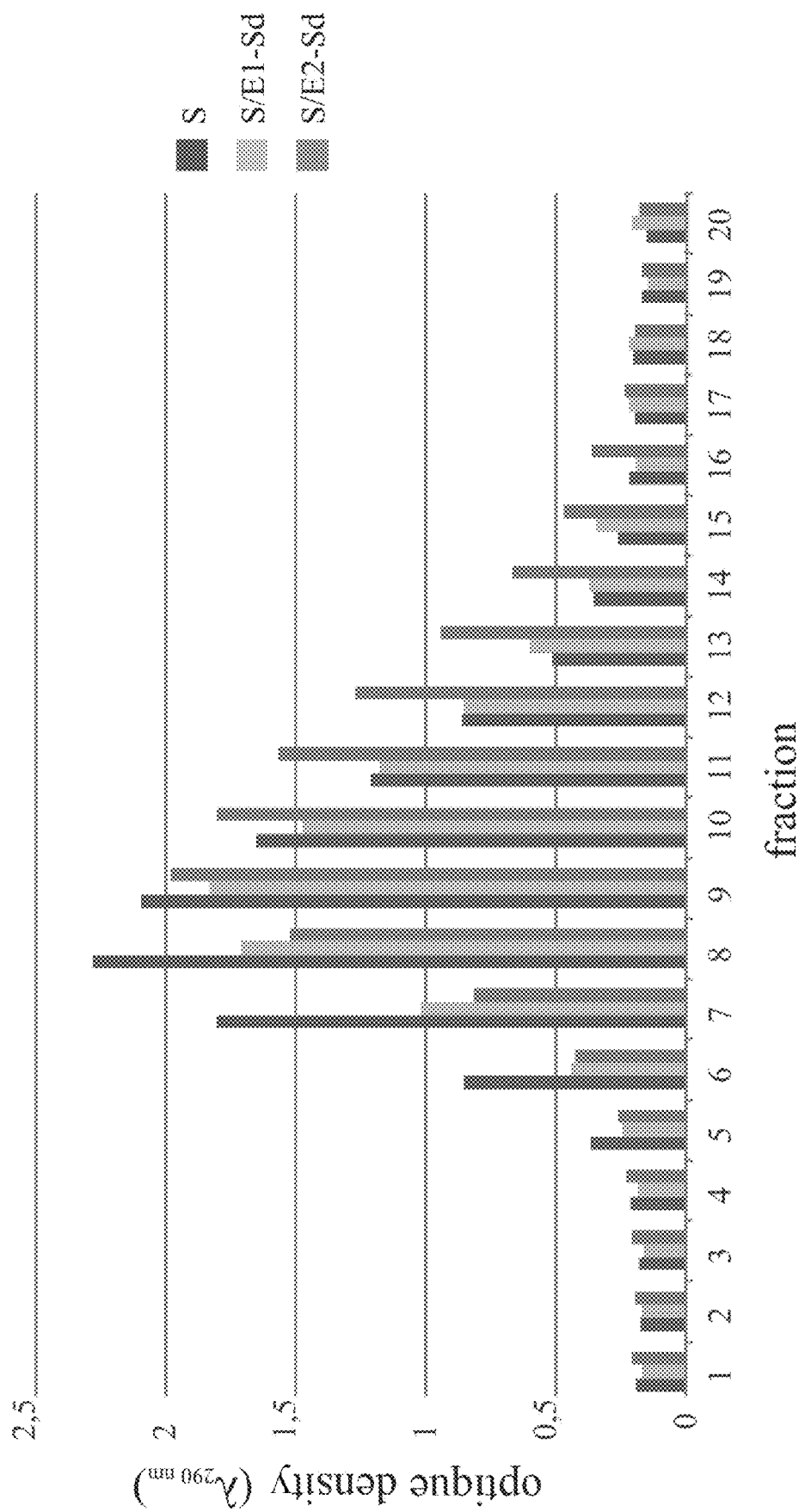

FIG. 10 represents a quantification histogram of the wild-type S protein by ELISA in the fractions collected from the CsCl gradient. The abscissa shows the different fractions collected, the ordinate indicates the optical density at 290 nm of each one. From the culture supernatants of the clones CHO-S, CHO-S/E1-Sd and CHO-S/E2-Sd, the subviral and chimeric S particles are purified by ultracentrifugation in CsCl. Fractions are collected from the summit of the gradient (fraction 1) and the quantity of wild-type S protein was evaluated by ELISA. The black histogram represents the distribution of the wild-type S protein in the fractions of the clone CHO-S, the light grey histogram represents the distribution of the wild-type S protein in the fractions of the clone CHO-S/E1-Sd and the dark grey histogram represents the distribution of the wild-type S protein in the fractions of the clone CHO-S/E2-Sd.

FIG. 11A shows that the protein content of the particles purified by CsCl has been analysed by Western-blot by means of anti-E1, anti-E2 and anti-S antibodies. The wild-type S protein is detected under its two glycosylation states (24 and 27 kD) in the three types of subviral particles. The fusion proteins E1-Sd or E2-Sd are detected at the sizes corresponding to the theoretical size respectively of 50 and 85 kD in their respective particles. M: molecular weight marker (kD).

FIG. 11B shows the analysis in negative coloration by transmission electron microscopy of the purification, from the supernatant of the clone CHO-S, of subviral particles resulting from the self-assembly of the wild-type S protein of spherical type of around 20 nm diameter. Bar: 20 nm.

FIG. 11C shows the analysis in negative coloration by transmission electron microscopy of the purification, from the supernatant of the clone CHO-S/E1-Sd, of chimeric subviral particles resulting from the assembly of the fusion protein E1-Sd in the presence of the wild-type S protein. These particles of spherical type are of around 20 nm diameter. Bar: 20 nm.

FIG. 11D shows the analysis in negative coloration by transmission electron microscopy of the purification, from the supernatant of the clone CHO-S/E2-Sd, of chimeric subviral particles resulting from the assembly of the fusion protein E1-Sd in the presence of the wild-type S protein. These particles of spherical type are of around 20 nm diameter. Bar: 20 nm.

By way of non limiting example, a particular embodiment of the invention is given hereafter, for obtaining subviral envelope particles of the hepatitis C virus (HCV) in Semliki system (cf. FIGS. 4 to 7).

This embodiment is based on obtaining immunogenic fusion proteins of the invention and in particular the fusion proteins E1-Sd or E2-Sd comprising, on the one hand, the S envelope protein deleted, at the N-terminal, of the transmembrane domain thereof (Sd), of the hepatitis B virus (HBV) and, on the other hand, the quasi integrality of one of the envelope proteins E1 or E2 of the HCV. This transitory embodiment demonstrates the capacity of assembling said deleted S protein (Sd), in the presence of the wild-type S protein, making it possible to obtain the aforementioned chimeric subviral particles, thanks especially to the high level of expression of the vector based on the replication properties of the Semliki forest virus (pSFV vector), before proceeding to obtaining stable clones that are producers of said particles by using lentiviral vectors.

EXAMPLE I

Obtaining Chimeric Subviral Envelope Particles of the Hepatitis C Virus in Semliki System (pSFV)

I.1) Construction of Plasmids p SFV 1-E1-Sd and pSFV1-E2-Sd.

The pSFV1 vector (Invitrogen) having a bicistronic structure of 11033 pb is used for the following constructions. This vector is provided with a promoter sequence of SP6-RNA-polymerase, inserted at the 5' side of the first cistron, in order to be able to initiate the synthesis of a complete RNA of positive polarity (RNA named 42S(+)) by transcription in vitro. After transfection into mammal cells, these recombinant RNA capped in vitro self-replicate in the presence of the nsP1-4 replicase of the SFV and serving for the production of proteins of interest by the intermediary of a secondary RNAm named 26S(+).

Wild-type complementary DNA (DNAc) or a hybrid nucleic acid molecule encoding for a fusion protein of the invention is obtained by carrying out several series of amplifications by polymerase chain reactions (PCR). Starting with the plasmid pSFV1-E1E2 (consisting in a SFV vector containing the sequence encoding for the two proteins E1 and E2 of the HCV), a first PCR, named PCR A, enabled the amplification of the sequences encoding for the envelope proteins E1 or E2 of the HCV with their transmembrane domain and preceded by sequences encoding for their respective transfer initiation peptide of addressing to the endoplasmic reticulum. Starting with the plasmid pHBV1.5 disclosed previously

[Patient, R., Hourioux, C., Sizaret, P. Y., Trassard, S., Sureau, C., and Roingeard, Y., (2007) Hepatitis B Virus Subviral Envelope Particle Morphogenesis and Intracellular Trafficking J Virol, 81(8), 3842-51], a second PCR, named PCR B, enabled the amplification of the sequence encoding for the deleted S protein of the HBV. The "HCV" parts of the sequences encoding for the fusion proteins according to the invention have been named "A" and the "HBV" parts have been named "B" (FIG. 5). The products of PCR A and B were quantified and purified on gel to then be included in equal parts in the final PCR. The use of bivalent HCV-HBV primers enabled the synthesis of products of PCR A and B having domains overlapping at their ends, making it possible, in the end, to obtain complete sequences of DNAc encoding for the fusion proteins of the invention.

I.1.1) Amplification of DNAc Sequences Encoding for the Fusion Proteins of the Invention (Especially E1-Sd and E2-Sd):

The amplifications by PCR are carried out in a reaction medium of 50 μL containing 50 ng of DNA, 15 μmol of each pair of primers (Proligo), 200 μM of each of the desoxyribonucleotides dNTP (Invitrogen) and 10 units of Taq-DNA-polymerase (Takara) comprising a correcting activity so as to minimise errors linked to successive amplifications (FIG. 5). By means of "Vector NTI Advance 10" (Invitrogen) and "Primer premier" (Biosoft International) software, the "forward" primers of A sequences and the "reverse" primers of B sequences were defined so as to generate a BamHI site at the respective 5' and 3' ends of the amplified DNA fragments.

Table 2 "Oligonucleotides used for the genetic amplification of the sequences A and B constituting chimeric sequences" below indicates the sequences of primers used.

The sequences corresponding to the HCV are represented therein in black type, those corresponding to the HBV in black underlined type, those corresponding to the BamHI restriction site in italic underlined type, those corresponding to the ATG initiation codon of the translation in bold type, those corresponding to the ATG termination codon of the translation in bold type.

TABLE 2

"Oligonucleotides used for the genetic amplification of the sequences A and B constituting chimeric sequences"

| Fragment of DNAc amplified | Primer pair | Primer sequence |
|---|---|---|
| e1-sd A | forward | 5'-ATA*GGATCC***ATG**ACAGGGAACCTTCCTGGTTGC-3' |
| | reverse | 3'-AACGACAAGCGGTCGTGTTCTTAGGAGT-5' |
| e1-sd B | forward | 5'-GCTGTTCGCCAGCACAAGAATCCTC-3' |
| | reverse | 3'-TAAAAGAAAACAGAGACCCATATGTAAATT*CCTAGG*ATA-5' |
| e2-sd A | forward | 5'-ATA*GGATCC***ATG**GGGAACTGGGCGAAGGT-3' |
| | reverse | 3'-ACGATGAGTATAGGGTTTGTTCTTAGGAGTGTTATGG-5' |
| e2-sd B | forward | 5'-GCTACTCATATCCCAAACAAGAATCCTCACAATACC-3' |
| | reverse | 3'-TAAAAGAAAACAGAGACCCATATGTAAATT*CCTAGG*ATA-5' |

These amplification reactions, carried out in an "iCycler" thermal cycler (Biorad), consisted in an initial denaturation of 5 minutes at 95° C., followed by 25 cycles comprising a denaturation of 1 minute at 95° C., an hybridisation of 1 minute at 60° C. and an elongation of 1 minute at 69° C. The 25 cycles are followed by a final elongation of 10 minutes at 69° C. The fragments amplified by the PCR A and B are purified on 1% agarose gel by means of the "Wizard SV Gel and PCR Clean-Up System" system (Promega) in accordance with the manufacturer's recommendations. The purified fragments of the PCR A and B are then hybridised by a PCR named PCRHYB in the absence of primers for 10 cycles then are amplified by a final PCR named PCRFIN for 25 cycles in the presence of "forward" primers of sequences A and "reverse" primers of sequences B. The programmes of cycles of the latter two PCR are similar to those used for the PCR A and B. The amplified fragments of molecules of hybrid nucleic acids of the invention thereby obtained are purified on gel as above.

I.1.2) Cloning of Hybrid Sequences of DNAc in the pSFV1 Vector

The PCRFIN products purified are cloned in the pGEM-T® vector ("pGEM-T Easy Vector System", Promega) in accordance with the manufacturer's recommendations. The fragments of hybrid nucleic acids molecules of the invention are freed of the pGEM-T® by restriction with the enzyme BamHI (Biolabs) then cloned at the BamHI site of the plasmid pSFV1. The different plasmids comprising the fusion proteins of the invention (especially the plasmids pSFV1-E1-Sd and pSFV1-E2-Sd) are amplified by bacterial transformation then purified by maxi-preparation of DNA in phenol/chloroform. The orientation of the insert is verified by enzymatic restriction and all of the constructions are verified by sequencing.

I-2) Obtaining the Cell Line Temporarily Transfected by the RNA of Different SFV Constructions The culture procedures for new-born hamster kidney cells (BHK-21) as well as the in vitro transcription protocols of SFV matrix plasmids and transfection of self-replicating recombinant RNA were identical to those described previously [Patient, R., Hourioux, C., Sizaret, P. Y., Trassard, S., Sureau, C., and Roingeard, P., (2007) Hepatitis B Virus Subviral Envelope Particle Morphogenesis and Intracellular Trafficking J Virol, 81(8), 3842-51]. The pSFV-S construction, expressing the wild-type S protein of the HBV and previously disclosed in the preceding article, was used as control.

I-3) Analysis of the Intracellular Production of Wild-Type Chimeric Envelope Proteins The biochemical procedures for analysing the proteins of interest (especially 5, Sd, E1, E2, E1-Sd, E2-Sd etc.) by immunofluorescence confocal microscopy and by Western Blot, the ultra-structural analysis procedures of cells transfected in transmission electron microscopy as well as the procedures of quantification (ELISA)/purification (sucrose gradient then affinity chromatography) of HCV-HBV chimeric subviral envelope particles are those disclosed previously [Patient, R., Hourioux, C., Sizaret, P. Y., Trassard, S., Sureau, C., and Roingeard, P., (2007) Hepatitis B Virus Subviral Envelope Particle Morphogenesis and Intracellular Trafficking I Virol, 81(8), 3842-51].

The detection of wild-type S proteins E1 and E2 of HCV and fusion proteins of the invention is carried out by means of a monoclonal murine anti-E1 antibody (A4, provided by Dr Harry Greenberg, University of Stanford, Calif.) [Dubuisson, J., Hsu, H. H., Cheung, R. C., Greenberg, H. B., Russell, D. G., and Rice, C. M. (1994). Formation and intracellular localization of hepatitis C virus envelope glycoprotein complexes expressed by recombinant vaccinia and Sindbis viruses. J Virol 68(10), 6147-60)] or anti-E2 antibody (H52, provided by Dr Jean Dubuisson, Institut Pasteur de Lille) [Deleersnyder, V., Pillez, A., Wychowski, C., Blight, K., Xu, J., Hahn, Y. S., Rice, C. M., and Dubuisson, J. (1997). Formation of native hepatitis C virus glycoprotein complexes. J Virol 71(1), 697-704].

I-4) Analysis of the Culture Supernatant.

After transfection, the culture supernatant of around $10^7$ cells transfected is cleaned by a centrifugation of 10 minutes at 1500 g then is ultra-centrifuged at 4° C. for 16 hours at 35,000 rpm by means of a SW41 rotor (L70 Ultracentrifuge, Beckman). The residue is taken up in 50 µL of the lysis buffer then analysed by Western-blot.

I.5) Production of Fusion Proteins E1-Sd and E2-Sd of the Invention

Sixteen hours after the transfection by the plasmids pSFV1 comprising the hybrid nucleic acid molecules of the invention, pit1-e1-sd, pit2-e2-sd, the BHK-21 cells were lysed then analysed by Western-blot by means of monoclonal anti-E1 and anti-E2 antibodies. After transitory production in BHK-21 cells, the sizes of the fusion proteins E1-Sd and E2-Sd are around 50 kD for the protein E1-Sd and around 85 kD for the protein E2-Sd. These results, correlated with the intense immunofluorescence obtained by the detection of said fusion proteins of the invention with the anti-E1, anti-E2 and anti-S antibodies, show that they are correctly produced, correctly glycosylated, and thus laid out according to the desired transmembrane topology (FIGS. 6A to 6D).

So as to restore the secretion capacity of the different fusion proteins of the invention, co-transfections are carried out by introducing in trans the wild-type form of the S protein of the HBV to each of the fusion proteins of the invention (FIG. 7A). Sixteen hours after the transfection, the co-transfected cells are milled and the intracellular subviral particles are purified by sucrose gradient then affinity chromatography as disclosed previously [Patient, R., Hourioux, C., Sizaret, Trassard, S., Sureau, C., and Roingeard, Y., (2007) Hepatitis B Virus Subviral Envelope Particle Morphogenesis and Intracellular Trafficking J Virol, 81(8), 3842-51]. In all cases, the subviral particles are studied by transmission electron microscopy and by Western-blot using the anti-S, anti-E1 or anti-E2 antibodies described previously in example I.3 (FIGS. 7B to 7G).

Transmission electron microscopy images show that in all of these experiments of co-production of the wild-type S protein with one of the fusion proteins of the invention it is possible to produce an important quantity of spherical and filamentous subviral particles. Western-blot analyses show that these more or less filamentous subviral particles are rich in fusion proteins of the invention.

The implementation according to example 1 of the present invention in "Semliki" system shows that the fusion proteins of the invention containing the quasi-integrality of the proteins E1 or E2 of the HCV (their transmembrane domain replacing that located at the N-terminal of the S protein of the HBV) assembly themselves into chimeric subviral particles of same nature as the subviral particles used in the production of vaccines against hepatitis B, thereby facilitating the purification of said chimeric subviral particles of the invention, and potentially, the development of an industrial application of a vaccine against HCV, reproducing that of the vaccine against HBV.

The implementation according to example 1 of the present invention also shows the production of fusion proteins comprising the non truncated proteins E1 and/or E2 of HCV. This characteristic may prove to be determining in inducing an optimal neutralising and cellular immune response.

However, in "Semliki" system, the chimeric subviral particles are produced by temporary transfection of cells. Indeed, the high cytotoxicity of these vectors does not make it possible to obtain an efficient secretion in the long term of chimeric subviral particles. Furthermore, the purification of said particles from the homogenate of the cells co-transfected necessitates a relatively cumbersome implementation, ill suited to industrial production.

By way of non limiting example, an embodiment is disclosed with reference to FIGS. 8 to 11 for obtaining subviral envelope particles of the hepatitis C virus from CHO type lines expressing in a stable manner the wild-type S protein of the HBV as well as the fusion protein E1-Sd or the fusion protein E2-Sd. Obtaining these stable clones of CHO is made possible by the use of lentiviral type integrative vectors. One of the assets of this system is that the production of recombinant proteins, such as the fusion proteins of the invention, does not have major short term cytotoxic effects such as those encountered with the SFV system.

One of the objectives of this embodiment is also to obtain a cellular system of production of chimeric subviral particles of the invention similar to that used for the industrial manufacture of the vaccine against hepatitis B.

EXAMPLE II

Obtaining Subviral Envelope Particles of the Hepatitis C Virus in Lentiviral System The use of lentiviral vectors has made it possible to develop cellular clones producing in a stable manner the wild-type S protein of the HBV associated with one of the fusion proteins E1-Sd and/or E2-Sd.)

(II-1) pLENTI Plasmid Lentiviral Vectors.

The pLENTI$^{hph}$ plasmid of 9955 pb, comprising the selection gene hph, and encoding for a hygromycin resistance protein as selection marker was used for the following constructions

[Naldini, L., Blomer, U., Gallay, P., Ory, D., Mulligan, R., Gage, F. H., Verma, I. M., and Trono, D. (1996). In vivo gene delivery and stable transduction of non-dividing cells by a lentiviral vector. Science 272(5259), 263-7].

Firstly, the nucleic acid sequence encoding for the wild-type S protein is released from pSFV1-S as disclosed previously [Patient, R., Hourioux, C., Sizaret, P. Y., Trassard, S., Sureau, C., and Roingeard, P., (2007) Hepatitis B Virus Subviral Envelope Particle Morphogenesis and Intracellular Trafficking J Virol, 81(8), 3842-51] by restriction with the enzyme BamHI (Biolabs) then purified on 1% agarose gel by means of the "Wizard SV Gel and PCR Clean-Up System" system (Promega) in accordance with the manufacturer's recommendations. This purified fragment was then cloned at the BamHI site included in the multiple cloning site of the pLENTI$^{hph}$ plasmid by means of T4-DNA-ligase (Biolabs) in accordance with the manufacturer's recommendations. The pLENTI$^{hph}$-S plasmid was finally amplified by bacterial transformation then purified by maxi-preparation of DNA by means of the "Nucleobond PC 500 Kit" system (Qiagen) in accordance with the manufacturer's recommendations. The orientation of the insert was then verified by enzymatic restriction.

In the same way, the different hybrid nucleic acids molecules of the invention of DNAc encoding for the fusion proteins of the invention (especially E1-Sd and E2-Sd) are cloned at the BamHI site of the pLENTI$^{gfp}$ plasmid. The plasmids thereby obtained (especially pLENTIgfp-E1-Sd and E2-Sd) are then amplified, purified and sequenced (cf. II-1).

II-2) Production of Recombinant Lentivirus.

Twenty four hours before the transfection of the lentiviral plasmids, HEK 293T cells were seeded at a rate of $3.10^6$ cells per 75 cm$^2$ flask (Falcon) in DMEM-glutamax medium (Invitrogen) supplemented with 10% of decomplemented foetal bovine serum (ATGC), 100 UI/mL of penicillin and 100 µg/mL of streptomycin. These cells were cultivated under 5% of $CO_2$ and the culture medium was changed 4 hours before the transfection. One pmole of each plasmid p8.74, pVSV-G and pLENTI (pLENTI$^{hph}$-S, pLENTI$^{gfp}$-E1-Sd, E2-Sd) was transfected simultaneously in the cells HEK 293T by means of the "Calcium Phosphate. Transfection Kit" system (Invitrogen) in accordance with the manufacturer's recommendations. The culture medium is changed 24 hours after the transfection and collected 48 hours and 72 hours after the transfection. The media collected are filtered at 0.45 µm then concentrated by ultracentrifugation on a 20% sucrose cushion at 4° C. for 90 minutes at 100.000 g. The residue containing the recombinant lentiviruses is taken up in 500 µL of phosphate buffer (PBS) and conserved at −80° C. Batches of recombinant lentiviral vectors of the invention are generated, of which especially the lentiviral vectors LV$^{hph}$-S, LV$^{gfp}$-E1-Sd, LV$^{gfp}$-E2-Sd. The titration of the lentiviral transducing units (TU) of each batch is determined from the assay of the p24 protein and by means of the "Innotest HIV Kit" (Innogenetics) system in accordance with the manufacturer's recommendations.)

II-3) Cellular Culture and Transduction.

The cell line used for the stable and constitutive production of HCV-HBV chimeric subviral particles is a Chinese hamster ovary line named CHO. This line has already been perfectly validated for the production of recombinant proteins of medical interest, and especially for the vaccine against hepatitis B "GenHevac B Pasteur®" (Sanofi Pasteur MSD). These CHO cells are cultivated under 5% $CO_2$ in DMEM-F12 medium (Invitrogen) supplemented with 10% decomplemented foetal bovine serum (ATGC), 100 UI/mL of penicillin and 100 µg/mL of streptomycin. Twenty four hours before the transduction, the CHO cells are cultured in a 6-well plate (Falcon) at a rate of 105 cells per well. They are then transduced in a new medium with a multiplicity of infection of 2.5 (i.e. a ratio of transducing units (TU) per cell of 2.5) in the presence of 4 µg/mL of polybrene (Sigma-Aldrich) then cultivated for 24 hours. The following day, the transduction medium is removed, the cells obtained according to the implementation of the present invention are rinsed in PBS buffer then are maintained normally in culture for 2 more days.

II-3.1) Generation of a Stable CHO Clone Producer of the Wild-Type S Protein

The CHO line used is transduced with the lentivirus LV$^{hph}$-S according to the protocol described above, and schematised in FIG. 8. The transduction efficiency is verified by immunofluorescence by means of an antibody directed against the wild-type S protein according to a protocol disclosed previously [Patient, R., Hourioux, C., Sizaret, P. Y., Trassard, S., Sureau, C., and Roingeard, Y., (2007) Hepatitis B Virus Subviral Envelope Particle Morphogenesis and Intracellular Trafficking J Virol, 81(8), 3842-51]. Three days after the transduction, the cells are trypsinized, re-cultivated in a culture box of 10 cm diameter (Falcon) in the presence of 1 mg/mL of hygromycin (Euromedex) and maintained in culture for three weeks. The emerging cellular clones are recovered by cloning cylinder (Invitrogen) then amplified in 24-well plates (Falcon). The CHO clone used subsequently is selected after quantification in the culture supernatant of the wild-type S protein by ELISA [Patient, R., Hourioux, C., Sizaret, P. Y., Trassard, S., Sureau, C., and Roingeard, P., (2007) Hepatitis B Virus Subviral Envelope Particle Morphogenesis and Intracellular Trafficking J Virol, 81(8), 3842-51]. This cellular clone has been named CHO-S.

II-3.2) Generation of Stable CHO Clones Producers of the Wild-Type S Protein of the HBV Virus and Fusion Proteins of the Invention E1-Sd and E2-Sd.

The CHO-S cellular clone is later over-transduced with recombinant lentivirus LV$^{gfp}$ encoding for the GFP protein as selection marker, and comprising a hybrid nucleic acid molecule of the invention, especially the vector lentivirus LV$^{gfp}$-PIT1-E1-Sd or LV$^{gfp}$-PIT2-E2-Sd according to the protocol described above in §II-3.1. (FIG. 8). On account of the presence of the GFP protein, the efficiency of transduction is verified by means of a FACScalibur cytometer in flux (Becton-Dickinson). Three days after the transduction, the cells are trypsinized, re-cultivated at limit dilution in a 96-well plate (Falcon) at a rate of 1 cell per well and they are maintained in culture for three weeks. The emerging GFP+ cellular clones are recovered then amplified in large quantity. The cellular clones thereby obtain are especially named CHO-E1-Sd or CHO-E2-Sd.

II-4) Analysis of the Intracellular Production of Chimeric and Wild-Type Envelope Proteins of the HBV and the HCV.

The biochemical analysis procedures by immunofluorescence and by Western Blot of the proteins of interest S, E1-Sd or E2-Sd of each clone cellular have already been disclosed previously, for example I in §1-4.

II-5) Purification and Analysis of Chimeric Subviral Particles Derived from the Culture Supernatant.

Around 200 mL of culture supernatant for each clone selected is clarified by centrifugation at 4° C. for 10 minutes at 1500 g. The proteins are precipitated by addition of a solution of $(NH_4)_2SO_4$ (pH 7.5; 45% final) then centrifugation at 4° C. for 15 minutes at 10.000 g. The residue is taken up in a minimum volume of TNE buffer (10 mM Tris/HCl pH 7.5/100 mM NaCl/1 mM EDTA). After a series of dialyses in TNE buffer, CsCl is added until a density of around 1.22 g/cm$^3$ is obtained, then two successive isopycnal ultra-centrifugations are carried out at 15° C. for 48 hours at 40.000 rpm by means of a 45Ti rotor (L70 Ultracentrifuge, Beckman). Fractions are collected from the summit of the gradient and the wild-type S protein is quantified by ELISA [Patient, R., Hourioux, C., Sizaret, P. Y., Trassard, S., Sureau, C., and Roingeard, P., (2007) Hepatitis B Virus Subviral Envelope Particle Morphogenesis and Intracellular Trafficking J Virol, 81(8), 3842-51]. The positive fractions were mixed and dialysed at 4° C. in THE buffer.

The purified preparations were finally analysed by Western Blot and by transmission electron microscopy as disclosed previously in example I au §1-4.

II-6) Intracellular Production of the S Protein and Fusion Proteins.

Following their expansion, the CHO-S, CHO-E1-Sd and CH0-E2-Sd cellular clones were analysed by immunofluorescence then Western-blot by means of antibodies directed against the proteins Sd, E1 or E2 (cf.: example I in §1-4 and FIG. 9). As expected, all of the clones enable an intense production of the wild-type S protein of the HBV under two states of glycosylation (p24 and gp27). Similarly, the CHO-E1-Sd and CHO-E2-Sd clones enable an intense and cytoplasmic production of the fusion proteins of the invention of expected sizes. These results thus show that all of the fusion proteins of the invention are correctly produced in the CHO line.

II-7) Purification of Particles

A first purification test was carried out from 200 mL of culture supernatant of the CHO-5, CHO-E1-Sd or CHO-E2-Sd clone. These supernatants, the concentration in wild-type S protein of which is evaluated by ELISA at around 100 ng/mL for the three clones, are ultra-centrifuged on an isopycnal gradient of CsCl. The fractions of each gradient formed are then analysed by a quantification of the wild-type S protein (FIG. 10). For the three types of chimeric subviral particles purified (S, E1-Sd and E2-Sd), the wild-type S protein concentration peak was able to be observed in the fraction n° 9, corresponding to a density between 1.17 and 1.18. The fractions n° 8, 9 and 10 of each preparation are then reassembled to be dialysed then analysed by Western-blot by means of antibodies directed against the wild-type proteins S, E1 or E2 (cf.: example I in §1-4 and (FIG. 11A) and by transmission electron microscopy in negative coloration (FIGS. 11B to 11D).

A deposition corresponding to one μg of wild-type S protein for each purification is carried out for the analysis in acrylamide gel. This makes it possible to show that the fusion proteins of the invention E1-Sd and E2-Sd are detected at the expected size and in respectable quantity in their respective preparation by the antibodies anti-E1 or anti-E2. Similarly, the two expected forms of glycosylation of the wild-type S protein are detected in each preparation. The analysis by negative coloration in transmission electron microscopy made it possible to confirm the presence of spherical subviral envelope particles of around 20 nm diameter in the three preparations studied.

EXAMPLE III

Obtaining Subviral Envelope Particles Comprising the Two Fusion Proteins E1-Sd and E2-Sd A new pLENTI$^{gluc}$ plasmid comprising the selection gene glue of *Gaussia princeps*, in place of the gene gfp, is formed and encodes for a luciferase (GLuc) secreted as selection marker. The fragment of DNAc encoding for the fusion protein E1-Sd is cloned at the BamHI site of the pLENTI$^{gluc}$ plasmid. The pLENTI$^{gluc}$-E1-Sd plasmid thereby obtained is amplified, purified and sequenced (cf. II-1).

III.1 Production of Recombinant Lentivirus.

Twenty four hours before the transfection of the lentiviral plasmids, HEK 293T cells were cultured at a rate of 3.10$^6$ cells per 75 cm$^2$ flask (Falcon) in DMEM-glutamax medium (Invitrogen) supplemented with 10% decomplemented foetal bovine serum (ATGC), 100 UI/mL of penicillin and 100 μg/mL of streptomycin. These cells are cultivated under 5% CO, and the culture medium is changed 4 hours before the transfection. One pmole of each p8.74, pVSV-G and pLENTI$^{gluc}$-E1-Sd plasmid is transfected simultaneously into the HEK 293T cells by means of the "Calcium Phosphate Transfection Kit" system (Invitrogen) in accordance with the manufacturer's recommendations. The culture medium is changed 24 hours after the transfection and collected 48 hours and 72 hours after the transfection. The media collected are filtered at 0.45 μm then concentrated by ultracentrifugation on a 20% sucrose cushion at 4° C. for 90 minutes at 100.000 g. The residue containing the recombinant lentivirus is taken up in 500 μL of phosphate buffer (PBS) and conserved at −80° C. A new batch of recombinant lentivirus is thereby generated: LV$^{gluc}$-E1-Sd. The titration of the lentiviral transducing units (TU) of this batch is determined from the assay of the p24 protein and by means of the "Innotest HIV Kit" systems (Innogenetics) in accordance with the manufacturer's recommendations.

III.2. Generation of a Stable CHO Clone Producer of the Wild-Type S Protein of the HBV Virus, Fusion Protein of the Invention E2-Sd and E1-Sd.

The culture of the CHO cells and the method of transduction disclosed and used for example II is adapted to this example. After a first transduction with the lentivirus enabling the CHO-S cellular clone to be obtained, a second transduction is carried out with the lentivirus LV$^{gfp}$-E2-Sd according to the protocol disclosed for example II, enabling the CHO-E2-Sd cellular clone to be obtained.

The latter is again transduced with the lentivirus LV$^{gluc}$-E1-Sd according to the protocol disclosed above. Three days after the transduction, the cells are trypsinized and re-cultured at limit dilution in a 96-well plate (Falcon) at a rate of 1 cell per well. The cells are maintained under culture for three weeks, at the end of which the supernatant of the emerging cellular clones is collected. In these supernatants, the presence of luciferase is detected by the measurement of its enzymatic activity by means of the "*Gaussia* Luciferase Assay Kit" system (Biolabs) in accordance with the manufacturer's recommendations. The light emitted by the enzymatic reaction is measured by means of a Centro LB 960 luminometer (Berthold Technologies). The cellular clones corresponding to the supernatants GLuc+ are recovered then amplified in large quantity. The clone thereby obtained is named CHO-S/E2-Sd/E1-Sd.

EXAMPLE IV

In Vivo Analysis of the Immunological Activity of Chimeric Subviral Particles 5 to 10 milligrammes of chimeric subviral particles for each type of particle (S+E1-Sd, S+E2-Sd, S only of the HBV) are purified from the supernatant of cellular culture according to the method described above.

Four groups of mice and rabbits are made use of for an immunisation series.

The immunisation is carried out by three injections of 10 micrograms of the immunogenic according to the classical method.

The first group is immunised by the particles S+E1-Sd.

The second group is immunised by the particles S+E2-Sd.

The third group is immunised by the particles HBV S alone.

The fourth group is immunised by the mixture of chimeric subviral particles S+E1-Sd and chimeric subviral particles S+E2-Sd.

The global humoral response produced in these animals is detected by ELISA and Western blot analysis. For the anti-S antibodies, commercial ELISA (Abbott, Roche) make it possible to determine the number of international units (UI) of anti-S antibodies, which are known to have neutralising properties against HBV. A concentration at least equal to 10 UI is considered as protective against HBV. (Jilg W, et al. Hepatitis B-vaccination: Strategy for booster doses in high risk population groups. Progress in Hepatitis B Immunization. Eds. P. Coursaget et al. Collogue Inserm. 1990; 190: 419-427.) For the anti-E1 and ant-E2 antibodies, the Western blot is used to evaluate whether an anti-E1 and anti-E2 antibody response is generated. If this is the case, this analysis is completed by an analysis of the presence of anti-E1 and anti-E2 antibodies neutralising the virus. The analysis of the neutralisation of HCV by these antibodies is performed in the JFH-1 system (Wakita et al., Nat Med 2005) which makes it possible to propagate an HCV strain of genotype 2 in vitro, or by the use of chimeric viral strains comprising the structural proteins of the HCV of genotype 1 or 3.

The invention claimed is:

1. An immunogenic fusion protein comprising the following two peptides:
   a) at the C-terminal side of the fusion protein, a first peptide consisting of the amino acid sequence of the S protein of human hepatitis B virus (HBV), wherein the S protein is deleted of the transmembrane domain located at the N-terminal thereof, and
   b) at the N-terminal side of the fusion protein, a second peptide consisting of the amino acid sequence of the transmembrane domain and the ectodomain of an envelope protein of hepatitis C virus (HCV), said envelope protein being selected from the group consisting of protein E1, protein E2, and a fusion peptide comprising protein E1 and protein E2.

2. The immunogenic fusion protein according to claim 1, wherein the first peptide and the second peptide are contiguous, and the C-terminal end of the second peptide is bonded in a covalent manner to the N-terminal end of the first peptide.

3. The immunogenic fusion protein according to claim 1, wherein the first peptide comprises the amino acid sequence of SEQ ID NO: 2.

4. The immunogenic fusion protein according to claim 1, wherein the second peptide comprises the amino acid sequence of SEQ ID NO: 6.

5. The immunogenic fusion protein according to claim 1, wherein the fusion protein comprises the amino acid sequence of SEQ ID NO: 10.

6. A subviral envelope particle, comprising:
   a protein comprising a wild-type S protein of the surface antigen of a hepatitis B virus isolate, and
   at least one immunogenic fusion protein according to claim 1.

7. An immunogenic composition comprising as active ingredient the subviral envelope particle according to claim 6 and a pharmaceutically acceptable vehicle.

8. The immunogenic composition according to claim 7, comprising a first and a second subviral envelope particle, wherein the first subviral envelope particle comprises an immunogenic fusion protein wherein the N-terminal side consists of the transmembrane domain and the ectodomain of an HCV E1 protein and the second subviral envelope particle comprises an immunogenic fusion protein wherein the N-terminal side consists of the transmembrane domain and the ectodomain of an HCV E2 protein.

9. The immunogenic composition according to claim 7, wherein the at least one immunogenic fusion protein comprises the amino acid sequence of SEQ ID NO: 8.

10. The subviral particle according to claim 6, wherein the at least one immunogenic fusion protein comprises the fusion protein of SEQ ID NO:10.

11. The subviral particle according to claim 6, wherein the at least one immunogenic fusion protein comprises the fusion protein of SEQ ID NO:8 and the fusion protein of SEQ ID NO:10.

12. An immunogenic composition comprising:
    at least one fusion protein according to claim 1, or a subviral envelope particle comprising a wild-type S protein of the surface antigen of a hepatitis B virus isolate and said at least one fusion protein; and
    a pharmaceutically acceptable vehicle.

13. The immunogenic composition according to claim 12, wherein the at least one fusion protein comprises SEQ ID NO: 10.

14. The immunogenic fusion protein according to claim 1, wherein the HBV is an isolate of the HBV virus.

15. The immunogenic fusion protein according to claim 14, wherein the isolate is HBVadw.

16. The immunogenic fusion protein according to claim 1, wherein the HCV is an isolate of the HCV virus.

17. The immunogenic fusion protein according to claim 16, wherein the isolate is HCV-1a.

18. The immunogenic fusion protein according to claim 1, wherein said envelope protein is E2.

19. A subviral envelope particle, comprising:
    a protein comprising a wild-type S protein of the surface antigen of hepatitis B virus, and the immunogenic fusion protein according to claim 18.

20. The immunogenic fusion protein according to claim 1, wherein said envelope protein is E1.

21. A subviral envelope particle, comprising:
    a protein comprising a wild-type S protein of the surface antigen of hepatitis B virus, and the immunogenic fusion protein according to claim 20.

* * * * *